United States Patent [19]
Negi et al.

[11] Patent Number: 5,741,902
[45] Date of Patent: Apr. 21, 1998

[54] 7-ACYL-3-(SUBSTITUTED CARBAMOYLOXY) CEPHEM COMPOUNDS AND PROCESS FOR THEIR PREPARATION

[75] Inventors: Shigeto Negi, Ibaraki Prefecture; Motosuke Yamanaka, Chiba Prefecture; Kanemasa Katsu, Ibaraki Prefecture; Isao Sugiyama, Ibaraki Prefecture; Yuuki Komatu, Ibaraki Prefecture; Atsushi Kamata, Ibaraki Prefecture; Akihiko Tsuruoka, Ibaraki Prefecture; Yoshimasa Machida, Ibaraki Prefecture, all of Japan

[73] Assignee: Eisai Co., Ltd., Japan

[21] Appl. No.: 464,341

[22] Filed: Jun. 5, 1995

Related U.S. Application Data

[62] Division of Ser. No. 393,074, Feb. 23, 1995, Pat. No. 5,563,265, which is a continuation of Ser. No. 209,484, Mar. 14, 1994, Pat. No. 5,559,225, which is a continuation of Ser. No. 789,669, Nov. 8, 1991, abandoned.

[30] Foreign Application Priority Data

| Nov. 9, 1990 | [JP] | Japan | 2-302783 |
| Feb. 14, 1991 | [JP] | Japan | 3-40747 |
| Mar. 8, 1991 | [JP] | Japan | 3-67709 |
| Apr. 12, 1991 | [JP] | Japan | 3-169512 |

[51] Int. Cl.$^6$ ............ C07D 501/18; C07D 501/40
[52] U.S. Cl. ........................... 540/222; 540/215
[58] Field of Search ........................ 540/222, 215

[56] References Cited

U.S. PATENT DOCUMENTS 4,278,671  7/1981  Ochiai et al. ................ 424/246

OTHER PUBLICATIONS

Numata et al, Chemical Abstracts, vol. 88, Entry 190871(1978).

*Primary Examiner*—John M. Ford
*Attorney, Agent, or Firm*—Wenderoth, Lind & Ponack

[57] ABSTRACT

A 7-acyl-3-substituted carbamoyloxy cephem compound represented by the following formula (1):

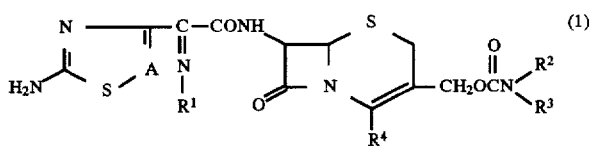

wherein A means a —CH= or —N= group; $R^1$ denotes a hydroxyl, lower alkoxyl, fluorine-substituted lower alkoxyl or protected hydroxyl group; $R^2$ and $R^3$ are the same or different and individually represent a lower alkyl, hydroxyl-substituted lower alkyl, a carbamoyl-substituted lower alkyl group or cyano-substituted lower alkyl group, $R^2$ is a hydrogen atom and $R^3$ is a lower alkoxyl or alkyl group optionally substituted by one or more halogen atoms, or the group

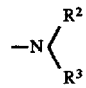

means a 4–6 membered heterocyclic group, which contains one nitrogen atom, or a morpholino group, said heterocyclic group or morpholino group being optionally substituted by one or more lower alkyl, hydroxyl and/or hydroxyl-substituted lower alkyl groups; and $R^4$ denotes a carboxyl or protected carboxyl group; or a pharmaceutically acceptable salt thereof; and a process for the preparation thereof; as well as an antibacterial composition containing the above cephem compound.

4 Claims, No Drawings

7-ACYL-3-(SUBSTITUTED CARBAMOYLOXY) CEPHEM COMPOUNDS AND PROCESS FOR THEIR PREPARATION

This is a divisional application of Ser. No. 08/393,074, filed Feb. 23, 1995, now U.S. Pat. No. 5,565,265, which is a continuation of Ser. No. 08/209,484, filed Mar. 14, 1994, now U.S. Pat. No. 5,559,225, which is a continuation of now abandoned Ser. No. 07/789,669, filed Nov. 8, 1991.

BACKGROUND OF THE INVENTION

1) Field of the Invention

This invention relates to 3-(substituted carbamoyloxy)-3-cephem derivatives, novel antibacterial compositions having excellent effects as drugs, and a process for their preparation.

2) Description of the Related Art

Japanese Patent Application Laid-Open (Kokai) No. 34794/1978 discloses unsubstituted or lower-alkyl-substituted 3-carbamoyloxy-3-cephem derivatives including the compounds represented by the following formula:

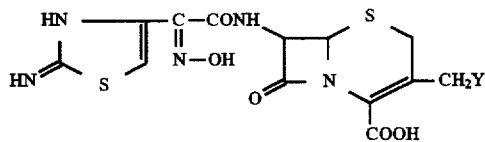

wherein Y means a hydrogen atom or a nucleophile compound residuum.

In addition, Japanese Patent Application No. 44714/1989 discloses the compounds represented by the following formula:

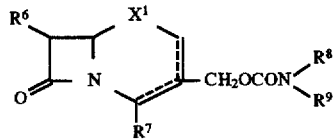

wherein $R^6$ means an amino group or an acylamino group, $R^7$ denotes a carboxyl group or a protected carboxyl group the group represented by the formula

represents a di(lower) alkylamino group, a (lower) alkylamino group, a saturated, 5- or 6-membered, heterocyclic (lower) alkylamino group containing 1–4 nitrogen atoms, said alkylamino group being optionally substituted by one or more lower alkyl groups, or a saturated, 5- or 6-membered heterocyclic group containing 2–4 nitrogen atoms, said heterocyclic group being optionally substituted by one or more lower alkyl or hydroxy(lower)alkyl groups, $X^1$ is

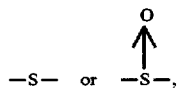

and the dotted line indicates a 2- or 3-cephem ring.

Further, Japanese Patent Publication No. 46474/1991 discloses cephem compounds represented by the following formula:

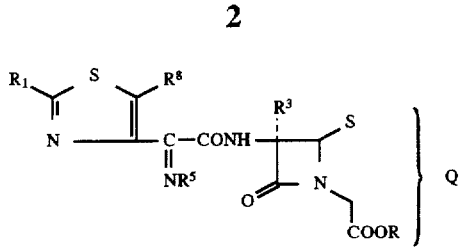

wherein $R^1$ is an amino or hydroxyl group which may optionally be protected, $R^3$ is a hydrogen atom, $R^5$ is a hydroxyl group or a substituted or unsubstituted alkoxyl group, $R^8$ is a hydrogen atom, Q denotes a carbon-carbon linkage for the formation of a 3-substituted-3-cephem-4-carboxylic acid, and R represents an ester residuum.

Several types of semisynthetic cephalosporins are now used for the treatment of various infectious diseases. None of them are, however, satisfactory as antibacterial agents which have strong antibacterial activities and, in particular, are orally-dosable.

SUMMARY OF THE INVENTION

An object of the present invention is therefore to provide an antibacterial composition which has strong antimicrobial activities and, moreover, is orally dosable.

As a result of an extensive investigation, the present inventors have found that certain novel 3-substituted carbamoyloxy-3-cephem derivatives have excellent antibacterial activities against various pathogenic fungi and their pharmacologically-protected derivatives are promptly absorbed through the digestive tract, form non-ester derivatives immediately after their absorption and are hence useful as antibacterial compositions for oral administration, leading to the completion of the present invention.

The present invention therefore provides a 7-acyl-3-substituted carbamoyloxy-3-cephem compound represented by the following formula (1), a pharmaceutically acceptable salt thereof, a preparation process thereof and an antibacterial composition and an intermediate comprising the same:

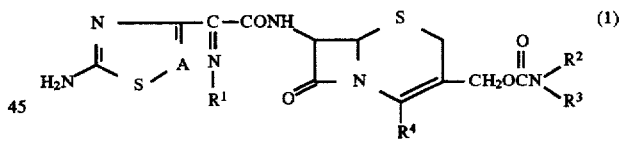 (1)

wherein A means a —CH= or —N= group; $R^1$ denotes a hydroxyl group, a lower alkoxyl group, a fluorine-substituted lower alkoxyl group or a hydroxyl group protected by a protecting group; $R^2$ and $R^3$ are the same or different and individually represent a lower alkyl group, a hydroxyl-substituted lower alkyl group, a carbamoyl-substituted lower alkyl group or a cyano-substituted lower alkyl group, $R^2$ is a hydrogen atom and $R^3$ is a lower alkoxyl group or a lower alkyl group which may optionally be substituted by one or more halogen atoms, or the group represented by the formula

means a 4–6 membered heterocyclic group, which contains one nitrogen atom, or a morpholino group, said heterocyclic group or morpholino group being optionally substituted by one or more lower alkyl, hydroxyl and/or hydroxyl-substituted lower alkyl groups; and $R^4$ denotes a carboxyl group or a carboxyl group protected by a protecting group, or a pharmaceutically acceptable salt thereof; its preparation process; an antibacterial composition comprising the compound or salt; and an intermediate for the compound.

The 7-acyl-3-substituted carbamoyloxy-3-cephem compound (1) and its pharmaceutically-acceptable salts have strong antibacterial activities and are orally dosable.

DETAILED DESCRIPTION OF THE INVENTION

In the above formula (1), examples of the lower alkoxyl group or fluorine-substituted lower alkoxyl group represented by $R^1$ include $C_{1-4}$ alkoxyl groups and fluorine-substituted $C_{1-4}$ alkoxyl groups, such as methoxy, ethoxy, propoxy, isopropoxy, butoxy, monofluoromethoxy, difluoromethoxy, 2-monofluoroethoxy, 2,2-difluoroethoxy, and 2,2,2-trifluoroethoxy.

The protecting group in "the protected hydroxyl group" represented by $R^1$ is an easily-removable hydroxyl-protecting group, including, for example, a protecting group removable under relatively mild conditions, such as formyl, acetyl, chloroacetyl, methoxyacetyl, phenoxyacetyl, benzoyl, ethoxycarbonyl, p-nitrophenoxycarbonyl, tetrahydropyranyl, tetrahydrothiofuranyl, trityl, methoxymethyl, ethoxymethyl, trimethylsilyl, t-butyldimethylsilyl or t-butyl. Of these, acetyl and trityl are preferred.

Illustrative of the lower alkyl, hydroxyl-substituted lower alkyl, carbamoyl-substituted lower alkyl and cyano-substituted lower alkyl groups represented by $R^2$ and $R^3$ in the formula (1) include methyl, ethyl, propyl, isopropyl, butyl, isobutyl, 2-hydroxyethyl, 3-hydroxypropyl, 2-hydroxypropyl, 3-hydroxybutyl, carbamoylmethyl, 2-carbamoylethyl, 3-carbamoylpropyl, 2-cyanoethyl, 3-cyanopropyl, and 2-cyanopropyl. The term "the lower alkyl group" as used in the definition for $R^3$ that "$R_2$ is a hydrogen atom and $R_3$ is a lower alkoxyl group or a lower alkyl group which may optionally be substituted by one or more halogen atoms" includes alkyl groups such as described above, with a methyl group and an ethyl group being preferred. The lower alkoxyl group is similar to that defined for $R^1$. Exemplary halogen atoms include fluorine, chlorine and iodine, with fluorine atom being preferred. The number of halogen atoms as substituents can range from 1 to 3.

On the other hand, examples of the 4–6 membered heterocyclic group, which contains one nitrogen atom, and morpholinyl group—said heterocyclic group and morpholinyl group being represented by the formula

and being optionally substituted—include the following groups:

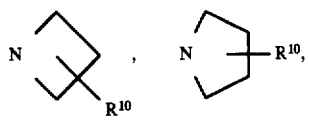

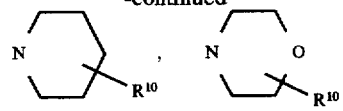

wherein $R^{10}$ represents a hydrogen atom or a lower alkyl, hydroxyl or hydroxyl-substituted lower alkyl group. Examples of the lower alkyl group include methyl, ethyl and propyl, while examples of the hydroxyl-substituted lower alkyl group include hydroxymethyl and 2-hydroxyethyl.

As the group

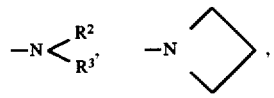

—$NHCH_3$ and —$N(CH_3)_2$ are preferred, with the last group being more preferred.

Illustrative of the protecting group for the carboxyl group represented by $R^4$ include lower alkyl groups such as methyl, ethyl and t-butyl;lower alkyl groups substituted by one or more substituted or unsubstituted phenyl groups such as p-methoxybenzyl, p-nitrobenzyl, 3,4-dimethoxybenzyl, diphenylmethyl, trityl or phenethyl; halogenated lower alkyl groups such as 2,2,2-trichloroethyl and 2-iodoethyl; lower-alkanoyloxy-lower-alkyl groups such as pivaloyloxymethyl, acetoxymethyl, propionyloxymethyl, butyryloxymethyl, valeryloxymethyl, 1-acetoxyethyl, 2-acetoxyethyl, 1-pivaloyloxyethyl and 2-pivaloyloxyethyl; higher-alkanoyloxy-lower-alkyl groups such as palmitoyloxyethyl, heptadecanoyloxymethyl and 1-palmitoyloxyethyl; lower-alkoxycarbonyloxy-lower-alkyl groups such as methoxycarbonyloxymethyl, 1-(butoxy-carbonyloxy)ethyl, 1-(t-butoxycarbonyloxy)ethyl, 1-(ethoxycarbonyloxy)ethyl and 1-(isopropoxycarbonyloxy)-ethyl; carboxy-lower-alkyl groups such as carboxymethyl and 2-carboxyethyl; heterocyclic groups such as 3-phthalidyl; benzoyloxy-lower-alkyl groups such as 4-glycidyloxybenzoyloxymethyl and 4-[N-(t-butoxycarbonyl) glycyloxy, benzoyloxymethyl, said benzoyloxy-lower-alkyl groups optionally containing one or more substituent groups; (substituted dioxolene)-lower-alkyl groups such as (5-methyl-2-oxo-1,3-dioxolen-4-yl)-methyl; cycloalkyl-substituted lower-alkanoyloxy-lower-alkyl groups such as 1-cyclohexylacetyloxyethyl; and cycloalkyloxycarbonyloxy-lower-alkyl groups such as 1-cyclohexyloxycarbonyloxyethyl.

In effect, any protecting group can be used as long as it can be removed by any means to form a carboxylic group. Preferred examples of the protecting group include 1-(isopropyloxycarbonyloxy)ethyl group, 1-(ethoxycarbonyloxy)ethyl group, 1-(cyclohexyloxycarbonyloxy)ethyl group, pivaloyloxymethyl group and isopropyloxycarbonyloxymethyl group, with 1-(isopropyloxycarbonyloxy)ethyl group being more preferred.

Further, illustrative of the pharmaceutically acceptable salt include alkali metal salts such as the sodium and potassium salts; the ammonium salt; quaternary ammonium salts such as the tetraethylammonium and betaine salts; alkaline earth metal salts such as the calcium and magnesium salts; inorganic acid salts such as the hydrochloride, hydrobromide, hydroiodide, sulfate, carbonate and bicarbonate; organic carboxylates such as the acetate, maleate, lactate and tartrate; organosulfonates such as the methanesulfonate, hydroxymethanesulfonate, hydroxyethanesulfonate, taurine salt, benzenesulfonate and toluenesulfonate; amino acid salts such as the arginine salt, lysine salt, serine salt, aspartate, glutamate and glycine salt; and amine salts such as the trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt and phenethylbenzylamine salt.

The compound of the present invention represented by the formula (1) can be prepared, for example, by the following processes:

PREPARATION EXAMPLE 1

The compound represented by the formula (1) or a salt thereof can be obtained by reacting a compound represented by the following formula:

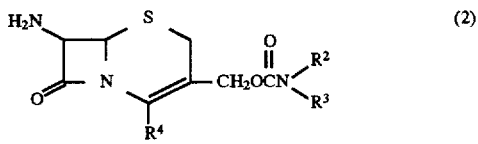

wherein $R^2$, $R^3$ and $R^4$ have the same meanings as defined above or a salt thereof, with a compound represented by the following formula (3):

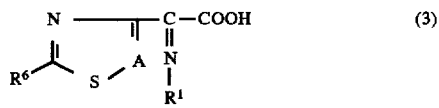

wherein A and $R^1$ have the same meanings as defined above, and $R^6$ represents an amino group or an amino group protected by a protecting group, or a reactive acid derivative thereof or a salt thereof, and if necessary, removing the protecting group of the amino, carboxyl or hydroxyl group or protecting the carboxyl group with a protecting group.

Examples of the amino-protecting group represented by $R^6$ include carbamoyl groups, aliphatic acyl groups, aromatic-ring-containing or heterocyclicring-containing acyl groups, sulfonyl groups and benzilidene groups.

Illustrative of the acyl group and the sulfonyl group include alkanoyl groups such as formyl, acetyl, propionyl, butyryl, isobutyryl, valeryl, isovaleryl, oxalyl, succinyl and pivaloyl; alkoxycarbonyl groups such as methoxycarbonyl, ethoxycarbonyl,-propoxycarbonyl, 1-cyclopropylethoxycarbonyl, isopropoxycarbonyl, butoxycarbonyl, tert-butoxycarbonyl, pentyloxycarbonyl, tert-pentyloxycarbonyl and hexyloxycarbonyl; aralkoxycarbonyl groups such as benzyloxycarbonyl and phenethyloxycarbonyl; alkanesulfonyl groups such as mesyl, ethanesulfonyl, propanesulfonyl, isopropanesulfonyl and butanesulfonyl; arenesulfonyl groups such as benzenesulfonyl and toluenesulfonyl; aroyl groups such as benzoyl, toluoyl, naphthoyl, phthaloyl and indanecarbonyl; aralkanoyl groups such as phenylacetyl and phenylpropionyl; aryloxyalkanoyl groups such as phenoxyacetyl and phenoxypropionyl; heterocyclic carbonyl groups such as furoyl, thenoyl and nicotinoyl; heterocyclic glyoxyloyl such as thienylglyoxyloyl and thiazolylglyoxyloyl; and heterocyclic alkanoyl groups such as thienyl and thiazolylacetyl. These groups may contain one or more suitable substituents, for example, halogens such as chlorine, bromine, iodine and fluorine; nitro groups; amino groups; alkanoylamino groups such as formylamino and acetylamino groups; cyano groups; alkyl groups such as methyl, ethyl, propyl, isopropyl and butyl; alkenyl groups such as vinyl and allyl; and groups represented by the formula $=N-OR_5$ wherein $R_5$ means a hydrogen atom; an alkyl group such as methyl, ethyl, propyl, isopropyl, butyl, pentyl or hexyl; an alkenyl group such as vinyl or propenyl; or an alkynyl group such as ethynyl or propynyl.

Illustrative of the benzylidene group includes benzylidene group, p-nitrobenzylidene group, m-nitrobenzylidene group, 3,4-methylenedioxybenzylidene group and m-chlorbenzylidene group.

The compound (3) may be reacted in the presence of a condensing agent [a carbodiimide (N,N'-dicyclohexylcarbodiimide or the like), a carbonyl compound (carbonyldiimidazole or the like), an isoxazolium salt, or an acylamino compound (2-ethoxy-1-ethoxycarbonyl-1,2-dihydroxyquinoline or the like)]. Usable examples of its reactive acid derivative include acid anhydrides [symmetric acid anhydrides, mixed acid anhydrides (mixed acid anhydrides of mineral acids (phosphoric acid, sulfuric acid, carbonate half-esters or the like) and organic acids (alkanoic acids, aralkanoic acids, sulfonic acids or the like), etc.], acid halides, active esters [esters with N-hydroxy compounds (esters with N-hydroxysuccinimide or N-hydrophtalimide)], thiol esters (aralkylthiol esters, heterocyclic thiol esters, etc.), and aryl esters (phenyl ester, halophenyl esters, nitrophenyl esters, etc.).

The above reaction can be conducted at a reaction temperature of from −50° C. to +50° C. in an inert solvent such as dichloromethane, chloroform, tetrahydrofuran, acetone, ethyl acetate, methanol, ethanol, dimethylsulfoxide, N,N-dimethylformamide, benzene, toluene or hexane.

The removal of each protecting group, the protection of a carboxyl group with a protecting group and the salt-forming reaction can be performed by methods known per se in the art.

The deprotection of the protected carboxyl group can be effected by hydrolysis in the presence of an acid. Here, preferred examples of the acid include inorganic acids such as hydrochloric acid, hydrobromic acid and sulfuric acid; organic acids such as formic acid, acetic acid, trifluoroacetic acid, methanesulfonic acid and p-toluenesulfonic acid; and Lewis acids such as boron trifluoride, aluminum trichloride, stannic chloride, ferric chloride, titanium tetrachloride an zinc chloride. It is preferred to conduct the reaction in the presence of a cation scavenger such as anisole, if necessary.

The hydrolysis is generally conducted in an inert solvent such as water, methanol, ethanol, propanol, tetrahydrofuran, N,N-dimethylformamide, dioxane or methylene chloride, or in a mixed solvent of two or more of such inert solvents. The acids exemplified above can be used as a solvent. Although the reaction can be conducted generally at −78° C. to 80° C., it is preferred to conduct it at a temperature ranging from ice cooling to room temperature.

When $R^4$ represents a carboxyl group or a salt thereof, the protection may be conducted by a method known per se in the art. For instance, esterification can be performed by the reaction with an alcohol-reactive derivative after optional conversion into an alkali metal salt or an organic amine salt.

The conversion into the alkali metal salt is carried out using an alkali metal salt of an organic acid such as sodium acetate, potassium acetate, sodium 2-ethylhexanonate, potassium 2-ethylhexanonate; an alkali metal hydroxide such as sodium hydroxide or potassium hydroxide; or an alkali metal carbonate such as sodium carbonate, potassium carbonate or sodium hydrogencarbonate; or the like. The conversion into the organic amine salt can be carried out using trimethylamine, triethylamine, dichlorohexylamine or pyridine.

The reaction is generally conducted in an inert solvent such as water, methanol, ethanol, propanol, tetrahydrofuran, N,N-dimethylformamide, dioxane, methylene chloride, ethyl acetate, methyl acetate or acetonitrile or in a mixed solvent of two or more of such inert solvents.

The reaction with the alcohol-reactive derivative is generally conducted in an inert solvent such as water, methanol, ethanol, propanol, N,N-dimethyl-formamide, N,N-dimethylacetamide, acetone, tetrahydrofuran, dioxane, methylene chloride, ethyl acetate, methyl acetate, acetonitrile, benzene or toluene; or in a mixed solvent of two or more of such inert solvents. The reaction can be conducted generally at −78° C. to 80° C., but preferably at a temperature ranging from ice cooling to room temperature.

The removal of the protecting group from the protected amino group can be conducted in the presence of an acid according to a common method. Preferred examples of the acid include inorganic acids such as hydrochloric acid, hydrobromic acid and sulfuric acid; and organic acids such as formic acid, acetic acid, trifluoroacetic acid, methanesulfonic acid and p-toluenesulfonic acid.

The reaction is conducted generally in an inert solvent such as water, methanol, ethanol, propanol, N,N-dimethylformamide, N,N-dimethylacetamide, acetone, tetrahydrofuran, dioxane or methylene chloride; or in a mixed solvent of two or more of such inert solvents. The reaction can be conducted generally at −50° C. to 50° C., but preferably at a temperature ranging from ice cooling to room temperature.

Preparation Process 2

The compound represented by the following formula (5):

wherein $R^2$, $R^3$, $R^4$ and $$-N{<}^{R^2}_{R^3}$$

have the same meanings as defined above or a salt thereof can be obtained by reacting the compound represented by the following formula (4):

wherein $R^2$, $R^3$, $R^4$ and $$-N{<}^{R^2}_{R^3}$$

have the same meanings as defined above and X represents a halogen atom or a salt thereof with thiourea, and, if necessary, removing the protecting group of the carboxyl group or protecting the carboxyl group with a protecting group.

The reaction is generally conducted in an inert solvent such as water, methanol, ethanol, propanol, N,N-dimethylformamide, N,N-dimethylacetamide, formic acid, acetic acid, acetone, tetrahydrofuran, dioxane, methylene chloride, ethyl acetate, methyl acetate, acetonitrile, benzene or toluene; or in a mixed solvent of two or more of such inert solvents. The reaction can be conducted generally at −78° C. to 80° C., but preferably at a temperature ranging from ice cooling to room temperature.

Preparation Process 3

N,N'-carbonyldiimidazole is reacted with a compound represented by the following formula:

wherein $R^1$ $R^4$ and $R^6$ have the same meanings as defined above, or a salt thereof to convert the former to a reactive derivative. The reactive derivative is reacted further with a compound represented by the formula:

$$HN{<}^{R^2}_{R^3}$$

wherein $R^2$, $R^3$ and $$-N{<}^{R^2}_{R^3}$$

have the same meanings as defined above, or a salt thereof. If necessary, any protecting groups of the amino, hydroxyl and carboxyl group are removed by a method known per se in the art and further, the carboxyl group is protected by a protecting group, thereby obtaining a compound represented by the formula (1) or a salt thereof. Removal of each protecting group can be conducted by a method known per se in the art, said method having been described in Preparation Process 1.

In the above Preparation Processes 1–3 for the compounds of the present invention, the target compounds, (1) and (5) can each be obtained by conducting the reaction by using the sulfoxide derivative of the corresponding cephem ring instead of the starting compound (2), (4) or (11).

Next, intermediates useful in the preparation of the compounds of the present invention can be prepared, for example, by the processes to be described below.

a) Preparation Process A

A compound represented by the following formula:

wherein $R^2$ $R^3$ $R^4$ and $$-N{<}^{R^2}_{R^3}$$

have the same meanings as defined above $R^5$ represents an amino or protected amino group, or a salt thereof can be prepared by reacting a compound represented by the following formula (9):

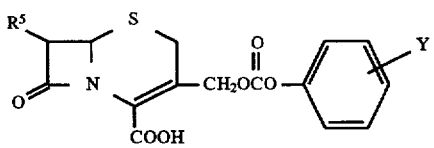

wherein Y is a hydrogen atom, a lower alkyl group, a halogen atom or a nitro group, said Y being optionally substituted by one to five of these groups which may be the same or different, and $R^5$ has the same meanings as described above or a salt thereof with a compound represented by the following formula:

wherein $R^2$, $R^3$ and

have the same meanings as defined above, or a salt thereof in an inert solvent and, if necessary, protecting the carboxyl group.

The reaction is conducted generally in an inert solvent such as water, methanol, ethanol, propanol, acetone, methyl ethyl ketone, tetrahydrofuran, dioxane, acetonitrile, N,N-dimethylformamide, N,N-dimethylacetamide, benzene, methylene chloride or chloroform; or in a mixed solvent of two or more of such inert solvents.

Although the reaction can be conducted generally at −78° C. to 80° C., it is preferred to conduct it at a temperature ranging from ice cooling to room temperature. As the reaction time, it is generally sufficient to conduct the reaction for only 10 minutes to 1 hour.

Examples of the amino-protecting group represented by $R^5$ are similar to those of the amino-protecting group represented by $R^6$.

The compound prepared by this process can be utilized as an intermediate for the compound of the present invention represented by the formula (1) by removing the amino-protecting group or protecting the carboxyl group with a protecting group as needed. The removal of the amino-protecting group or the protection of the carboxyl group can be carried out by the method known per se in the art, said method having been described in Preparation Process 1.

b) Preparation Process B

A compound represented by the following formula (7):

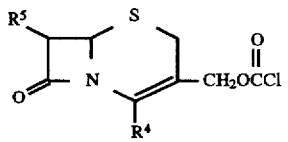

wherein $R^4$ and $R^5$ have the same meanings as defined above is prepared by reacting a compound represented by the following formula (12):

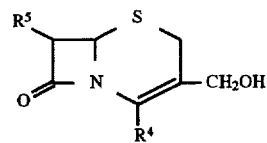

wherein $R^4$ and $R^5$ have the same meanings as defined above or a salt thereof, with phosgene or a phosgene derivative in the presence of a base. Then, the resulting compound is reacted with a compound represented by the following formula:

wherein $R^2$ and $R^3$ have the same meanings as defined above or a salt thereof, thereby obtaining a compound represented by the following formula (8):

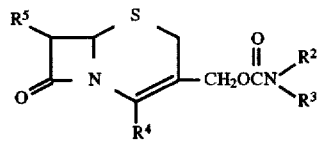

wherein $R^2$, $R^3$, $R^4$, $R^5$ and

have the same meanings as defined above.

Suitable examples of the base in the above reaction include the hydroxides or carbonates of alkali metals or alkaline earth metals, such as sodium hydroxide, potassium hydroxide, barium hydroxide, magnesium hydroxide, sodium carbonate, sodium hydrogencarbonate, potassium carbonate; tertiary amines such as triethylamine, tributylamine, N-methylmorpholine, pyridine, toluidine, lutidine, and N,N-dimethylaminopyridine.

Examples of the phosgene derivative include trichloromethylchloroformate and bis(trichloromethyl)-carbonate.

The reaction is conducted generally in an inert solvent such as N,N-dimethylformamide, acetone, acetonitrile, tetrahydrofuran, dichloromethane, chloroform or ethyl acetate; or in a mixed solvent of two or more of such inert solvents. The reaction can be conducted generally at −100° C. to 30° C., but preferably at a temperature ranging from −78° C. to 0° C.

Compounds prepared by this process can be utilized as intermediates for the compounds of the present invention represented by the formula (1) by removing the amino-protecting group or protecting the carboxyl group with a protecting group as needed. Their removal or protection can be carried out by a method known per se in the art, said method having been described in Preparation Process 1.

c) Preparation Process C

N,N'-carbonyldiimidazole is reacted with a compound represented by the following formula (13)

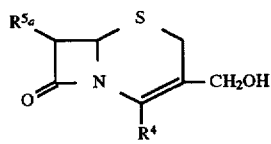
(13)

wherein $R^4$ has the same meaning as defined above and $R^5a$ represents a protected amino group or with a salt thereof to convert the latter to an active derivative. The active derivative is reacted further with a compound represented by the formula:

wherein $R^2$ $R^3$ and

have the same meanings as defined above, or a salt thereof. If necessary, the amino group may be deprotected, thereby obtaining a compound represented by the following formula (8):

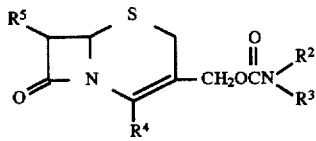
(8)

wherein $R^2$, $R^3$, $R^4$, $R^5$ and

have the same meanings as described above.

The reaction is conducted generally in an inert solvent such as water, methanol, ethanol, propanol, acetone, methyl ethyl ketone, tetrahydrofuran, dioxane, acetonitrile, N,N-dimethylformamide, N,N-dimethylacetamide, benzene, methylene chloride or chloroform; or in a mixed solvent of two or more of such inert solvents.

Compound prepared by this process can be utilized as intermediates for the compounds of the present invention represented by the formula (1) by removing any amino- and/or carboxyl-protecting group or protecting the carboxyl group with a protecting group as needed. The deprotection can be carried out by the method known per se in the art, said method having been described in Preparation Process 1.

d) Preparation Process D

A compound represented by the following formula (14):

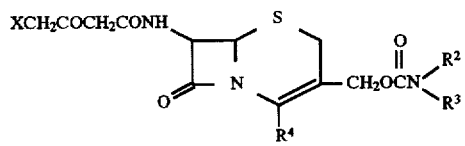
(14)

wherein $R^2$, $R^3$, $R^4$ and

have the same meanings as defined above and X represents a halogen atom can be prepared by reacting the compound represented by the formula (2) or a salt thereof with a compound represented by the following formula:

$$XCH_2COCH_2COOH$$

wherein X has the same meaning as defined above, or with a salt or carboxyl-reactive derivative thereof.

Illustrative of the reactive derivative include acid halides such as the acid chloride and acid bromide. These acid halides can each be obtained by reaction with its corresponding diketene and halogen.

The reaction is conducted generally in an inert solvent such as water, methanol, ethanol, propanol, N,N-dimethylformamide, N,N-dimethylacetamide, acetone, tetrahydrofuran, dioxane, methylene chloride, ethyl acetate, methyl acetate, acetonitrile, benzene, toluene or pyridine; or in a mixed solvent of two or more of such inert solvents. The reaction can be conducted generally at –78° C. to 80° C., but preferably at a temperature ranging from ice cooling to room temperature.

The compound represented by the following formula (4):

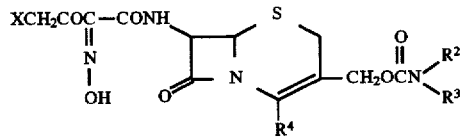
(4)

wherein $R^2$, $R^3$, $R^4$, X and

have the same meanings as defined above or a salt thereof can be prepared by reacting a nitrosating agent with the compound represented by the formula (14) or its salt.

Examples of the nitrosating agent include nitrous acid and its derivatives, for example, alkali metal nitrites such as sodium nitrite and potassium nitrite; and alkyl nitrites such as butyl nitrite, pentyl nitrite and amyl nitrite. When an alkali metal nitrite such as sodium nitrite or potassium nitrite is used, it is preferred to conduct the nitrosation in the presence of an inorganic or organic acid such as hydrochloric acid, sulfuric acid, formic acid or acetic acid.

The reaction is carried out generally in an inert solvent such as water, methanol, ethanol, propanol, N,N-dimethylformamide, acetone, tetrahydrofuran, dioxane or methylene chloride; or in a mixed solvent of two or more of such inert solvents. The reaction can be conducted generally at –78° C. to 80° C., but preferably at a temperature ranging from ice cooling to room temperature.

e) Preparation Process E

A compound represented by the following formula (17):

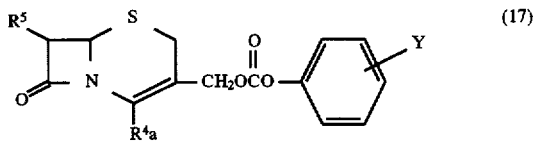

wherein $R^4a$ represents a protected carboxyl group, $R^5$ and Y have the same meanings as defined above, or a salt thereof can be obtained at a high yield by reacting, in the presence of a base, a compound represented by the following formula (15):

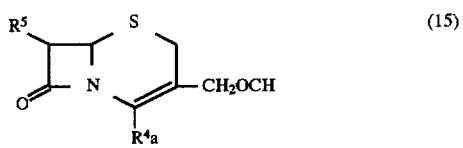

wherein $R^4a$ and $R^5$ have the same meanings as defined above or a salt thereof, with a compound represented by the following formula (16):

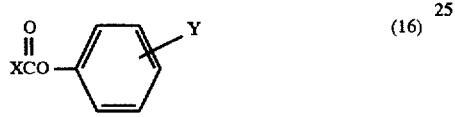

wherein X and Y have the same meanings as defined above.

In the next place, the carboxyl-protecting group is removed from the resulting compound, thereby obtaining the compound represented by the following formula (9):

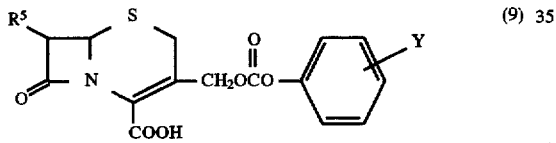

wherein $R^5$ and Y have the same meanings as defined above or a salt thereof. Removal of carboxyl-protecting group is carried out by the method described in Preparation Process 1.

Examples of the above-described salt of the compound represented by the formula (15) include alkali metal salts (sodium salt, potassium salt, etc.), alkaline earth metal salts (calcium salt, magnesium salt, etc.), ammonium salt, organic amine salts (trimethylamine salt, triethylamine salt, etc.), organic acid salts (formate, trifluoroacetate, toluenesulfonate, etc.), and inorganic acid salts (hydrochloride, sulfate, etc.).

Suitable examples of the base include alkali metal salts and alkaline earth metal salts, such as sodium hydroxide, potassium hydroxide, barium hydroxide, magnesium hydroxide, sodium carbonate, potassium carbonate, sodium hydrogencarbonate, potassium hydrogencarbonate; alkali metal or alkaline earth metal salts of organic acids, such as sodium acetate, potassium acetate, barium acetate and magnesium acetate; and tertiary amines such as triethylymine, tributylamine, N-methylmorpholine, pyridine, toluidine, lutidine, and N,N-dimethylaminopyridine.

The reaction is usually conducted in an inert solvent such as N,N-dimethylformamide, acetone, acetonitrile, tetrahydrofuran, dioxane, dichloromethane, chloroform, ethyl acetate, methyl acetate, benzene, toluene or hexane, or in a mixed solvent of two or more of such inert solvents.

Although the reaction can be conducted generally at −78° C. to 80° C., it is preferred to conduct it at a temperature ranging from ice cooling to room temperature.

In Preparation Processes A–E for intermediate compounds, the target compounds (4), (8) and (9) can also be obtained by using, instead of the starting compound (9), (12), (13), (14) and (15), their sulfoxido derivatives and then conducting reduction after the reactions.

Out of the intermediates described above, the compounds represented by the following formula (6):

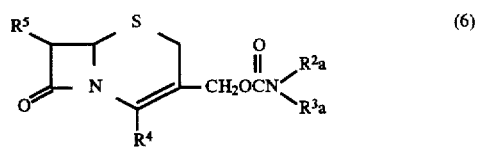

wherein $R^2a$ and $R^3a$ are the same or different and individually represent a lower alkyl group, a hydroxyl-substituted lower alkyl group or a cyano-substituted lower alkyl group or the group represented by the formula

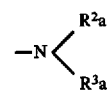

means a 4–6 membered heterocyclic group, which contains one nitrogen atom, or a morpholino group, said heterocyclic group or morpholino group being optionally substituted by one or more lower alkyl, hydroxyl, hydroxyl-substituted lower alkyl groups, $R^4$ denotes a carboxyl group or a carboxyl group protected by a protecting group, and $R^5$ represents an amino or protected amino group, the compounds represented by the formula (4) and the compounds represented by the formula (9) are all novel compounds.

To demonstrate the efficacy of the compounds according to the present invention, the minimum inhibitory concentrations (MIC) of certain representative compounds obtained in examples, which will follow, against various fungi and their excretion rates in urine upon oral administration were measured, and an in vivo experiment for the treatment of respiratory-infected model mice was conducted using such representative compounds.

a) The results of the measurement of MICs against the various fungi are shown in Table 1.

TABLE 1

| Test compound | MIC (g/ml) | | | | | |
|---|---|---|---|---|---|---|
| | Staphylococcus aureus 209-P | Escherichia coli NIHJ | Klebsiella pneumoniae IID875 | Serratia marcescens IID620 | Morganella morganii IID601 | Haemophilus influenzae IID1638 |
| Example 1 | 0.2 | 0.1 | 0.05 | 0.05 | 0.025 | 0.1 |

TABLE 1-continued

| Test compound | MIC (g/ml) | | | | | |
|---|---|---|---|---|---|---|
| | Staphylococcus aureus 209-P | Escherichia coli NIHJ | Klebsiella pneumoniae IID875 | Serratia marcescens IID620 | Morganella morganii IID601 | Haemophilus influenzae IID1638 |
| Example 2 | 0.2 | 0.4 | 0.2 | 0.2 | 0.05 | 0.1 |
| Example 4 | 0.8 | 0.2 | 0.1 | 0.025 | 0.025 | 0.012 |
| Example 6 | 0.8 | 0.2 | 0.2 | 0.025 | 0.012 | 0.012 |
| Example 8 | 0.2 | 0.1 | 0.1 | 0.05 | 0.025 | 0.1 |
| Example 9 | 0.2 | 0.05 | 0.05 | 0.05 | 0.025 | 0.1 |
| Example 38 | 0.1 | 0.025 | 0.025 | 0.05 | 0.05 | 0.2 |
| Example 39 | 0.2 | 0.05 | 0.025 | 0.05 | 0.05 | 0.2 |
| Example 40 | 0.2 | 0.05 | 0.05 | 0.1 | 0.05 | 0.2 |
| Example 41 | 0.2 | 0.2 | 0.2 | 0.1 | 0.1 | 0.2 |
| Compound A | 0.1 | 0.05 | 0.025 | 0.05 | 0.05 | 0.4 |

Compound A in Table 1 is the following compound.
Compound A:

7-[(Z)-2-(2-Aminothiazol-4-yl)-2-hydroxyiminoacetamido]-3-carbamoyloxymethyl-3-cephem-4-carboxylic acid.

As apparent from Table 1, the compounds according to the present invention have excellent antibacterial activities and are useful especially as those having strong antibacterial activities against Haemophilus influenzae.

b) Bioavailability

Certain representative compounds according to the present invention were each suspended in a CMC-Na solution. The resulting suspension was administered orally to mice at the dosage of 20 mg/kg. Urea excreted during 6 hours after the administration was collected. The excreteion rate in urea and bioavailability measured are shown in Table 2.

TABLE 2

| Compound | Bioavailability by oral administration | |
|---|---|---|
| | Bioavailability (%) | Recovery in urea (%) |
| Compound B | 17 | 11.0 |
| Compound C | 7 | 4.5 |
| Compound D | 17 | 10.4 |
| Example 14 | 38 | 18.2 |
| Example 20 | 46 | 22.0 |
| Example 24 | 34 | 20.0 |

Compounds B, C. and D in Table 2 are as follows:
Compound B:

Pivaloyloxymethyl 7-[(Z)-2-(2-aminothiazol-4-yl)-2-hydroxyiminoacetamido]-3-carbamoyloxymethyl-3-cephem-4-carboxylate.

Compound C:

1-(Isopropyloxycarbonyloxy)ethyl 7-[(Z)-2-(2-aminothiazol-4-yl)-2-hydroxyiminoacetamido]-3-carbamoyloxymethyl-3-cephem-4-carboxylate.

Compound D:

Pivaloyloxymethyl 7-[(Z)-2-(2-aminothiazol-4-yl)-2-methoxyiminoacetamido]-3-carbamoyloxymethyl-3-cephem- 4-carboxylate.

c) Treatment results of respiratory-infected mice

A bacterium-containing solution was inoculated into the nasal cavity of each mouse, followed by the oral administration of a suspension of one of the compounds in a CMC-Na solution one hour later where the bacterium was Haemophilus influenzae but four hours later where the bacterium was Klebsiella pneumoniae. The number of intrapulmonary viable cells of the bacterium was counted upon an elapsed time of 24 hours after the infection. The measurement limit is represented by the following formula.

Log CFU/Lung=1.48 wherein CFU is the colony forming unit.

When no colony was observed, the bacterium was regarded as having been eradicated and Log CFU/Lung was calculated to be 1. The results are shown in Tables 3 and 4.

TABLE 3

Klebsiella pneumoniae E02033, Inoculum size: 1.4 × 10³ CFU/mouse

| Compound | MIC (μg/ml) | Dosage (mg/kg) | Intrapulmonary viable cells (log CFU/lung) | Eradication rate (%) |
|---|---|---|---|---|
| Example 20 | 0.1 | 10 | 1.66 ± 1.02 | 50 |
| Compound E | 0.2 | 10 | 4.26 ± 0.62 | 0 |
| Compound F | 0.2 | 10 | 6.25 ± 0.74 | 0 |
| Control | — | — | 7.31 ± 0.73 | 0 |

Compounds E and F in Table 3 are as follows:
Compound E:

1-(Isopropyloxycarbonyloxy)ethyl 7-[(Z)-2-(2-aminothiazol-4-yl)-2-methoxyiminoacetamido]-3-methoxymethyl-3-cephem-4-carboxylate.

Compound F:

7-[(Z)-2-(2-aminothiazol-4-yl)-2-hydroxyiminoacetamido]-3-vinyl-3-cephem-4-carboxylic acid.

TABLE 4

Haemophilus influenzae E35147, Inoculum size: 4.3 × 10⁵ CFU/mouse

| Compound | MIC (μg/ml) | Dosage (mg/kg) | Intrapulmonary viable cells (Log CFU/Lung) |
|---|---|---|---|
| Example 20 | 0.1 | 40 | 3.51 ± 0.37 |
| Example 43 | 0.2 | 40 | 4.86 ± 0.60 |
| Compound C | 0.8 | 40 | 5.50 ± 0.61 |
| Compound F | 0.8 | 40 | 5.16 ± 0.73 |
| Control | — | — | 5.73 ± 0.58 |

Compound C. in Table 4 is the same as that in Table 2 and Compound F in Table 4 is the same as that in Table 3.

As is envisaged from the above tables, the compounds according to the present invention have properties as excellent orally antibacterial agents.

The acute toxicity, $LD_{50}$(mouse, p.o.), of the compounds according to the present invention were all 2 g/kg or greater.

To use the compounds of the present invention as antibacterial compositions, they can be administered orally or parenterally in 1–4 portions at a total daily dosage of 100 mg to 5 g in general. The dosage varies depending on the age and conditions.

Dosable preparation forms include tablets, granules, powders, capsules, syrups, liquids, etc. Each of these preparations can be formulated in a manner known per se in the art, by adding a known excipient.

Examples will next be set out to describe the present invention in further detail. It is, however, to be noted that the present invention is not limited by the following examples.

Starting materials employed upon preparation of the compounds of the present invention will be described as preparation examples.

Throughout the examples, "Tr" stands for a $(C_6H_5)_3C-$ group, "BH" for a $(C_6H_5)_2CH-$ group, and Me for a methyl group.

PREPARATION EXAMPLE 1

Benzhydryl 7-thienylacetamido-3-N,N-dimethyl-carbamoyloxymethyl-3-cephem-4-carboxylate-1-oxide

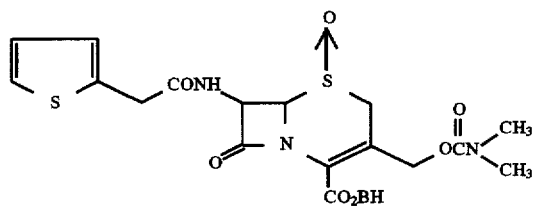

A solution of benzhydryl 7-thienylacetamido-3-hydroxymethyl-3-cephem-4-carboxylate (30 g; 0.058 mol) in tetrahydrofuran (600 ml) was stirred under ice cooling, to which N,N'-carbonyldiimidazole (11.25 g; 0.069 mol) was added, followed by stirring under ice cooling for further three hours. The reaction mixture was added with ethyl acetate (1 l), and the resulting mixture was washed with water (400 ml). The organic layer was stirred under ice cooling, followed by the addition of a 50% aqueous dimethylamine solution (12 g; 0.075 mol). They were reacted for one hour. The reaction mixture was dried over anhydrous magnesium sulfate and then concentrated, whereby a mixture of benzhydryl 7-thienylacetamido-3-N,N-dimethylcarbamoyloxymethyl-3-cephem-4-carboxylate and benzhydryl 7-thienylacetamido-3-N,N-dimethylcarbamoyloxymethyl-2-cephem-4-carboxylate was obtained (24 g).

To a solution of the resulting mixture in tetrahydrofuran (400 ml), a solution of m-chloroperbenzoic acid (20 g; 0.116 mol) in tetrahydrofuran (100 ml) was added in portions, followed by stirring for one and a half hours under ice cooling. The reaction mixture was concentrated under reduced pressure and the residue was washed with ether. After further concentration under reduced pressure, the residue was purified by chromatography on a silica gel column, whereby the title compound was obtained (7.5 g; yield: 21%).

NMR (CDCl$_3$, δ): 2.84(3H,s), 2.92(3H,s), 3.23,3.88(2H, ABq,J=18 Hz), 3.88(2H,s), 4.48(2H,d,J=4 Hz), 4.78,5.34 (2H,ABq, J=8 Hz), 6.15(1H,dd,J=4 Hz,8 Hz), 6.90–7.10 (2H,m), 6.97(1H,s), 7.2–7.6(11H,m)

PREPARATION EXAMPLE 2

Benzhydryl 7-thienylacetamido-3-N,N-dimethylcarbamoyloxymethyl-3-cephem-4-carboxylate

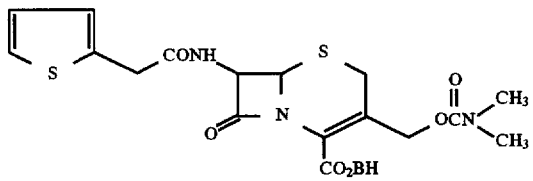

A solution of benzhydryl 7-thienylacetamido-3-N,N-dimethylcarbamoyloxymethyl-3-cephem-4-carboxylate-1-oxide (5 g; 8.2 mmol), which had been obtained in Preparation Example 1, in N,N-dimethylformamide (50 ml) was stirred under ice cooling, followed by the addition of phosphorus trichloride (2.5 g; 18 mmol). The resulting solution was stirred for 30 minutes and added with ethyl acetate (500 ml). The resulting mixture was washed with water and a saturated aqueous sodium chloride solution and thereafter added with anhydrous magnesium sulfate. After the organic layer was concentrated under reduced pressure, the residue was solidified from a mixed solvent of acetone and isopropyl ether. The resulting solid was collected by filtration, whereby the title compound was obtained (3.8 g; yield: 79%).

NMR (CDCl$_3$, δ): 2.82(3H,s), 2.90(3H,s), 3.40,3.55(2H, ABq,J=18 Hz), 3.84 (2H,s), 4.81,5.06(2H,ABq,J=12 Hz), 4.98 (1H,d, J=4 Hz), 5.84(1H,dd,J=4 Hz,8 Hz), 6.27(1H,d, J=8 Hz), 6.94(1H,s), 6.98–7.02(2H,m), 7.25–7.43(11H,m)

PREPARATION EXAMPLE 3

Benzhydryl 7-amino-3-N,N-dimethylcarbamoyloxymethyl-3-cephem-4-carboxylate hydrochloride

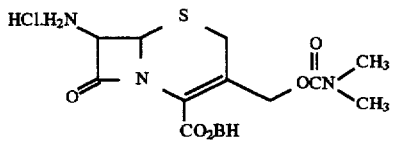

A solution of phosphorus pentachloride (2.8 g; 13 mmol) and pyridine (1.04 g; 13 mmol) in methylene chloride (80 ml) was cooled to −10° C. To the resulting solution, benzhydryl 7-thienylacetamido-3-N,N-dimethylcarbamoyloxymethyl-3-cephem-4-carboxylate (1.6 g; 2.7 mmol), which had been obtained in Preparation Example 2, was added, followed by stirring at −10° C. for one hour. The resulting solution was cooled down to −20° C. and then added with 1,3-propanediol (1 ml). They were stirred at −20° C. for one hour. The reaction mixture was added with methanol (10 ml), and the resulting mixture was heated to the room temperature and thereafter washed with water (50 ml) added. The organic layer was dried over anhydrous magnesium sulfate. After concentration under reduced pressure, the residue was solidified with ether and isopropyl ether, whereby the title compound was obtained (1.0 g; yield: 74%).

NMR (CDCl$_3$, δ): 2.83(3H,s), 2.90(3H,s), 3.43,3.58(2H, ABq,J=18 Hz), 4.80,5.06(2H,ABq,J=12 Hz), 4.8(1H,m), 4.97(1H,d, J=4 Hz), 6.98(1H,s), 7.25–7.50(10H,m)

Ethyl acetate was dissolved in the hydrochloride (1.0 g) which had been obtained in the above step. The resulting solution was added with an aqueous solution of sodium hydrocarbonate to neutralize the solution. The organic layer was washed with water and then with a saturated aqueous sodium chloride solution, followed by drying over anhydrous magnesium sulfate and concentration under reduced pressure, whereby benzhydryl 7-amino-3-N,N-dimethylcarbamoyloxymethyl-3-cephem-4-carboxylate (0.9 g) was obtained.

PREPARATION EXAMPLE 4

Benzhydryl 7-[(Z)-2-(2-tritylaminothiazol-4-yl)-2-trityloxyiminoacetamido]-3-N,N-dimethylcarbamoyloxymethy-3-cephem-4-carboxylate

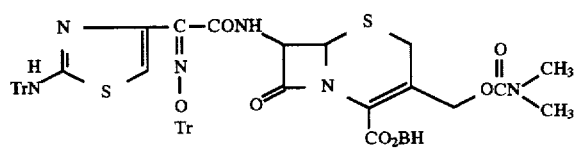

A solution of (Z)-2-(2-tritylaminothiazol-4-yl)-2-trityloxyiminoacetic acid (1.9 g; 2.8 mmol), 1-hydroxy-1H-benztriazole (0.4 g; 2.9 mmol) and dicyclohexylcarbodiimide (0.6 g; 2.9 mmol) in dimethylformamide (20 ml) was stirred at room temperature for 30 minutes. To the resulting solution, benzhydryl 7-amino-3-N,N-dimethylcarbamoyloxymethyl-3-cephem-4-carboxylate (1.3 g; 2.8 mmol), which had been obtained in the second step of Preparation Example 3, was added, followed by stirring for 3 hours. The reaction mixture was added with ethyl acetate (300 ml) and the resulting mixture was washed with water and a saturated aqueous sodium chloride solution, followed by drying over anhydrous magnesium sulfate. After concentration under reduced pressure, the concentrate was subjected to chromatography on a silica gel column, whereby the title compound was obtained (1.4 g; yield: 45%).

NMR (CDCl$_3$, δ): 2.82(3H,s), 2.91(3H,s), 3.36,3.48 (2H, ABq,J=18 Hz), 4.81,5.14(2H,ABq,J=12 Hz), 5.05(1H,d,J=4 Hz), 6.08(1H,dd,J=4 Hz,8 Hz), 6.43(1H,s), 6.80(1H,s), 6.97 (1H,s), 7.18–7.50(42H,m)

PREPARATION EXAMPLE 5

Benzhydryl 7-thienylacetamido-3-N-ethyl-N-methyl-carbamoyloxymethyl-3-cephem-4-carboxylate-1-oxide

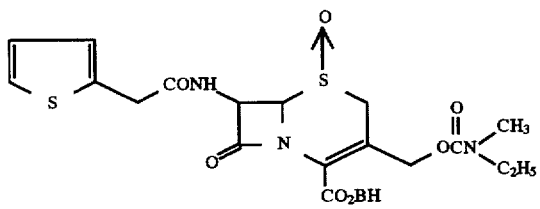

In a similar manner to Preparation Example 1, the title compound was obtained (yield: 9%).

NMR (CDCl$_3$, δ): 1.0–1.18(3H,m), 3.80(½H,s), 3.86 (½H,s), 3.18–3.5(3H,m), 3.80–3.90(2H,m), 3.85(2H,s), 4.44–4.46(1H,m), 4.74(1H,d,J=13 Hz), 5.24–5.38(1H,m), 6.07(1H,dd,J=5 Hz,8 Hz), 6.9–7.02(4H,m), 7.23–7.50(11H,m)

PREPARATION EXAMPLE 6

Benzhydryl 7-thienylacetamido-3-N-ethyl-N-methyl-carbamoyloxymethyl-3-cephem-4-carboxylate

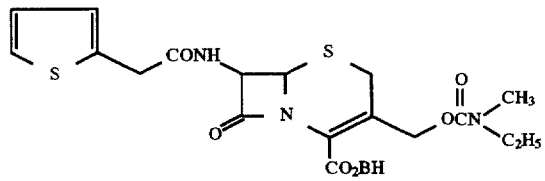

In a similar manner to Preparation Example 2, the title compound was obtained (yield: 66%).

NMR (CDCl$_3$, δ): 1.0–1.15(3H,m), 2.8(½H,s), 2.87(½H, s), 3.18–3.35(2H,m), 3.40–3.55(2H,ABq,J=18 Hz), 3.86 (2H,s), 4.8(1H,d,J=14 Hz), 4.97(1H,d,J=5 Hz), 5.05–5.15 (1H,m), 5.87(1H,dd,J=5 Hz,8 Hz), 6.28(1H,d,J=8 Hz), 6.93 (1H,s), 6.95–7.02(2H,m), 7.2–7.5(11H,m)

PREPARATION EXAMPLE 7

Benzhydryl-7amino-3-N-ethyl-N-methyl carbamoyloxymethyl-3-cephem-4-carboxylate hydrochloride

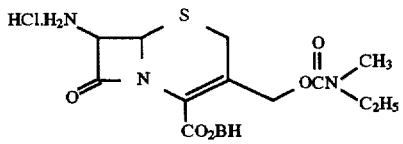

In a similar manner to Preparation Example 3, the title compound was obtained (yield: 81%).

NMR (CDCl$_3$, δ): 1.0–1.15(3H,m), 2.78(½H,s), 2.85 (½H,s), 3.1–3.35(2H,m), 3.40–3.62(2H,ABq,J=18 Hz), 4.87 (1H,d, J=12 Hz), 4.92(1H,d,J=5 Hz), 4.98(1H,m), 5.17–5.23 (1H,m), 6.93(1H,s), 7.15–7.40(10H,m)

PREPARATION EXAMPLE 8

Benzhydryl 7-[2-(2-tritylaminothiazol-4-yl)-2-trityloxyiminoacetamido]-3-N-ethyl-N-methyl-carbamoyloxymethyl-3-cephem-4-carboxylate

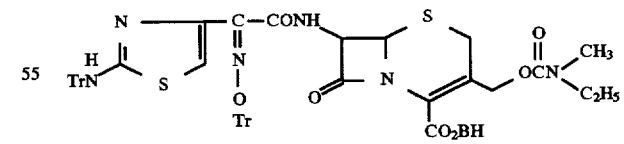

In a similar manner to Preparation Example 4, the title compound was obtained (yield: 72%).

NMR (CDCl$_3$, δ): 1.1–1.2(3H,m), 2.79(½H,s), 2.87(½H, s), 3.18–3.35 (3H,m), 3.48(1H,d,J=18 Hz), 4.82(1H,d,J=12 Hz), 5.06(1H,d,J=5 Hz), 5.07–5.15 (1H,m), 6.07(1H,dd, J=5 Hz,8 Hz), 6.43(1H,s), 6.83(1H,s), 6.95 (1H,s), 7.1–7.4(40H, m), 7.47(1H,d,J=8 Hz)

PREPARATION EXAMPLE 9

Benzhydryl 7-thienylacetamido-3-(1-morpholinyl)-carbonyloxymethyl-3-cephem-4-carboxylate-1-oxide

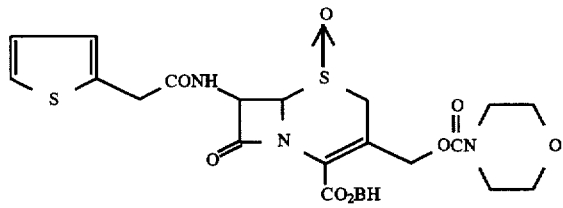

In a similar manner to Preparation Example 1, the title compound was obtained (yield: 53%).

NMR (DMSO-d$_6$, δ): 3.3–3.4(4H,m), 3.5–3.6(4H,m), 3.64,4.03(2H, ABq,J=19 Hz), 4.62,5.17(2H,ABq,J=12 Hz), 4.95–5.00(1H,m), 5.95–6.00(1H,m), 6.98–7.05(3H,m), 7.1–7.6(11H,m), 8.47(1H,d,J=8 Hz)

PREPARATION EXAMPLE 10

Benzhydryl 7-thienylacetamido-3-(1-morpholinyl)-carbonyloxymethyl-3-cephem-4-carboxylate

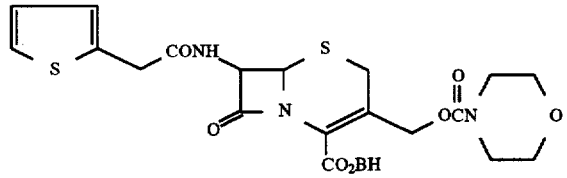

In a similar manner to Preparation Example 2, the title compound was obtained (yield: 52%).

NMR (CDCl$_3$, δ): 3.3–3.5(4H,m), 3.55–3.70(4H,m), 3.40,3.58(2H, ABq,J=19 Hz), 3.87(2H,s), 4.82,5.09(2H, ABq,J=13 Hz), 4.97(1H,d,J=5 Hz), 5.87(1H,d,J=5 Hz,8 Hz), 6.25(1H,d,J=8 Hz), 6.94(1H,s), 6.95–7.05(2H,m), 7.25–7.45 (11H,m)

PREPARATION EXAMPLE 11

Benzhydryl 7-amino-3-(1-morpholinyl)-carbonyloxymethyl-3-cephem-4-carboxylate hydrochloride

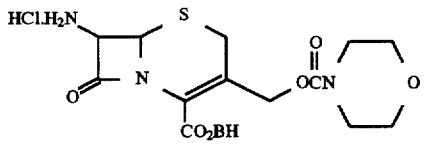

In a similar manner to Preparation Example 3, the title compound was obtained (yield: 62%).

NMR (CDCl$_3$, δ): 3.3–3.5(5H,m), 3.5–3.8(5H,m), 4.98, 5.24(2H, ABq,J=12 Hz), 5.0–5.1(1H,m), 5.14–5.17(1H,m), 6.94(1H,s), 7.2–7.5(10H,m)

PREPARATION EXAMPLE 12

Benzhydryl 7-[(Z)-2-(2-tritlaminothiazol-4-yl)-2-trityloxyiminoacetamido]-3-(1-morpholinyl)-carbonyloxymethyl-3-cephem-4-carboxylate

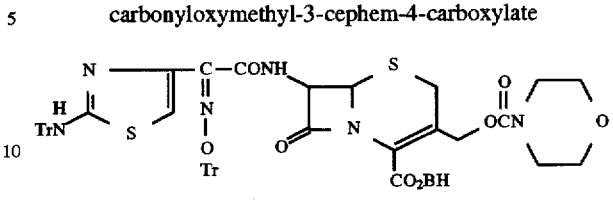

In a similar manner to Preparation Example 4, the title compound was obtained (yield: 59%).

NMR (CDCl$_3$, δ): 3.26,3.50(2H,ABq,J=19 Hz), 3.3–3.7 (8H,m), 4.82,5.11(2H,ABq,J=13 Hz), 5.05(1H,d,J=5 Hz), 6.2(1H,dd,J=5 Hz,8 Hz), 6.44(1H,s), 6.85(1H,br.s), 6.96 (1H,s), 7.15–7.5(41H,m)

PREPARATION EXAMPLE 13

Benzhydryl 7-[(Z)-2-(2-tritylaminothiazol-4-yl)-2-methoxyiminoacetamido]-3-N,N-dimethylcarbamoyl-oxymethyl-3-cephem-4-carboxylate

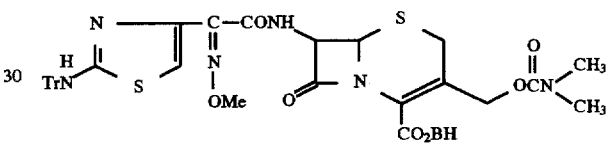

To a solution of phosphorus pentachloride (3.4 g) and pyridine (1.3 g) in dichloromethane (100 ml), a solution of benzhydryl 7-thienylacetamido-3-N,N-dimethylcarbamoyloxymethyl-3-cephem-4-carboxylate (2 g) in N,N-dimethylformamide (6 ml) and dichloromethane (100 ml) was added under ice cooling and the resulting solution was stirred at the same temperature for 30 minutes. The reaction mixture was then added with 1,3-butanediol (4 ml) under cooling in a dry ice-methanol bath (−50° C.), followed by stirring at the same temperature for 50 minutes. After methanol (4 ml) was added to the reaction mixture at the same temperature, the dry ice-methanol bath was removed and the mixture was allowed to stand until its temperature returned to room temperature. The reaction mixture was added with water and dichloromethane, followed by collection of the dichloromethane layer and then, by further extraction of the water layer with dichloromethane. Both dichloromethane layers were combined together and were washed successively with water and a saturated aqueous sodium chloride solution, followed by drying over magnesium sulfate. The solvent was then distilled off under reduced pressure. The residue was dissolved in ethyl acetate and the resulting solution was washed with a dilute aqueous solution of sodium hydrogencarbonate (containing 1.1 equivalent of sodium hydrogencarbonate based on the raw material), followed by drying over magnesium sulfate. Then, the solvent was distilled off under reduced pressure. The residue was dissolved in N,N-dimethylformamide (15 ml). To the resulting solution, (Z)-2-(2-tritylaminothiazol-4-yl)-2-methoxyiminoacetic acid (1.53 g), 1-hydroxy-1H-benztriazole (0.55 g) and dicyclohexylcarbodiimide (0.78 g) were added, followed by stirring at room temperature for 2 hours and 40 minutes. The reaction mixture was added with ethyl acetate and water. After the collection of the ethyl acetate layer, the water layer was extracted further with ethyl acetate. Both ethyl acetate layers were combined together, washed successively with water and a saturated aqueous sodium chloride solution, and dried over magnesium sulfate. Then, the solvent was distilled off under reduced pressure. The residue was purified by chromatography on a silica gel column, whereby benzhydryl 7-[(Z)-2-(2-tritylaminothiazol-4-yl)-2-methoxyiminoacetamido]-3-N,N-dimethylcarbamoyloxymethyl-3-cephem-4-carboxylate was obtained (1.46 g, 48.2%).

NMR (CDCl$_3$, δ): 2.83(3H,s), 2.89(3H,s), 3.36–3.50(2H, ABq,J=18.8 Hz), 4.04(3H,s), 4.84,5.10(2H,ABq,J=13.7 Hz), 5.04(1H,d, J=4.9 Hz), 5.92–5.96 (1H,m), 6.76(1H,s), 6.94(1H,s), 7.20–7.45(25H,m)

PREPARATION EXAMPLE 14

Benzhydryl 7-[(Z)-2-(5-tritylamino-1,2,4-thiazol-3,-yl)-2-methoxyiminoacetamido]-3-(N,N-dimethylcarbamoyloxymethyl-3-cephem-4-carboxylate

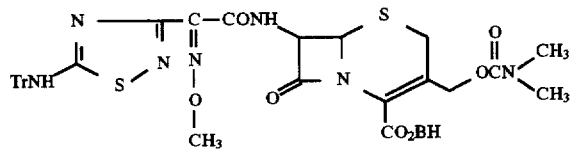

In a similar manner to Preparation Example 13, the title compound was obtained (yield: 71%).

NMR (CD$_3$OD, δ): 2.65–2.87(6H,m), 3.47,3.72(2H,ABq, J=18.5 Hz), 4.07(3H,s), 5.18(1H,d,J=5.1 Hz), 5.94(1H,d, J=5.1 Hz), 6.93(1H,s), 7.25–7.45(25H,m)

PREPARATION EXAMPLE 15

Benzhydryl 7-[(Z)-2-(2-tritylaminothiazol-4-yl)-2-monofluoromethoxyiminoacetamido]-3-(N,N-dimethylcarbamoyloxymethyl-3-cephem-4-carboxylate

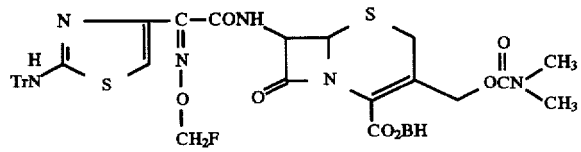

. In a similar manner to Preparation Example 13, the title compound was obtained (yield: 64%).

NMR (CDCl$_3$, δ): 2.82(3H,s), 2.86(3H,s), 3.43,3.56(2H, ABq,J=18.7 Hz), 4.82,5.09(2H,ABq,J=13.9 Hz), 5.05(1H,d, J=4.9 Hz), 5.72,5.86(2H,ABq,d,J=3.6 Hz,55 Hz), 5.94(1H, dd, J=4.9 Hz,8.4 Hz), 6.81(1H,s), 6.93(1H,s), 7.03(1H,d,J= 8.4 Hz),7.28–7.45(25H,m)

PREPARATION EXAMPLE 16

Benzhydryl 7-formamido-3-(1-piperidinyl)-carbonyloxymethyl-2-cephem-4-carboxylate

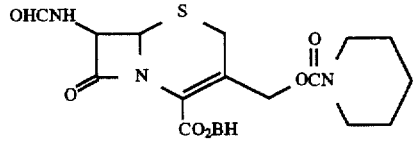

To a solution of benzhydryl 7-formamido-3-hydroxymethyl-3-cephem-4-carboxylate (4.24 g) in tetrahydrofuran (80 ml), N,N'-carbonyldiimidazole (1.62 g) was added under ice cooling, followed by stirring at the same temperature for 1 hour and 25 minutes. Then, the resulting solution was added with a solution of piperidine (0.85 g) in tetrahydrofuran (10 ml) and stirred at the same temperature for 1 hour and 20 minutes. Further stirring was conducted for one hour at room temperature. The reaction mixture was added with piperidine (0.17 g), followed by stirring at room temperature for 11 hours and 10 minutes and then, the resulting reaction mixture was concentrated under reduced pressure. The residue was dissolved in ethyl acetate. The resulting solution was washed successively with 1N hydrochloric acid, water and a saturated aqueous chloride solution, followed by drying over magnesium sulfate. Then, the solvent was distilled off under reduced pressure. The residue was purified by chromatography on a silica gel column, whereby benzhydryl 7-formamido-3-(1-piperidinyl)carbonyloxymethyl-2-cephem-4-carboxylate (2.3 g, 43.0%).

NMR (CDCl$_3$, δ): 1.20–1.40(6H,m), 3.30–3.40(4H,m), 4.57,4.66(2H, ABq,J=12.8 Hz), 5.13(1H,s), 5.22(1H,d,J=4.0 Hz), 5.70–5.75(1H,m), 6.44(1H,s), 6.89(1H,s), 7.25–7.40 (10H,m), 8.23(1H,s)

PREPARATION EXAMPLE 17

Benzhydryl 7-formamido-3-(1-piperidinyl)-carbonyloxymethy-1-3-cephem-4-carboxylate-1-oxide

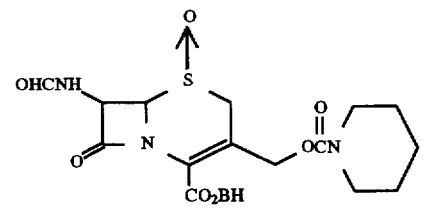

To a solution of benzhydryl 7-formamido-3-(1-piperidinyl)carbonyloxymethyl-2-cephem-4-carboxylate (3.4 g) in ethyl acetate (20 ml), m-chloroperbenzoic acid (1.53 g) was added under ice cooling, followed by stirring at the same temperature for 55 minutes. To the reaction mixture, m-chloroperbenzoic acid (0.15 g) was added, followed by stirring under ice cooling for 35 minutes. The crystals precipitated were collected by filtration. The filtrate was concentrated under reduced pressure. The residue was purified by chromatography on a silica gel column, whereby benzhydryl 7-formamido-3-(1-piperidinyl) carbonyloxyethyl-3-cephem-4-carboxylate-1-oxide (1.53 g, 43.7%) was obtained together with precipitated crystals.

NMR (DMSO-d$_6$, δ): 1.35–1.55(6H,m), 3.23–3.30(4H, m), 3.65,4.01(2H,ABq, J=18.7 Hz), 4.58,5.11(2H,ABqJ=

13.6 Hz), 4.98(1H, d,J=3.7 Hz), 6.05(1H,m), 6.93(1H,s), 7.25–7.55(10H,m), 8.15(1H,s), 8.43(1H,d,J=9.5 Hz)

PREPARATION EXAMPLE 18

Benzhydryl 7-formamido-3-(1-piperidinyl)-carbonyloxymethyl-3-cephem-4-carboxylate

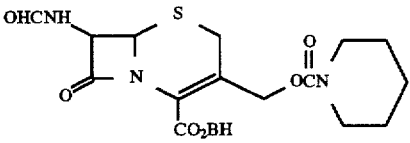

To a solution of benzhydryl 7-formamido-3-(1-piperidinyl)carbonyloxymethyl-3-cephem-4-carboxylate-1-oxide (2.07 g) in N,N-dimethylformamide (25 ml), phosphorus trichloride (1 ml) was added under cooling in a dry ice-ethanol bath (−60° C.), followed by stirring for 35 minutes. The reaction mixture was successively added with ethyl acetate and water under cooling in a dry ice-ethanol bath and then, the resulting mixture was increased to room temperature. The ethyl acetate layer was collected and the water layer was extracted further with ethyl acetate. Both ethyl acetate layers were combined together, successively washed with water and a saturated aqueous sodium chloride solution, and then dried over magnesium sulfate. Then, the solvent was distilled off under reduced pressure. The residue was purified by chromatography on a silica gel column, whereby benzhydryl 7-formamido-3-(1-piperidinyl)-carbonyloxymethyl-3-cephem-4-carboxylate (1.87 g, 93.0%) was obtained.

NMR (CDCl$_3$, δ): 1.35–1.55(6H,m), 3.20–3.35(4H,m), 3.35,3.46(2H, ABq,J=18.7 Hz), 4.76,5.03(2H,ABq,J=13.9 Hz), 4.90(1H,d,J=3.5 Hz), 5.80–5.85(1H,m), 6.86(1H,s), 7.14–7.40(10H,m), 7.84(1H,d,J=9.2 Hz), 8.15(1H,s)

PREPARATION EXAMPLE 19

Benzhydryl 7-[(Z)-2-(2-tritylaminothiazol-4-yl)-2-trityloxyiminoacetamido]-3-(1-piperidinyl)-carbonyloxymethyl-3-cephem-4-carboxylate

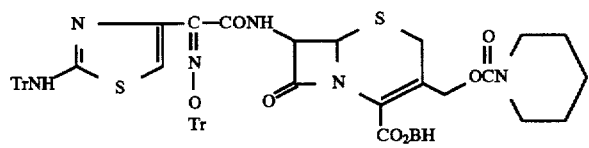

To a solution of benzhydryl 7-formamido-3-(1-piperidinyl)carbonyloxymethyl-3-cephem-4-carboxylate (1.87 g) in tetrahydrofuran-methanol (1:1, 20 ml), 36% hydrochloric acid (2 ml) was added and the resulting solution was stirred at room temperature for 2 hours and 10 minutes. Then, the solvent was distilled off under reduced pressure. The residue was added with ethyl acetate and water. The ethyl acetate layer was collected and the water layer was extracted further with ethyl acetate. Both ethyl acetate layers were combined together, washed with a saturated aqueous sodium chloride solution and then, dried over magnesium sulfate. The solvent was thereafter distilled off under reduced pressure. The residue was dissolved in N,N-dimethylformamide (18 ml). To the resulting solution, (Z)-2-(2-tritylaminothiazol-4-yl)-2-trityloxyiminoacetic acid (2.35 g), 1-hydroxy-1H-benztriazole (0.56 g) and dicyclohexylcarbodiimide (0.79 g) were added, followed by stirring at room temperature for 1 hour and 5 minutes. The reaction mixture was added with ethyl acetate and water. The ethyl acetate layer was collected and the water layer was extracted further with ethyl acetate. Both ethyl acetate layers were combined together, washed successively with water and a saturated aqueous sodium chloride solution and then was dried over magnesium sulfate. The solvent was thereafter distilled off under reduced pressure. The residue was purified by chromatography on a silica gel column, whereby benzhydryl 7-[(Z)-2-(2-tritylaminothiazol-4-yl)-2-trityloxyiminoacetamido]-3-(1-piperidinyl)carbonyloxymethyl-3-cephem-4-carboxylate (1.4 g, 33.7%).

NMR (CDCl$_3$, δ): 1.42–1.64(6H,m), 3.25–3.43(4H,m), 3.26,3.48 (2H,ABq,J=18.6 Hz), 4.82,5.12(2H,ABq,J=13.9 Hz), 5.05(1H,d,J=4.9 Hz), 6.05–6.12(1H,m), 6.44(1H,s), 6.96(1H,s), 7.15–7.43(40H,m)

PREPARATION EXAMPLE 20

Benzhydryl 7-formamido-3-(1-azetidinyl)-carbonyloxymethyl-3-cephem-4-carboxylate

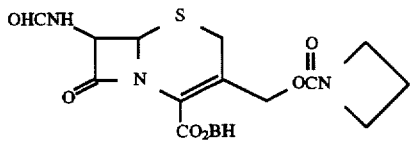

In a similar manner to Preparation Example 16, the title compound was obtained (yield: 58%).

NMR (CDCl$_3$, δ): 2.15–2.25(2H,m), 3.90–4.00(4H,m), 4.55,4.61 (2H,ABq,J=12.7 Hz), 5.13(1H,s), 5.21 (1H,d,J= 4.0 Hz), 5.69(1H,dd,J=4.0 Hz,9.2 Hz), 6.44(1H,s), 6.82(1H, d, J=9.2 Hz), 6.90(1H,s), 7.28–7.40(10H,m), 8.22(1H,s)

PREPARATION EXAMPLE 21

Benzhydryl 7-formamido-3-(1-azetidinyl)-carbonyloxymethyl-3-cephem-4-carboxylate-1-oxide

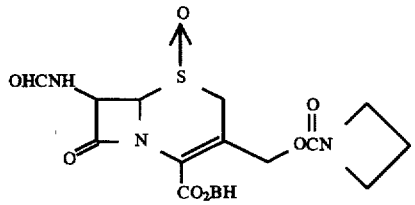

In a similar manner to Preparation Example 17, the title compound was obtained (yield: 44%).

NMR (CDCl$_3$, δ): 2.15–2.25(2H,m), 3.20,3.82(2H,ABq, J=18.9 Hz), 3.90–4.05(4H,m), 4.45(1H,d,J=4.8 Hz); 4.72, 5.24 (2H,ABq,J=14.3 Hz), 6.07(1H,m), 6.93(1H,s), 7.20–7.50(10H,m), 8.21(1H,s)

PREPARATION EXAMPLE 22

Benzhydryl 7-formamido-3-(1-azetidinyl)-carbonyloxymethyl-3-cephem-4-carboxylate

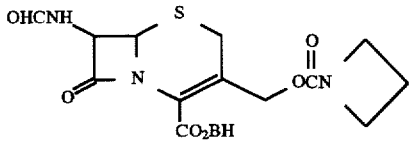

In a similar manner to Preparation Example 18, the title compound was obtained (yield: 97%).

NMR (CDCl$_3$, δ): 2.15–2.25(2H,m), 3.44.3.57 (2H,ABq, J=18.7 Hz), 3.85–4.10(4H,m), 4.83,5.06(2H,ABq,J=13.9 Hz), 4.99(1H,d,J=4.9 Hz), 5.93(1H,dd,J=4.9 Hz,9.2 Hz), 6.39(1H,d,J=9.2 Hz), 6.95(1H,s), 7.25–7.45(10H,m), 8.25 (1H,s)

PREPARATION EXAMPLE 23

Benzhydryl 7-[(Z)-2-(2-tritylaminothiazol-4-yl)-2-trityloxyiminoacetamido]-3-(1-azetidinyl)-carbonyloxymethyl-3-cephem-4-carboxylate

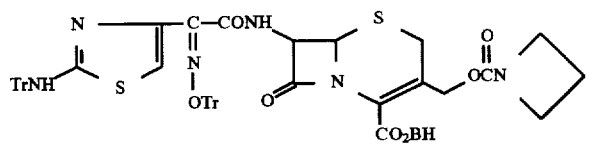

In a similar manner to Preparation Example 19, the title compound was obtained (yield: 94%).

NMR (CDCl$_3$, δ): 2.15–2.27(2H,m), 3.26,3.50(2H,ABq, J=18.5 Hz), 3.85–4.10(4H,m), 4.82,5.08(2H,ABq,J=13.8 Hz), 5.05(1H,d,J=4.9 Hz), 6.11(1H,dd,J=4.9 Hz,8.8 Hz), 6.47(1H,s), 6.99(1H,s), 7.15–7.53(40H,m)

PREPARATION EXAMPLE 24
Mixture of benzhydryl 7-formamido-3-[N-(2-hydroxyethyl)-N-methylcarbamoyloxymethyl]-2-cephem-4-carboxylate and benzhydryl 7-formamido-3-[N-(2-hydroxyethyl)-N-methylcarbamoyloxymethyl]-2-cephem-4-carboxylate

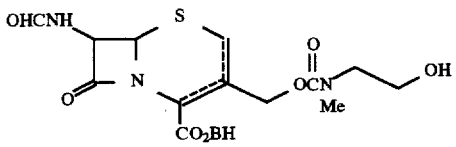

In a similar manner to Preparation Example 16, the title compound was obtained (yield: 51%).

NMR (CDCl$_3$, δ): 2.90–2.97(3H,m), 3.24–3.35(2H,m), 3.49,3.59($^{10}/_{12}$H, ABq,J=19 Hz), 3.61–3.70(2H,m), 4.57–4.76($^{14}/_{12}$H,m), 4.86–4.90,5.09–5.18($^{10}/_{12}$H,m), 4.99 ($^{5}/_{12}$H,d,J=5 Hz), 5.18($^{7}/_{12}$H,s), 5.24($^{7}/_{12}$H,d,J=5 Hz), 5.65–5.68 ($^{7}/_{12}$H,m), 5.93($^{5}/_{12}$H,dd,J=5 Hz,9 Hz), 6.47–6.50 ($^{7}/_{12}$H,m), 6.91($^{7}/_{12}$H,s), 6.99($^{5}/_{12}$H,s), 7.15–7.20 (10H,m), 8.22(1H,s)

PREPARATION EXAMPLE 25
Benzhydryl 7-formamido-3-(N-(2-hydroxyethyl)-N-methylcarbamoyloxymethyl-3-cephem-4-carboxylate-1-oxide

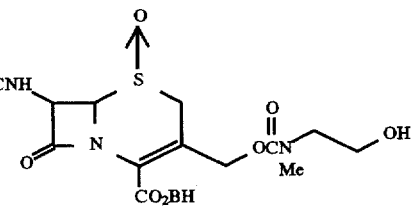

In a similar manner to Preparation Example 17, the title compound was obtained (yield: 49%).

NMR (CDCl$_3$, δ): 2.87(³⁄₂H,s), 2.90(³⁄₂H,s), 3.22–3.29 (1H,m),3.36–3.41(1H,m), 3.59–3.62(1H,m), 3.69,3.71(1H, m), 3.94,4.09(2H,ABq,J=20 Hz), 4.46–4.56(1H,m), 4.77–4.81(1H,m), 5.23–5.29(1H,m), 6.08–6.10(1H,m), 6.94 (1H,s), 8.22(1H,s)

PREPARATION EXAMPLE 26
Benzhydryl 7-[2-trityloxyimino-2-(2-tritylaminothiazol-4-yl)acetamido]-3-[N-(2-hydroxyethyl)-N-methylcarbamoyloxymethyl]-3-cephem-4-carboxylate

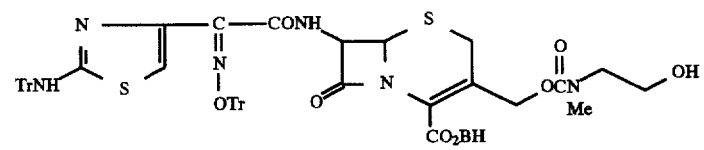

In a similar manner to Preparation Example 19, the title compound was obtained (yield: 12%).

NMR (CDCl$_3$, δ): 2.94–2.97(3H,m), 3.24–3.30(3H,m), 3.43–3.52(3H,m), 4.80–4.83(1H,m), 5.06(1H,d,J=5 Hz), 5.10–5.15(1H,m), 6.11(1H,dd,J=5 Hz,9 Hz), 6.44(1H,s), 6.96(1H,s), 7.2–7.4(40H,m)

PREPARATION EXAMPLE 27

Benzhydryl 7-formamido-3-N-carbamoylmethyl-N-methylcarbamoyloxymethyl-3-cephem-4-carboxylate-1-oxide

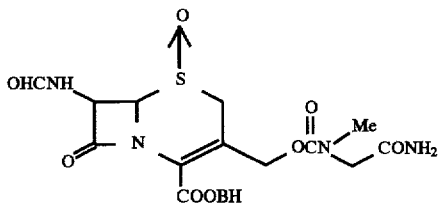

To a solution mixture of benzhydryl 7-formamido-3-(1-imidazoryl)carbonyloxymethyl-2-cephem-4-carboxylate-1-oxide (5.4 g) in a tetrahydrofuran (90 ml), and water (18 ml) mixture, sarcosinamide hydrochloride (1.9 g) and pyridine (1.23 ml) were added, followed by stirring at room temperature for 15 hours and at 45° C. for 12 hours. After the reaction mixture was concentrated, the residue was added with water and ethyl acetate. The ethyl acetate layer was successively washed with 1N hydrochloric acid, water and a saturated aqueous sodium chloride solution, dried over magnesium sulfate and then concentrated. The residue was purified by chromatography on a silica gel column, whereby the title compound was Obtained (yield: 750 mg; 15.0%)

NMR (CDCl$_3$, δ): 2.78(3H,m), 3.78(2H,m), 3.5–4.1(2H, m), 4.95(1H,m), 4.5–5.1(2H,m), 6.03(1H,m), 6.9(1H,m), 7.2–7.5(10H,m), 8.14(1H,s), 8.42(1H,d,J=8 Hz)

PREPARATION EXAMPLE 28

Benzhydryl 7-formamido-3-N-cyanomethyl-N-methylcarbamoyloxymethyl-3-cephem-4-carboxylate

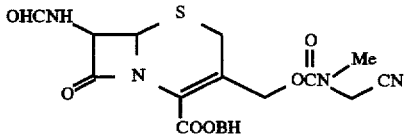

In a similar manner to Preparation Example 18, the title compound was obtained (yield: 66%).

NMR (CDCl$_3$, δ): 2.94(3H,s), 3.4–4.3(4H,m), 4.87,5.15 (2H,ABq,J=18 Hz), 5.08(1H,d,J=4 Hz), 5.96(1H,dd,J=4 Hz,8 Hz), 6.45(1H,br.s), 6.94(1H,s), 7.2–7.45(10H,m), 8.26 (1H,s)

PREPARATION EXAMPLE 29

Benzhydryl 7-[(Z)-2-trityloxyimino-2-(2-tritylaminothiazol-4-yl)acetamido]-3-N-cyanomethyl-N-methylcarbamoyloxymethyl-3-cephem-4-carboxylate

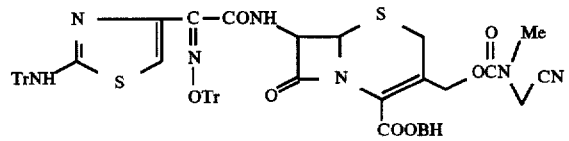

To a solution of benzhydryl 7-formamido-3-N-cyanomethyl-N-methylcarbamoyloxymethyl-3-cephem-4-carboxylate (430 mg) in a methanol (6 ml), and tetrahydrofuran (6 ml) mixture, concentrated hydrochloric acid (0.8 ml) was added dropwise under ice cooling, followed by stirring at room temperature for 2 hours. The reaction mixture was concentrated, added with ethyl acetate, successively washed with water, a saturated aqueous solution of sodium bicarbonate and a saturated aqueous sodium chloride solution, dried over magnesium sulfate and then concentrated.

To a solution of the residue thus obtained (410 mg) in N,N-dimethylformamide (8 ml), (Z)-2-(2-tritylaminothiazol-4-yl)-2-trityloxyiminoacetic acid (610 mg), dicyclohexylcarbodiimide (197 mg) and 1-hydroxybenzotriazole (123 mg) were added, followed by stirring at room temperature for 10 hours. The reaction mixture was added with water and ethyl acetate. The ethyl acetate layer was successively washed with water, 1N hydrochloric acid, a saturated aqueous solution of sodium bicarbonate and a saturated aqueous sodium chloride solution, dried over magnesium sulfate and then concentrated. The residue was purified by chromatography on a silica gel column, whereby the title compound was obtained (yield: 460 mg; 44.5%).

NMR (CDCl$_3$, δ): 2.87(0.6H,br.s), 2.96(0.4H,br.s), 3.08–3.48(2H,m), 3.8–4.3(2H,m), 4.7–5.2(2H,m), 5.04(1H, d,J=5 Hz), 6.10(1H,dd,J=5 Hz,8 Hz), 6.45(1H,s), 6.96(1H, s), 7.1–7.5(40H,m)

PREPARATION EXAMPLE 30

Benzhydryl 7-formamido-3-(3-hydroxyl-1-pyrrolidinyl)carbonyloxymethyl-3-cephem-4-carboxylate and 2-cephem derivative thereof

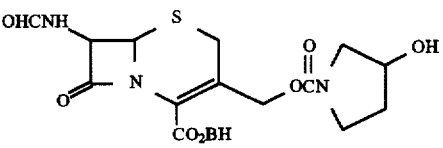

In a similar manner to preparation Example 16, the title compound was obtained (yield: 28%).

NMR (CDCl$_3$, δ): 1.9(2H,m), 3.2–3.6(4H,m), 4.4–4.8 (3H,m), 5.01(0.3H,d,J=5 Hz), 5.17(0.7H,s), 5.23(0.7H,s), 5.70(0.7H,m), 5.94(0.3H,m), 6.48(1H,m), 6.91(0.7H,s), 6.95(0.3H,s), 7.25–7.45(10H,m), 8.25(1H,m)

PREPARATION EXAMPLE 31

Benzhydryl 7-formamido-3-(3-hydroxy-1-pyrrolidinyl)carbonyloxymethyl-3-cephem-4-carboxylate-1-oxide

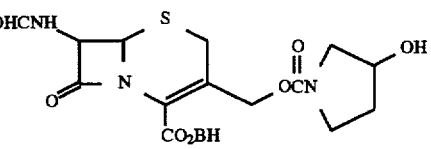

In a similar manner to preparation Example 17, the title compound was obtained (yield: 68%).

NMR (DMSO-d$_6$, δ): 1.6–1.95(2H,m), 3.1–3.4(4H,m), 3.84(2H,m), 4.86(2H,m), 4.98(2H,m), 6.05(1H,dd,J=9.8 Hz,5 Hz), 6.93(1H,s), 7.24–7.53(10H,m), 8.15(1H,s), 8.42 (1H,d,J=9.8 Hz)

PREPARATION EXAMPLE 32

Benzhydryl 7-formamido-3-(3-hydroxy-1-pyrrolidinyl)carbonyloxymethyl-3-cephem-4-carboxylate

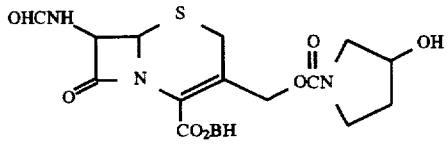

In a similar manner to Preparation Example 18, the title compound was obtained (yield: 78%).

NMR (CDCl$_3$, δ): 2.16(2H,m), 3.3–3.7(6H,m), 4.99(1H, d,J=5 Hz), 4.8–5.2(2H,m), 5.48(1H,br.s), 5.93(1H,dd,J=9 Hz,5 Hz) 6.48(1H,d,J=9 Hz), 6.95(1H,s), 7.2–7.4(1H,s), 8.24(1H,s)

PREPARATION EXAMPLE 33

Benzhydryl 7-[(Z)-2-trityloxyimino-2-(2-tritylaminothiazol-4-yl)acetamido]-3-(3-hydroxy-1-pyrrolidinyl)carbonyloxy methyl-3-cephem-4-carboxylate

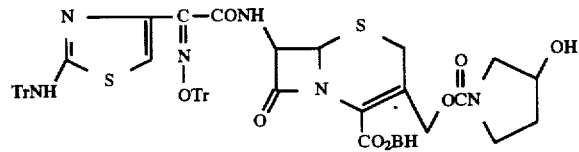

In a similar manner to Preparation Example 19, the title compound was obtained (yield: 6%).

NMR (CDCl$_3$, δ): 1.97(2H,m), 3.1–3.5(6H,m), 4.26(1H, b), 4.98(1H,d,J=5 Hz), 4.7–5.2(2H,m), 6.05(1H,dd, J=9 Hz,5 Hz), 6.46(1H,s), 6.94(1H,s), 7.1–7.5(40H,m)

PREPARATION EXAMPLE 34

Benzhydryl 7-formamido-3-[((S)-(+)-2-hydroxymethyl-1-pyrrolidinyl)carbonyloxymethyl]-3-cephem-4-carboxylate and 2-cephem derivative thereof

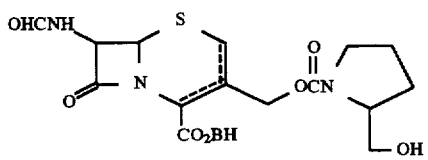

In a similar manner to Preparation Example 16, the title compound was obtained (yield: 16%).

NMR (CDCl$_3$, δ): 1.7–2.1(4H,m), 3.2–4.0(4.4H,m), 4.65 (1H,m), 4.6–5.3(1.2H,m), 4.86,5.15(0.8H,ABq,J=14 Hz), 5.01(0.4H,d,J=5 Hz), 5.18(0.6H,s), 5.25(0.6H,m), 5.72 (0.6H,m), 5.94(0.4H,dd,J=9 Hz,5 Hz), 6.45(0.6H,m), 6.91 (1H,s), 7.2–7.5(10H,m), 8.25(1H,s)

PREPARATION EXAMPLE 35

Benzhydryl 7-formamido-3-[((S)-(+)-2-hydroxymethyl-1-pyrrolidinyl)carbonyloxymethyl]-3-cephem-4-carboxylate-1-oxide

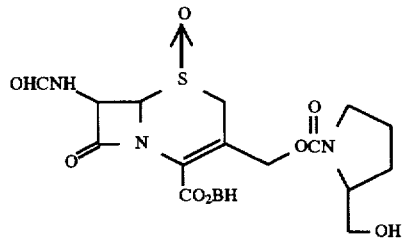

In a similar manner to preparation Example 17, the title compound was obtained (yield: 59%).

NMR (CDCl$_3$, δ): 1.5–2.1(4H,m), 3.2–4.0(6H,m), 4.53 (1H,m), 4.80,5.34(2H,ABq,J=14 Hz), 5.25(1H,m), 6.15(1H, dd, J=9 Hz,15 Hz), 7.97(1H,s), 7.2–7.5(10H,m), 8.27(1H,s)

PREPARATION EXAMPLE 36

Benzhydryl 7-formamido-3-[((S)-(+)-2-hydroxymethyl-1-pyrrolidinyl)carbonyloxymethyl]-3-cephem-4-carboxylate

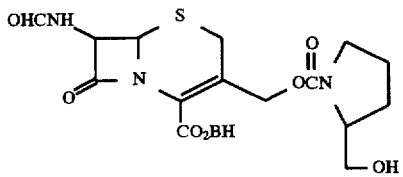

In a similar manner to Preparation Example 18, the title compound was obtained (yield: 74%).

NMR (CDCl$_3$, δ): 1.80–2.10(4H,m), 3.27–3.56(6H,m), 3.90(1H,m), 4.97(1H,d,J=4.8 Hz), 5.01(2H,ABq,J=14 Hz), 5.90(1H,dd,J=4.8 Hz,8.9 Hz), 6.94(1H,s), 7.23–7.44(10H, m), 8.18(1H,s)

PREPARATION EXAMPLE 37

Benzhydryl 7-[(Z)-2-(2-tritylaminothiazol-4-yl)-2-trityloxyiminoacetamido]-3-[(S)-(+)-2-hydroxymethylpyrrolidino]carbonyloxymethyl-3-cephem-4-carboxylate

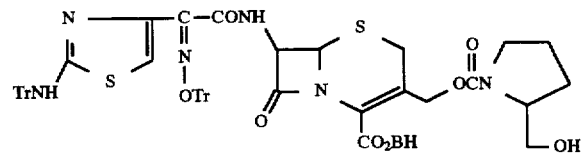

In a similar manner to Preparation Example 19, the title compound was obtained (yield: 6%).

NMR (CDCl$_3$, δ): 1.80–2.00(4H,m), 3.21–3.60(6H,m), 3.90(1H,m), 5.02(1H,d,J=4.8 Hz), 5.08(2H,ABq,J=14 Hz), 6.07(1H,dd,J=4.8 Hz,8.8 Hz), 6.45(1H,s), 6.95(1H,s), 7.20–7.40(40H,m)

PREPARATION EXAMPLE 38

Mixture of benzhydryl 7-[(Z)-2-trityloxyimino-2-(2-tritylaminothiazol-4-yl)acetamido]-3-(1-pyrrolidinyl)carbonyloxymethyl-3-cephem-4-carboxylate and benzhydryl 7-[2-trityloxyimino-2-(2-tritylaminothiazol-4-yl)acetamido]-3-(1-pyrrolidinyl)carbonyloxymethyl-2-cephem-4-carboxylate

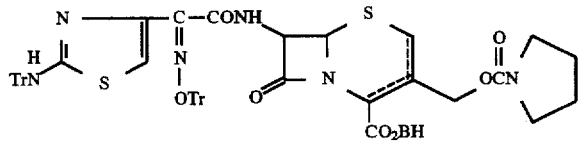

In tetrahydrofuran (200 ml), 2-(2-tritylaminothiazol-4-yl)-2-trityloxyiminoacetic acid (20 g), 1-hydroxybenzotriazole (6 g) and dicyclohexylcarbodiimide (9.2 g) were dissolved. The resulting solution was stirred at room temperature for 1 hour and 15 minutes (Liquid A).

On the other hand, 7-amino-3-hydroxymethyl-3-cephem-4-carboxylic acid (10.3 g) was suspended in acetonitrile (500 m l), followed by the addition of N-methyl-N-(trimethylsilyl)trifluoroacetamide (24.8 ml) at room temperature. The resulting suspension was stirred at room temperature for 20 minutes (Liquid B).

After filtration of Liquid A, the solvent was distilled off under reduced pressure. The residue thus obtained was recrystallized from a mixed solvent of n-hexane and isopropyl ether so that powdery crystals were formed. They were dissolved in tetrahydrofuran (50 ml) and the resulting solution was added to Liquid B at room temperature, followed by stirring for one hour and 15 minutes.

The reaction mixture was thereafter filtered and the filtrate was added with diphenyldiazomethane (11.6 g) and methanol (8.6 g), followed by stirring at room temperature for 2 hours. The reaction mixture was distilled off under reduced pressure. The residue thus obtained was dissolved in tetrahydrofuran (120 ml) and the resulting solution was added with N,N'-carbonyl-diimizazole (4.9 g) at room temperature, followed by stirring at the same temperature for 2 hours.

In the next place, the reaction mixture was added with pyrrolidine (3.49 g), followed by stirring for 2 hours and 20 minutes. The reaction mixture was distilled off under reduced pressure. The residue thus obtained was purified by column chromatography (SiO$_2$250 g; benzene:ethyl acetate= 8:1), whereby the title compound was obtained (yield: 6.94 g; 20%).

NMR (CDCl$_3$, δ): 1.80–1.95(4H,m), 3.25–3.30(4H,m), 4.60(⅔H,s), 4.82,5.10(2H,ABq,J=13 Hz), 5.05(⅓H,d,J=5 Hz), 5.18(⅓H,s), 5.25(⅔H,d,J=5 Hz), 5.85(⅔H,dd, J=5 Hz,9 Hz), 6.15(⅔H,dd,J=5 Hz,9 Hz), 6.22(⅔H,s), 6.42(⅓H, s), 6.44(⅔H,s), 7.01,7.03(1H,s), 7.25–7.40(40H,m)

PREPARATION EXAMPLE 39

Benzhydryl 7-[(Z)-2-trityloxyimino-2-(2-tritylaminothiazol-4-yl)acetamido]-3-(1-pyrrolidinyl)carbonyloxymethyl-3-cephem-4-carboxylate-1-oxide

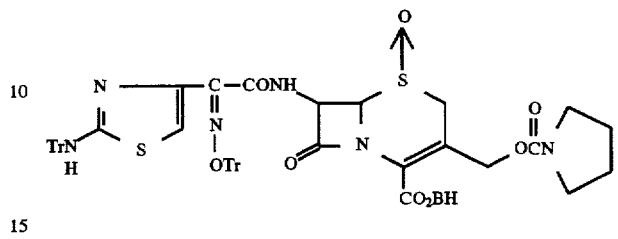

To a solution of the mixture (3.7 g), which had been obtained in Preparation Example 38, in tetrahydrofuran (40 ml), m-chlorobenzoic acid (834 ml) was added under ice cooling. The resulting solution was stirred at the same temperature for 1.5 hours. The reaction mixture was distilled off under reduced pressure. The residue thus obtained was purified by column chromatography (SiO$_2$50 g, benzene-:ethyl acetate=6:1), whereby the title compound was obtained (yield: 1.44 g; 38%).

NMR (CDCl$_3$, δ): 1.83–1.90(4H,m), 3.00–3.62(2H,ABq, J=18 Hz), 3.21–3.25(2H,m), 3.35–3.39(2H,m), 4.41–4.43 (1H,m), 4.72,5.32(2H,ABq,J=13 Hz), 6.30(1H,dd,J=5 Hz,9 Hz), 6.42(1H,s), 6.93(1H,s), 7.35–7.40(40H,m)

PREPARATION EXAMPLE 40

Benzhydryl 7-[(Z)-2-trityloxyimino-2-(2-tritylaminothiazol-4-yl)acetamido]-3-(1-pyrrolidinyl)carbonyloxymethyl-3-cephem-4-carboxylate

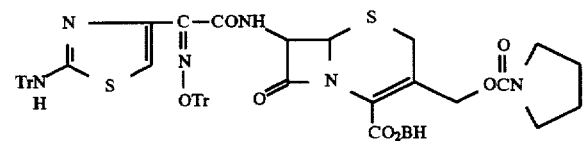

To a solution of the compound (1.44 g), which had been obtained in Preparation Example 39, in N,N-dimethylformamide (15 ml), phosphorus trichloride (0.43 ml) was added at –30° C. The resulting solution was stirred at the same temperature for 30 minutes.

The reaction mixture was poured into ethyl acetate, which had been cooled to –78° C. in advance, followed by the addition of water. The ethyl acetate layer was collected, washed with water and a saturated aqueous sodium chloride solution and then dried over anhydrous magnesium sulfate. Then, the solvent was distilled off under reduced pressure. The residue thus obtained was dissolved in ethyl acetate and the resulting solution was added to isopropyl ether. The resulting precipitate was collected by filteration and washed with isopropyl ether, whereby the title compound was obtained (yield: 895 mg, 63%).

NMR (CDCl$_3$, δ): 1.84–1.87(4H,m), 3.28–3.50(2H,ABq, J=18 Hz), 3.20–3.24(2H,m), 3.35–3.38(2H,m), 4.82,5.10 (2H,ABq, J=13 Hz), 5.05(1H,d,J=5 Hz), 6.09(1H,dd,J=5 Hz,9 Hz), 6.42(1H,s), 6.94(1H,s), 7.35–7.40(40H,m)

EXAMPLE 1

Sodium 7-[(Z)-2-(2-aminothiazol-4-yl)-2-hydroxyiminoacetamido]-3-N,N-dimethyl-carbamoyloxymethyl-3-cephem-carboxylate

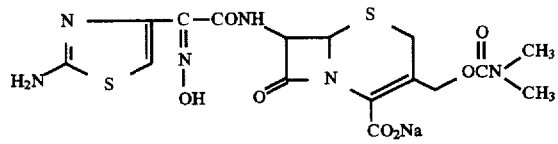

To the liquid mixture of trifluoroacetic acid (3 ml) and anisole (2 ml), benzhydryl 2-[(Z)-2-tritylaminothiazol- 4-yl)-2-trityloxyiminoacetamido]-3-N,N-dimethylcarbamoyloxymethyl-3-cephem-4-carboxylate (1.4 g; 1.3 mmol), which had been obtained in Preparation Example 4, was added. The resulting solution was stirred for one hour. The reaction mixture was added with isopropyl ether (100 ml) and the resulting precipitate was collected by filtration. The filtrate was added to formic acid (10 ml), followed by the reaction at room temperature for 2 hours. Formic acid was distilled off under reduced pressure, followed by the addition of ethyl ether. The resulting precipitate was collected by filtration. The filtrate was purified by reversed-phase column chromatography, whereby the title compound was obtained (yield: 240 mg, 39%).

NMR (D$_2$O, δ): 2.7(6H,br.s), 3.42,3.69(2H,ABq,J=19 Hz), 4.67,4.91(2H,ABq,J=12.6 Hz), 5.22(1H,d,J=4.8 Hz), 5.85(1H,d,J=4.8 Hz), 7.00(1H,s)

EXAMPLE 2

Sodium 7-[(Z)-2-(2-aminothiazol-4-yl)-2-hydroxyiminoacetamido]-3-N-ethyl-N-methylcarbamoyloxymethyl-3-cephem-4-carboxylate

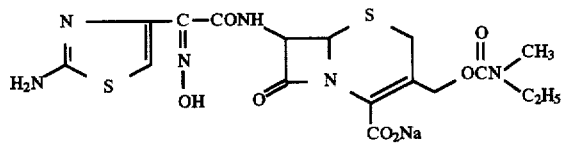

The compound, which had been obtained in Preparation Example 8, was treated in a similar manner to Example 1, whereby the title compound was obtained (yield: 15%).

NMR (D$_2$O, δ): 1.05–1.15(27/10H,m), 1.25–1.35(3/10H, m), 2.72(3/10H,br.s), 2.90(27/10H,br.s), 3.05–3.15(2/10Hm), 3.25–3.40(18/10H,m),3.4–3.5(1H,m), 3.7–3.78(1H,m), 4.70–4.78(1H,m), 4.90–5.00 (1H,m), 5.24–5.27(1H,m), 5.85–5.90(1H,m), 7.02(1H,s)

EXAMPLE 3

Sodium 7-[(Z)-2-(2-aminothiazol-4-yl)-2-hydroxyiminoacetamido]-3-1-morpholyl)-carbonyloxymethyl-3-cephem-4-carboxylate

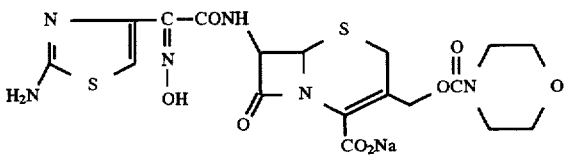

The compound, which had been obtained in Preparation Example 12, was treated in a similar manner to Example 1, whereby the title compound was obtained (yield: 15%).

NMR (D$_2$O, δ): 3.42,3.72(2H,ABq,J=18 Hz), 3.45–3.60 (4H,m), 3.70–3.80(4H,m), 4.75,4.95(2H,ABq,J=13 Hz), 5.23(1H,d,J=4.5 Hz), 5.86 (1H,d,J=4.5 Hz), 7.01 (1H,s)

EXAMPLE 4

Sodium 7-[(Z)-2(2-aminothiazol-4-yl)-2-methoxyiminoacetamido]-3-N,N-dimethylcarbamoyl-oxymethyl-3-cephem-4-carboxylate

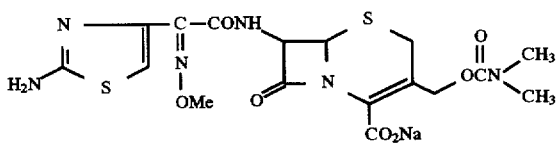

To a solution of benzhydryl 7-((Z)-2-tritylaminothiazol-4-yl)-2-methoxyiminoacetamido]-3-N,N-dimethylcarbamoyloxymethyl-3-cephem-4-carboxylate (1.46 g), which had been obtained in Preparation Example 13, in anisole (10 ml), trifluoroacetic acid (20 ml) was added dropwise under ice cooling. At the same temperature, the resulting solution was stirred for two hours and twenty minites. The reaction mixture was concentrated under reduced pressure. The residue was dissolved in methanol. The resulting solution was added with diisopropyl ether to precipitate crystals. The crystals precipitated were collected by filtration and dissolved in methanol, followed by dissolution of sodium acetate (600 mg). The resulting solution was added further with diisopropyl ether to precipitate crystals. The crystals thus precipitated were collected by filtration, washed with diisopropyl ether and then air-dried. The crystals thus obtained were purified by reverse-phase column chromatography, whereby sodium 7-[(Z)-2-(2-aminothiazol-4-yl)-2-methoxyiminoacetamido-3-N,N-dimethylcarbamoyloxymethyl-3-cephem-4-carboxylate (71 mg, 8.5%) was obtained.

NMR (D$_2$O, δ): 2.65–2.80(6H,m), 3.26,3.52(2H,ABq,J= 18.1 Hz), 3.83(3H,s), 4.52,4.75(2H,ABq,J=12.6 Hz), 5.05 (1H,d,J=4.8 Hz), 5.66(1H,d,J=4.8 Hz), 6.85(1H,s)

EXAMPLE 5

Sodium 7-[(Z)-2-(5-amino-1,2,4-thiazol-3-yl)-2-methoxyiminoacetamido]-3-N,N-dimethylcarbamoyl-oxymethyl-3-cephem-4-carboxylate

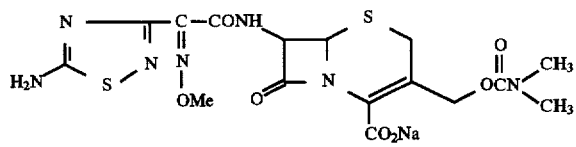

The compound, which had been obtained in Preparation Example 14, was treated in a similar manner to Example 4, whereby the title compound was obtained (yield: 27%).

NMR (D$_2$O, δ): 2.68(6H,s), 3.21,3.46(2H,ABq,J=18.0 Hz),3.89(3H,s), 4.50,4.72(2H,ABq,J=12.3 Hz), 5.01(1H,d, J=4.7 Hz), 5.67(1H,d,J=4.7 Hz)

EXAMPLE 6

Sodium 7-[(Z)-2-(2-aminothiazol-4-yl)-2-monofluoromethoxyiminoacetamido]-3-N,N-dimethylcarbamoyloxymethyl-3-cephem-4-carboxylate

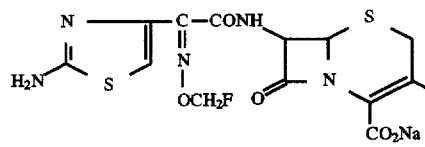

The compound, which had been obtained in Preparation Example 15, was treated in a similar manner to Example 4, whereby the title compound was obtained (yield: 10%).

NMR (D$_2$O, δ): 2.62–2.73(6H,m), 3.22,3.48(2H,ABq,J= 18.0 Hz), 4.49,4.72(2H,ABq,d,J=12.8 Hz,1.6 Hz), 5.02–5.04(1H,m), 5.63–5.66(1H,m), 5.61(2H,d,J=55.2 Hz), 6.95(1H,s)

EXAMPLE 7

Sodium 7-[(Z)-2-(2-aminothiazol-4-yl)-2-hydroxyiminoacetamido]-3-(1-piperidinyl)-carbonyloxymethyl-3-cephem-4-carboxylate

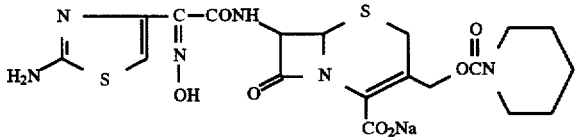

The compound, which had been obtained in Preparation Example 19, was treated in a similar manner to Example 1, whereby the title compound was obtained (yield: 28%).

NMR (D$_2$O, δ): 1.25–1.47(6H,m), 3.17–3.29(4H,m), 3.25,3.51(2H,ABq,J=17.9 Hz), 4.55,4.78(2H,ABq, J=12.5 Hz), 5.07(1H,d,J=4.6 Hz), 5.70(1H,d,J=4.6 Hz), 6.82(1H,s)

EXAMPLE 8

Sodium 7-[(Z)-2-(2-aminothiazol-4-yl)-2-hydroxyiminoacetamido]-3-(1-azetidinyl)-carbonyloxymethyl-3-cephem-4-carboxylate

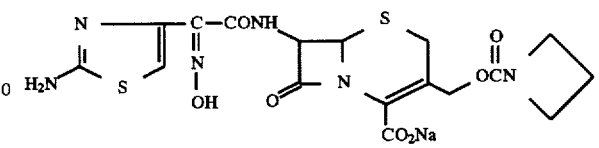

The compound, which had been obtained in Preparation Example 23, was treated in a similar manner to Example 1, whereby the title compound was obtained (yield: 25%).

NMR (D$_2$O, δ): 2.00–2.10(2H,m), 3.21,3.47(2H,ABq,J= 17.9 Hz), 3.75–3.87(4H,m), 4.51,4.70(2H,ABq,J=17.6 Hz), 5.05(1H,d,J=4.8 Hz), 5.68(1H,d,J=4.8 Hz), 6.78(1H,s)

EXAMPLE 9

Sodium 7-[(Z)-2-(2-aminothiazol-4-yl)-2-hydroxyiminoacetamido]-3-[N-(2-hydroxyethyl)-N-methylcarbamoyloxymethyl]-3-cephem-4-carboxylate

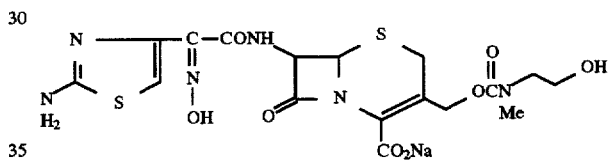

The compound, which had been obtained in Preparation Example 26, was treated in a similar manner to Example 1, whereby the title compound was obtained (yield: 8.8%).

NMR (D$_2$O, δ): 2.79–2.82(3H,m), 3.28–3.30(3H,m), 3.56–3.58 (3H,m), 4.57,4.75(2H,m), 5.09(1H,d,J=5 Hz), 5.73(1H,d,J=5 Hz), 6.84(1H,s)

EXAMPLE 10

Sodium 7-[(Z)-2-(2-aminothiazol-4-yl)-2-hydroxyiminoacetamido]-3-N-cyanomethyl-N-methylcarbamoyloxymethyl-3-cephem-4-carboxylate

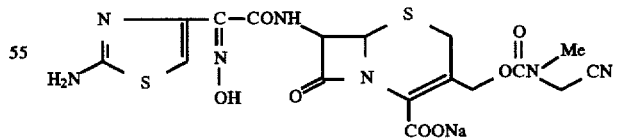

The compound, which had been obtained in Preparation Example 29, was treated in a similar manner to Example 1, whereby the title compound was obtained (yield: 21%).

NMR (D$_2$O, δ): 2.85(3H,br.s), 3.28,3.55(2H,ABq,J=18 Hz), 4.1–4.25(2H,m), 4.5–4.9(2H,m), 5.06(1H, d,J=5 Hz), 5.70(1H,d,J=5 Hz), 6.77(1H,s)

EXAMPLE 11

Sodium 7-[(Z)-2-(2-aminothiazol-4-yl)-2-hydroxyiminoacetamido]-3-[(3-hydroxy-1-pyrrolidinyl)carbonyloxymethyl-3-cephem-4-carboxylate

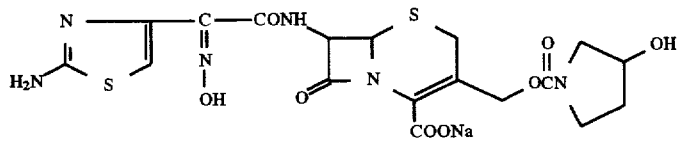

The compound, which had been obtained in Preparation Example 33, was treated in a similar manner to Example 1, whereby the title compound was obtained (yield: 17%).

NMR ($D_2O$, δ): 2.05(2H,m), 3.25–3.8(6H,m), 4.4–4.5 (1H, m), 4.6–4.95(2H,m), 5.20(1H,d,J=5 Hz), 5.83(1H,d, J=5 Hz), 6.96(1H,s)

EXAMPLE 12

Sodium 7-[(Z)-2-(2-aminothiazol-4-yl)-2-hydroxyiminoacetamido]-3-((S)-(+)-2-hydroxymethyl-1-pyrrolidinyl)carbonyloxymethyl-3-cephem-4-carboxylate

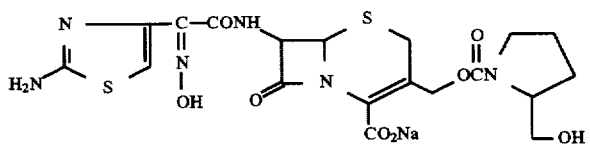

The compound, which had been obtained in Preparation Example 37, was treated in a similar manner to Example 1, whereby the title compound was obtained.

NMR ($D_2O$, δ): 1.70–1.84(4H,m), 3.19–3.82(7H,m), 4.67 (2H,ABq,J=13 Hz), 5.08(1H,d,J=4.8 Hz), 5.70 (1H,d,J=4.8 Hz), 6.83(1H,s)

EXAMPLE 13

Sodium 7-[(Z)-2-(2-aminothiazol-4-yl)-2-hydroxyiminoacetamido]-3-(1-pyrrolidinyl)-carbonyloxymethyl-3-cephem-4-carboxylate

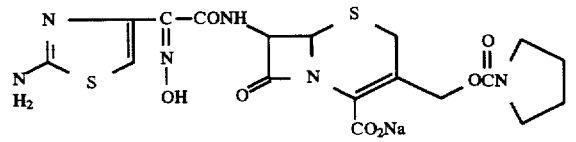

The compound, which had been obtained in Preparation Example 40, was treated in a similar manner to Example 1, whereby the title compound was obtained (17%).

NMR ($D_2O$, δ): 1.68–1.73(4H,m), 3.15–3.23(4H,m), 3.25, 3.52 (2H,ABq,J=18 Hz), 4.52,4.75(2H,ABq,J=12 Hz), 5.15(1H,d,J=4 Hz), 5.68(1H,d,J=4 Hz), 6.81(1H,s)

EXAMPLE 14

Pivaloyloxymethyl 7-[(Z)-2-(2-aminothiazol-4-yl)-2-hydroxyiminoacetamido]-3-N,N-dimethylcarbamoyloxymethyl-3-cephem-4-carboxylate

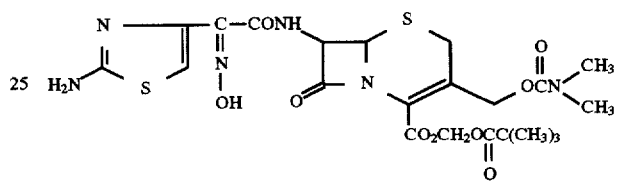

Iodomethyl pivalate (37 mg; 0.16 mmol) was added to a solution of sodium 7-[(Z)-2-(2-aminothiazol-4-yl)-2-hydroxyiminoacetamido]-3-N,N-dimethylcarbamoyloxymethyl-3-cephem-4-carboxylate (80 mg; 0.162 mmol), which had been obtained in Example 1, in dimethylformamide (2 ml), followed by stirring for one hour. After the reaction mixture was added with ethyl acetate (100 ml), the resulting mixture was washed with water and then with a saturated aqueous sodium chloride solution, followed by drying over anhydrous magnesium sulfate and then by concentration under reduced pressure. The residue was added with isopropyl ether and solidified, whereby the title compound was obtained (21 mg; yield: 23%).

NMR ($CDCl_3$, δ): 1.24(9H,s), 2.92(6H,br,s), 3.50,3.61 (2H, ABq, J=19 Hz), 4.89,5.17(2H,ABq,J=13 Hz), 5.07(1H, d, J=5 Hz), 5.85,5.97(1H,ABq,J=5.5 Hz), 5.93(1H,dd, J=5 Hz,8 Hz), 7.08(1H,s), 7.26(2H,s)

EXAMPLE 15

2-Ethylbutanoyloxymethyl 7-[(Z)-2-(2-aminothiazol-4-yl)-2-hydroxyiminoacetamido]-3-N,N-dimethylcarbamoyloxymethyl-3-cephem-4-carboxylate

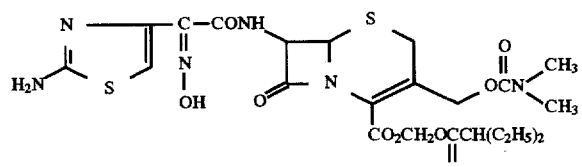

The compound obtained in Example 1 and iodomethyl 2-ethylbutyrate were reacted, whereby the title compound was obtained (yield: 63%).

NMR (CDCl₃, δ): 0.9(6H,t,J=7.4 Hz), 1.5–1.7(4H,m), 2.25–2.35(1H,m), 2.93(6H,br.s), 3.49,3.60(2H,ABq,J=18 Hz), 4.91,5.15 (2H,ABq,J=14 Hz), 5.07(1H,d,J=5.0 Hz), 5.84–5.95 (3H,m), 7.07(1H,s)

EXAMPLE 16

1-(Isobutyloyloxy)ethyl 7-[(Z)-2-(2-aminothiazol-4-yl)-2-hydroxyiminoacetamido]-3-N,N-dimethyl-carbamoyloxymethyl-3-cephem-4-carboxylate

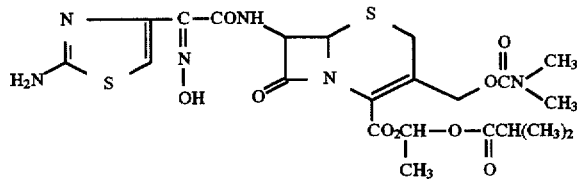

The compound obtained in Example 1 and 1-iodoethyl isobutyrate were reacted, whereby the title compound was obtained (yield: 10%).

NMR (CDCl₃, δ): 1.18(6H,d,J=7 Hz), 1.56(3H,d,J=5.5 Hz), 2.55–2.65(1H,m), 2.92(6H,s), 3.50,3.51(together, 1H,d,J=18 Hz), 3.61,3.62(together, 1H,d,J=18 Hz), 4.90, 4.95(together, 1H,d,J=14 Hz), 5.05,5.07 (together, 1H,d,J=5 Hz), 5.12,5.18(together, 1H,d,J=14 Hz), 5.88–5.95(1H,m), 7.00,7.10(together, 1H,q,J=5.5 Hz), 7.09(1H,s)

EXAMPLE 17

1-(2-Ethylbutanoyloxy)ethyl 7-[(Z)-2-(2-aminothiazol-4-yl)-2-hydroxyiminoacetamido]-3-N, N-dimethylcarbamoyloxymethyl-3-cephem-4-carboxylate

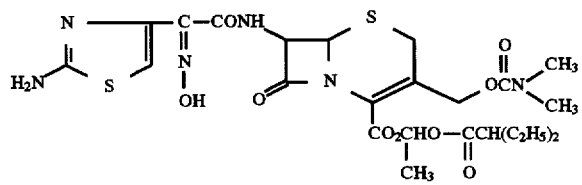

The compound obtained in Example 1 and 1-iodoethyl 2-ethylbutyrate were reacted, whereby the title compound was obtained (yield: 15%).

NMR (CDCl₃, δ): 0.90(3H,t,J=7 Hz), 0.91(3H,t,J=7 Hz), 1.5–1.75 (7H,m), 2.2–2.3(1H,m), 2.92(6H,s), 3.48,3.53 (1H, d,J=18 Hz), 3.60,3.61(1H,d,J=18 Hz), 4.90, 4.97(1H,d,J=14 Hz), 5.07(d,J=5 Hz), 5.14,5.15 (1H,d,J=14 Hz),.5.88–5.95 (1H,m), 7.00–7.10(1H,m), 7.08(1H,s)

EXAMPLE 18

1-(tert-Butylacetoxy)ethyl 7-[(Z)-2-(2-aminothiazol-4-yl)-2-hydroxyiminoacetamido]-3-N,N-dimethylcarbamoyloxymethyl-3-cephem-4-carboxylate

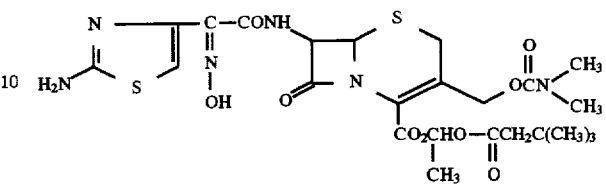

The compound obtained in Example 1 and 1-iodoethyl tert-butylacetate were reacted, whereby the title compound was obtained (yield: 4.5%).

NMR (CDCl₃, δ): 1.04(9H,s), 1.56(3H,d,J=5.5 Hz), 2.2–2.3 (2H,m), 2.93(6H,s), 3.48,3.50(together,1H,d, J=18 Hz), 3.60,3.61(together, 1H,d,J=18 Hz) 4.91,4.98(together, 1H,d,J=12 Hz), 5.03–5.10 (1H,m), 5.12,5.17(together, 1H,d, J=12 Hz), 5.86–5.93(1H,m), 6.97–7.12(1H,m), 7.12 (1H,s)

EXAMPLE 19

1-(Ethoxycarbonyloxy)ethyl 7-[(Z)-2-(2-aminothiazol-4-yl)-2-hydroxyiminoacetamido]-3-N, N-dimethylcarbamoyloxymethyl-3-cephem-4-carboxylate

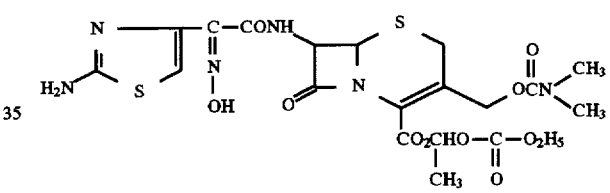

The compound obtained in Example 1 and 1-iodoethyl ethylcarbonate were reacted, whereby the title compound was obtained.

NMR (CDCl₃, δ): 1.33(3H,t,J=7 Hz), 1.58–1.63(3H,m), 2.93 (3H,br.s), 3.51(1H,d,J=18 Hz), 3.61,3.62(together, 1H,d, J=18 Hz), 4.2–4.32(2H,m), 4.91,5.17(1H,ABq,J=14 Hz), 4.99,5.22(1H,ABq,J=14 Hz), 5.05(0.5H,d,J=4.5 Hz), 5.10(0.5H,d,J=4.5 Hz), 5.9–5.98(1H,m), 6.92(0.5H,q, J=5.5 Hz), 7.04(0.5H,q,J=5.5 Hz),7.08(1H,s)

EXAMPLE 20

1-(Isopropyloxycarbonyloxy)ethyl 7-[(Z)-2-(2-aminothiazol-4-yl)-2-hydroxyiminoacetamido]-3-N, N-dimethylcarbamoyloxymethyl-3-cephem-4-carboxylate

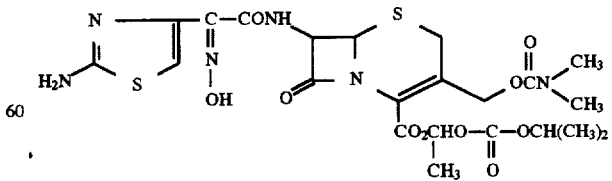

The compound obtained in Example 1 and 1-iodoethyl isopropylcarbonate were reacted, whereby the title compound was obtained (yield: 30%).

NMR (CDCl₃, δ): 1.26–1.37(6H,m), 1.58–1.62(3H,m), 2.93(6H,s), 3.50(1H,d,J=19 Hz), 3.60,3.61(together,1H,d,J= 19 Hz), 4.9–5.24(3H,m), 5.04,5.07(together, 1H,d,J=5 Hz), 5.93(1H,dd,J=5 Hz,8 Hz), 6.92,7.02(together,1H,q, J=5.5 Hz), 7.08(1H,s)

EXAMPLE 21

1-(Cyclohexylcarbonyloxy)ethyl 7-[(Z)-2-(2-aminothiazol-4-yl)-2-hydroxyiminoacetamido]-3-N,N-dimethylcarbamoyloxymethyl-3-cephem-4-carboxylate

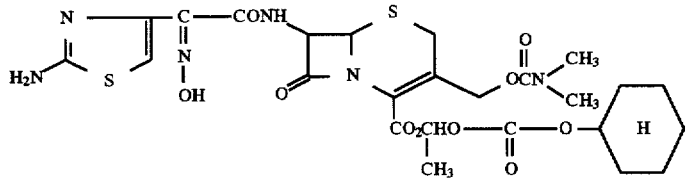

The compound obtained in Example 1 and 1-iodoethyl cyclohexylcarbonate were reacted, whereby the title compound was obtained (yield: 19%).

NMR (CDCl₃, δ): 1.1–1.6(6H,m), 1.58–1.63(3H,m), 1.66–2.00(4H,m), 2.93(6H,s), 3.52,3.40(2H,ABq,J=18 Hz), 4.6–4.7 (1H,m), 4.89,4.97(together,1H,d,J=12 Hz), 5.05–5.10(1H,m), 5.12, 5.17(together, 1H,d,J=12 Hz), 6.83–6.94(1H,m), 6.89,6.98(together, 1H,q,J=5.5 Hz), 7.15 (1H,s)

EXAMPLE 22

Pivaloyloxymethyl 7-[(Z)-2-(2-aminothiazol-4-yl)-2-hydroxyiminoacetamido]-3-N-ethyl-N-methylcarbamoyloxymethyl-3-cephem-4-carboxylate

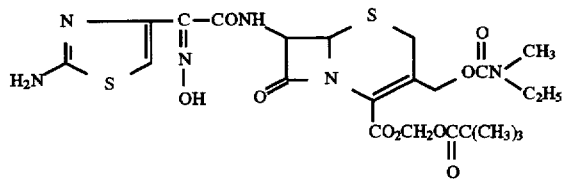

The compound obtained in Example 2 and iodomethyl pivalate were reacted, whereby the title compound was obtained (yield: 34%).

NMR (CDCl₃, δ): 1.12(3H,t,J=7 Hz), 1.24(9H,s), 2.89 (⅔H,s),2.90 (⅓H,s), 3.25–3.35(2H,m), 3.47,3.48(together, 1H,d,J=18 Hz), 3.61(1H,d,J=18 Hz),4.89(1H,d,J=13 Hz), 5.06(1H,d,J=5 Hz), 5.1–5.2(1H,m), 5.82,5.97 (1H,ABq,J=5 Hz), 5.92(1H,dd,J=5 Hz,8 Hz), 7.07(1H,s)

EXAMPLE 23

Pivaloyloxymethyl 7-[(Z)-2-(2-aminothiazol-4-yl)-2-hydroxyiminoacetamido]-3-(1-morpholinyl)carbonyloxymethyl3-cephem-4-carboxylate

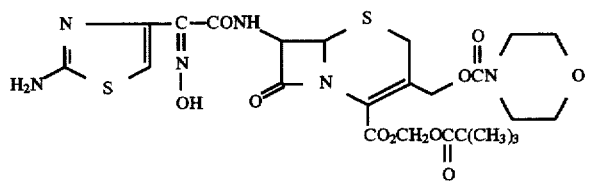

The compound obtained in Example 3 and iodomethyl pivalate were reacted, whereby the title compound was obtained (yield: 24%).

NMR (CDCl₃, δ): 3.45–3.50(5H,m), 3.58–3.70(5H,m), 4.89,5.18 (2H,ABq,J=12 Hz), 5.07(1H,d,J=5 Hz), 5.84,5.97 (2H,ABq,J=5 Hz), 5.93(1H,dd,J=5 Hz,8 Hz), 7.08(1H,s)

EXAMPLE 24

Pivaloyloxymethyl 7-[(Z)-2-(2-aminothiazol-4-yl)-2-methoxyiminoacetamido]-3-N,N-dimethylcarbamoyloxymethyl-3-cephem-4-carboxylate

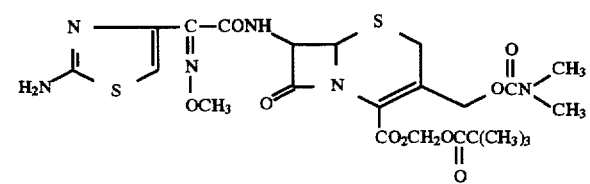

The compound obtained in Example 4 and iodomethyl pivalate were reacted, whereby the title compound was obtained (yield: 65%).

NMR (CDCl₃, δ): 1.23(9H,s), 2.92(6H,s), 3.50,3.60(2H, ABq,J=18.7 Hz), 4.09(3H,s), 4.84,5.16(2H,ABq,J=14 Hz), 5.09(1H,d, J=4.8 Hz), 5.85–5.95(2H,m), 5.99–6.03(1H,m), 6.92(1H,s), 7.49(1H,d,J=7.5 Hz)

EXAMPLE 25

Pivaloyloxymethyl 7-[(Z)-2-(5-amino-1,2,4-thiazol-3-yl)-2-methoxyiminoacetamido]-3-N,N-dimethylcarbamoyloxymethyl-3-cephem-4-carboxylate

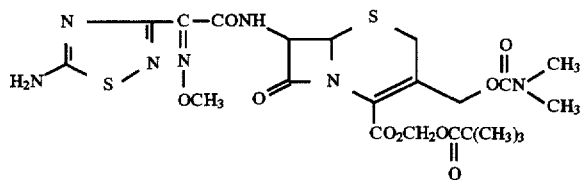

The compound obtained in Example 5 and iodomethyl pivalate were reacted, whereby the title compound was obtained (yield: 70%).

NMR (CDCl$_3$, δ): 1.13(9H,s), 2.92(6H,s), 3.50,3.59(2H, ABq,J=18.6 Hz), 4.12(3H,s), 4.84,5.19(2H,ABq,J=13.7 Hz), 5.10(1H,d, J=4.8 Hz), 5.85–5.94(2H,m), 6.12–6.16(1H, m), 6.42(1H,s)

EXAMPLE 26

Pivaloyloxymethyl 7-[(Z)-2-2-aminothiazol-4-yl)-2-monofluoromethoxyaminoacetamido]-3-N,N-dimethylcarbamoyloxymethyl-3-cephem-4-carboxylate

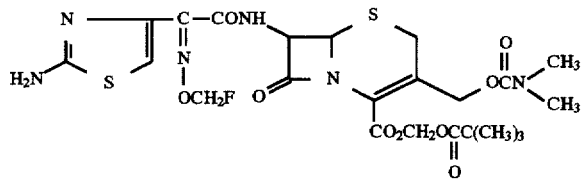

The compound obtained in Example 6 and iodomethyl pivalate were reacted, whereby the title compound was obtained (yield: 70%).

NMR (CDCl$_3$, δ): 1.14(9H,s), 2.91(6H,s), 3.50,3.60(2H, ABq,J=18.4 Hz), 4.85,5.16(2H,ABq,J=14.2 Hz), 5.10(1H,d, J=4.8 Hz), 5.65–6.00(3H,m),5.86,5.93(2H,ABq,J=5.5 Hz), 6.98(1H,s)

EXAMPLE 27

Pivaloyloxymethyl 7-[(Z)-2-(2-aminothiazol-4-yl)-2-hydroxyiminoacetainido]-3-(1-piperidinyl)-carbonyloxymethyl-3-cephem-4-carboxylate

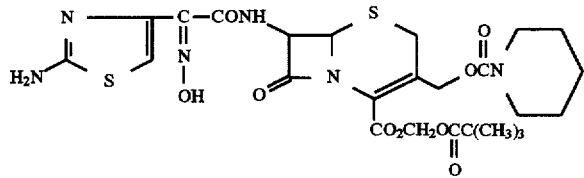

The compound obtained in Example 7 and iodomethyl pivalate were reacted, whereby the title compound was obtained (yield: 59%).

NMR (CD$_3$OD, δ): 1.13(9H,s), 1.48–1.66(6H,m), 3.37–3.46(4H,m), 3.54,3.69(2H,ABqJ=18.4 Hz), 4.77,5.13 (2H,ABq, J=13.4 Hz), 5.20(1H,dJ=4.9 Hz), 5.84,5.93(2H, ABq, J=6 Hz), 5.92(1H,d,J=4.9 Hz), 6.76(1H,s)

EXAMPLE 28

Pivaloyloxymethyl 7-[(Z)-2-(2-aminothiazol-4-yl)-2-hydroxyiminoacetamido]-3-(1-azetidinyl)-carbonyloxymethyl-3-cephem-4-carboxylate

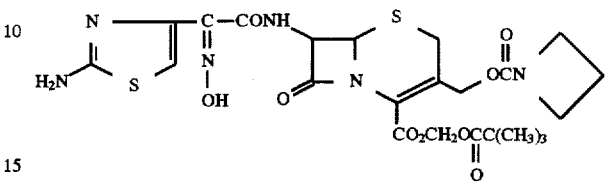

The compound obtained in Example 8 and iodomethyl pivalate were reacted, whereby the title compound was obtained (yield: 54%).

NMR (CDCl$_3$, δ): 2.24–2.30(2H,m), 3.47,3.60(2H,ABq, J=18.4 Hz), 3.95–4.10(4H,m), 4.87,5.12(2H,ABq,J=14.1 Hz), 5.06(1H, d,J=5.1 Hz), 5.91(2H,ABq,J=5.6 Hz), 5.90–5.93(1H,m), 7.07(1H,s)

EXAMPLE 29

1-(Isopropyloxycarbonyloxy)ethyl 7-[(Z)-2-(2-aminothiazol-4-yl)-2-hydroxyiminoacetamido]-3-(1-azetidinyl)carbonyloxymethyl-3-cephem-4-carboxylate

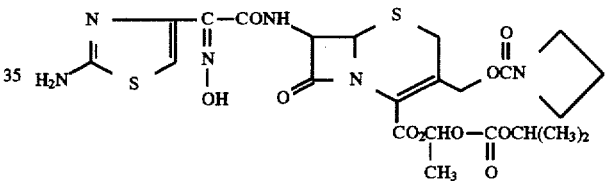

The compound obtained in Example 8 and iodoethyl isopropylcarbonate were reacted, whereby the title compound was obtained (yield: 27%).

NMR (CDCl$_3$, δ): 1.30–1.35(6H,m), 2.22–2.31(2H,m), 3.45–3.65(2H,m), 4.00–4.06(4H,m), 4.89–5.20(4H,m), 5.90–5.93(1H,m), 6.92(½H,q,J=5.5 Hz), 7.03(½H,q,J=5.5 Hz), 7.08 (1H, s

EXAMPLE 30

Pivaloyloxymethyl 7-[(Z)-2-(2-aminothiazol-4-yl)-2-hydroxyiminoacetamido]-3-N-(2-hydroxyethyl)-N-methylcarbamoyloxymethyl-3-cephem-4-carboxylate

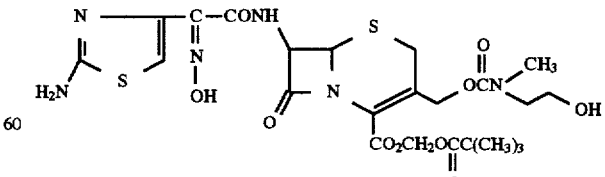

The compound obtained in Example 9 and iodomethyl pivalate were reacted, whereby the title compound was obtained (yield: 57%).

NMR (CDCl₃, δ): 1.21–1.25(9H,m), 2.97(3H,s), 3.41–3.45(2H,m), 3.46–3.60(2H,m), 3.71–3.77(2H,m), 4.82–4.95(2H,m), 5.05–5.08(1H,m),5.86,5.95(2H,ABq,J=6 Hz), 5.88–5.91 (1H, m), 7.00(1H,s)

EXAMPLE 31

1-Cyclohexyloxycarbonyloxyethyl 7-[(Z)-2-(2-aminothiazol-4-yl)-2-hydroxyiminoacetamido]-3-N-(2-hydroxyethyl)-N-methylcarbamoyloxymethyl-3-cephem-4-carboxylate

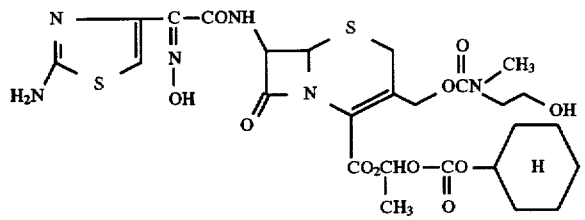

The compound obtained in Example 9 and 1-iodoethyl cyclohexylcarbonate were reacted, whereby the title compound was obtained (yield: 28%).

NMR (CDCl₃, δ): 1.4–1.6(6H,m),1.62–1.72(3H,m), 1.83–1.92(4H,m), 2.93(3H,s), 3.38–3.41(2H,m),3.42–3.50 (2H,m), 3.70–3.75(2H,m), 4.57–4.61(1H,m), 4.99(1H,q,J=5 Hz), 5.05–5.14(2H,m), 5.82–5.86(1H,m), 6.85,6.96(1H, ABq, J=5 Hz), 6.99(1H,s)

EXAMPLE 32

Pivaloyloxymethyl 7-[(Z)-2-(2-aminothiazol-4-yl)-2-hydroxyiminoacetamido]-3-N-cyanomethyl-N-methylcarbamoyloxymethyl-3-cephem-4-carboxylate

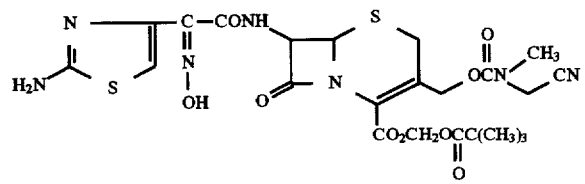

The compound obtained in Example 10 and iodomethyl pivalate were reacted, whereby the title compound was obtained (yield: 70%).

NMR (CDCl₃, δ): 1.1–1.25(9H,m),3.01(3H,s), 3.4–3.65 (2H,m), 4.2–4.3(2H,m), 4.8–5.25(3H,m),5.8–6.0(3H,m), 6.90(1H, br.s), 7.30(2H,s)

EXAMPLE 33

Pivaloyloxymethyl 7-[(Z)-2-(2-aminothiazol-4-yl)-2-hydroxyiminoacetamido]-3-[(S)-(+)-2-hydroxymethyl-1-pyrrolidinyl]carbonyloxymethyl-3-cephem-4-carboxylate

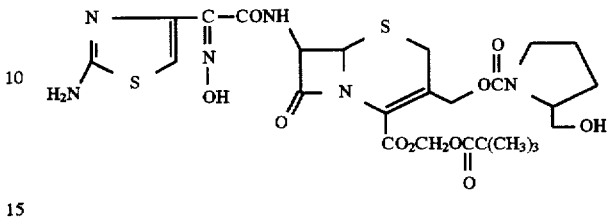

The compound obtained in Example 12 and iodomethyl pivalate were reacted, whereby the title compound was obtained.

NMR (CD₃OD, δ): 1.83–2.00(4H,m), 3.30–3.87(7H,m), 5.01(2H,ABq, J=14 Hz), 5.20(1H,d,J=4.8 Hz), 5.84 (1H,d, J=4.8 Hz), 5.91–5.94(2H,m), 6.76(1H,s)

EXAMPLE 34

Pivaloyloxymethyl 7-[(Z)-2-(2-aminothiazol-4-yl)-2-hydroxyiminoacetamido]-3-(1-pyrrolidinyl)-carbonyloxymethyl-3-cephem-4-carboxylate

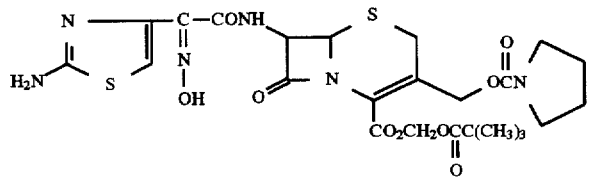

The compound obtained in Example 13 and iodomethyl pivalate were reacted, whereby the title compound was obtained (yield: 28%).

NMR (CDCl₃, δ): 1.16–1.21(9H,m), 1.80–1.85(4H,m), 3.30–3.39(4H,m), 3.50–3.60(2H,m), 4.80–4.90,5.05,5.13 (2H,m), 5.02–5.04(1H,m),5.75–5.80(2H,m), 5.85–5.91(1H, m), 6.98 (1H,s)

EXAMPLE 35

1-Acetoxyethyl 7-[(Z)-2-(2-aminothiazol-4-yl)-2-hydroxyiminoacetamido]-3-N,N-dimethylaminocarbonyloxymethyl-3-cephem-4-carboxylate

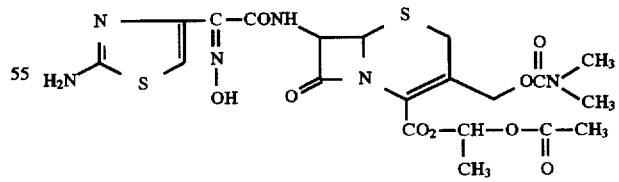

The compound obtained in Example 1 and 1-bromoethyl acetate were reacted, whereby the title compound was obtained (yield: 14%).

NMR (CDCl₃, δ): 1.55–1.58(3H,m), 2.11(3H,d,J=4.6 Hz), 2.92–2.95 (3H,s), 3.47–3.65(2H,m), 4.83–5.24(3H,m), 5.83–5.94(1H,m), 6.98–7.15(2H,m)

EXAMPLE 36

1-(Cyclohexyloxycarbonyloxy)ethyl 7-[(Z)-2-(2-aminothiazol-4-yl)-2-hydroxyiminoacetamido]-3-(1-azetidinyl)carbonyloxymethyl-3-cephem-4-carboxylate

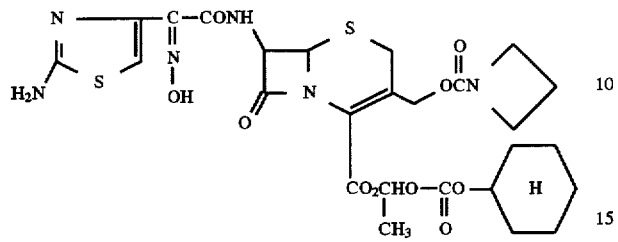

The compound obtained in Example 8 and 1-iodoethyl cyclohexylcarbonate were reacted, whereby the title compound was obtained (yield: 27%).

NMR (CDCl$_3$, δ): 1.24(3H,d,J=7.2 Hz), 1.75–1.80(10H, m),2.25–2.32(2H,m), 3.45–3.65(2H,m), 4.00–4.06(4H,m), 4.91,4.98(1H,ABq,J=13.8 Hz), 5.03–5.07(1H,m), 5.10–5.13 (1H,m), 5.09,5.18(1H,ABq,J=13.8 Hz), 5.90–5.93(1H,m), 6.93(½H,q,J=5.5 Hz), 7.03(½H,q,J=5.5 Hz), 7.08(1H,s)

EXAMPLE 37

1-Acetoxyethyl7-[(Z)-2-(2-aminothiazol-4-yl)-2-hydroxyiminoacetamido]-3-(1-azetidinyl)carbonyl-oxymethyl-3-cephem-4-carboxylate The compound obtained in Example 8 and 1-bromoethyl acetate were reacted, whereby the title compound was obtained.

NMR (CDCl$_3$, δ): 1.54–1.56(3H,m), 2.10–2.21(3H,m), 2.20–2.35(2H,m), 3.45–3.65(2H,m), 3.95–4.08(4H,m), 4.85–4.95(1H,m), 5.05–5.1(2H,m), 5.87–5.95(1H,m), 6.97–7.17(2H,m)

PREPARATION EXAMPLE 41

Benzhydryl 7-phenylacetamido-3-p-nitrophenoxy-carbonyloxymethyl-3-cephem-4-carboxylate To a suspension of benzhydryl 7-phenylacetamide-3-hydroxymethyl-3-cephem-4-carboxylate (15.8 g; 0.031 mol) and p-nitrophenylchloroformate (6.19 g; 0.031 mol) in tetrahydrofuran (160 ml), pyridine (2.43 g; 0.031 mol) was added dropwise under ice cooling, followed by stirring at the same temperature for 25 minutes.

The reaction mixture was poured into a mixed solvent of ethyl acetate and water and the ethyl acetate layer was collected. The resulting ethyl acetate layer was washed with a saturated aqueous sodium chloride solution and dried over magnesium sulfate. Then, the solvent was distilled off under reduced pressure. The residue was added with diisopropyl ether and triturated. The resulting mixture was filtered so that the solid was collected. The solid was dried in air, whereby benzhydryl 7-phenylacetamido-3-p-nitrophenoxycarbonyloxymethyl-3-cephem-4-carboxylate was obtained (yield: 18.8 g; 90.2%).

NMR (CDCl$_3$, δ): 3.40,3.60(2H,ABq,J=18.5 Hz), 3.61, 3.66(2H,ABq, =13.6 Hz), 4.97(1H,d,J=8.8 Hz), 4.97,5.24 (2H,ABq,J=13.2 Hz), 5.88(1H,dd,J=4.9 Hz,8.8 Hz), 6.30 (1H,d,J=8.8 Hz), 6.92(1H,s), 7.24–7.42(17H,m), 8.23–8.28 (2H,m)

PREPARATION EXAMPLE 42

7-Phenylacetamido-3-p-nitrophenoxycarbonyloxymethyl-3-cephem-4-carboxylic acid

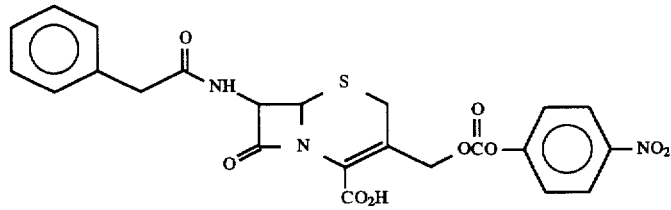

To a solution of benzhydryl 7-phenylacetamido-3-p-nitrophenoxycarbonyloxymethyl-3-cephem-4-carboxylate (6.79 g, 0.01 mol) in dichloromethane (14 ml), trifluoroacetic acid (17 ml) was added dropwise under ice cooling, followed by stirring for 50 minutes. The reaction mixture was poured into diisopropyl ether. The precipitate thus obtained was collected by filtration, washed with diisopropyl ether and dried in air, whereby 7-phenylacetamido-3-p-nitrophenoxycarbonyloxymethyl- 3-cephem-4-carboxylic acid was obtained (yield: 4.50 g; 87.7%).

NMR (DMSO, δ): 3.49,3.57(2H,ABq,J=14.0 Hz), 3.60, 3.71(2H,ABq, =18.1 Hz), 4.95,5.24 (2H,ABq,J=12.5 Hz), 5.12(1H,d, J=4.9 Hz), 5.72(1H,dd,J=4.9,8.6 Hz), 7.19–7.28 (5H,m), 7.53–7.58(2H,m), 8.28–8.35(2H,m), 9.12(1H,d,J= 8.6 Hz)

PREPARATION EXAMPLE 43

Sodium 7-phenylacetamido-3-N,N-dimethylcarbamoyl-oxymethyl-3-cephem-4-carboxylate

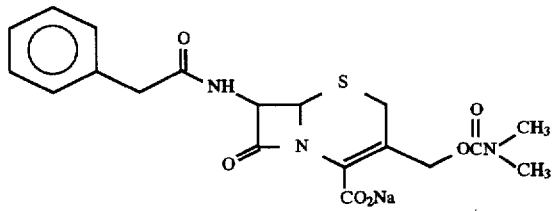

To a solution of benzhydryl 7-phenylacetamide-3-p-nitrophenoxycarbonyloxymethyl-3-cephem-4-carboxylate (5.13 g, 0.01 mol) in tetrahydrofuran (36 ml) and water (4 ml), a 50% aqueous solution of dimethylamine (1.8 g; 0.02 mol) was added dropwise under ice cooling. At the same temperature, the resulting solution was stirred for 10 minutes. The reaction mixture was poured into a mixture of ethyl acetate and 1N hydrochloric acid and an organic layer was collected. The organic layer was washed successively with water and a saturated aqueous sodium chloride solution, followed by drying over magnesium sulfate. The solvent was distilled off under reduced pressure. The residue was suspended in methanol and the resulting suspension was added with a solution of sodium acetate (984 mg; 0.012 mol) in methanol. The first solution thus obtained was concentrated under reduced pressure. The concentration was stopped when a precipitate had appeared. After the addition of 2-propanol, the precipitate was collected by filtration and dried in air, whereby sodium 7-phenylacetamido-3-N,N-dimethylcarbamoyloxymethyl-3-cephem-4-carboxylate was obtained (yield: 2.25 g; 51.0%).

NMR (D$_2$O, δ): 2.74(6H,s), 3.21,3.47(2H,ABq,J=17.9 Hz), 3.51,3.57 (2H,ABq,J=14.8 Hz), 4.51,4.74 (2H,ABq,J= 12.6 Hz), 4.92(1H,d,J=4.6 Hz), 5.48(1H,d,J=4.6 Hz), 7.18–7.28(5H,m)

PREPARATION EXAMPLE 44

1-(Isopropoxycarbonyloxy)ethyl 7-phenylacetamido-3-N,N-dimethylcarbamoyloxymethyl-3-cephem-4-carboxylate

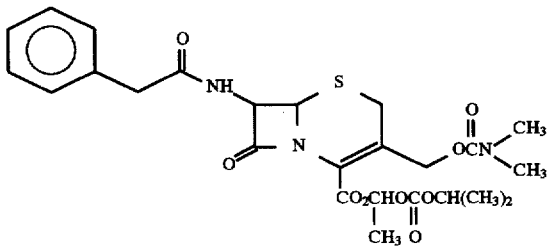

To a solution of sodium 7-phenylacetamido-3-N,N-dimethylcarbamoyloxymethyl-3-cephem-4-carboxylate (2.2 g; 5 mmol) in N,N-dimethylformamide (20 ml), isopropyl-1-iodoethylcarbonate (1.29 g; 5 mmol) was added under ice cooling, followed by stirring at the same temperature for 30 minutes. The reaction mixture was poured into a mixture of ethyl acetate and water and the ethyl acetate layer was collected. The ethyl acetate layer was successively washed with water and a saturated aqueous sodium chloride solution, followed by drying over magnesium sulfate. Then, the solvent was distilled off under reduced pressure. The residue was purified by chromatography on a silica gel column, whereby 1-(isopropoxycarbonyloxy)ethyl 7-phenylacetamido-3-N,N-dimethylcarbamoyloxymethyl-3-cephem-4-carboxylate was obtained (yield: 1.43 g; 52.1%).

NMR (CDCl$_3$, δ): 1.22–1.29(6H,m), 1.26(3H,d,J=5.5 Hz, 2.85(6H,s), 3.35,3.48(1H,ABq,J=18.4 Hz), 3.36,3.49(1H, ABq, J=18.4 Hz), 3.55(2H,s), 4.75–4.88(3H,m), 5.04,5.10 (2H,ABq,J=13.9 Hz), 5.71–5.76(1H,m), 6.77–6.82 (1H,m), 6.91(0.5H,q,J=5.5 Hz), 6.94(0.5H,d,J=8.9 Hz), 7.19–7.29 (5H,m)

EXAMPLE 38

Benzhydryl 7-formamido-3-N,N-dimethylcarbamoyl-oxymethyl-3-cephem-4-carboxylate

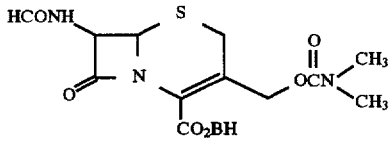

To a solution of trichloromethylchloroformate (0.3 ml; 2.5 mmol) in tetrahydrofuran (10 ml), a solution of benzhydryl 7-formamido-3-hydroxymethyl-3-cephem-4-carboxylate (2.12 g; 5 mmol) and pyridine (0.395 g; 5 mmol) in tetrahydrofuran (15 ml) was added under ice cooling. After 70 minutes, the resulting solution was added dropwise with a tetrahydrofuran solution (1 ml) containing dimethylamine (0.45 g; 5 mmol) dissolved therein, followed by stirring for 25 minutes. The reaction mixture was added with ethyl acetate (50 ml). The organic layer was washed with water, dried over magnesium sulfate and concentrated under reduced pressure. The residue thus obtained was purified by chromatography on a silica gel column, whereby the target compound was obtained (yield: 1.1 g; 44%).

NMR (CDCl$_3$, δ): 2.82(3H,s), 2.88(3H,s), 3.42,3.57(2H, ABq,J=18.4 Hz), 4.82,5.09(2H,ABq,J=13.9 Hz), 4.97(1H,d, J=4.8 Hz), 5.91(1H,dd,J=4.8 Hz,9.3 Hz), 6.66(1H,d,J=9.3 Hz), 6.94(1H,s), 7.25,7.45(10H,m), 8.20(1H,s)

EXAMPLE 39

7-Amino-3-N,N-dimethylcarbamoyloxymethyl-3-cephem-4-carboxylic acid

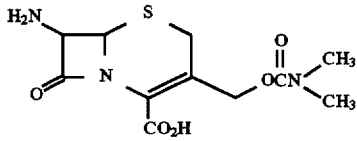

Sodium 7-formamido-3-N,N-dimethylcarbamoyl-oxymethyl-3-cephem-4-carboxylate (5.0 g; 14.25 mmol) was dissolved in methanol (45 ml). To the resulting solution, a methanol solution (30 ml) containing concentrated hydrochloric acid (10 ml) dissolved therein was added at room temperature. After stirring for three hours, the reaction mixture was concentrated under reduced pressure. The concentrate was added with water (50 ml). Under ice cooling, the resulting solution was controlled to pH 2.8 with a 1N caustic soda solution. A precipitate thus formed was collected by filtration, whereby the title compound was obtained (yield: 1.82 g; 42%).

NMR (DMSO-d6, δ): 2.81(3H,s), 2.82(3H,s), 3.45,3.58 (2H,ABq,J=18.1 Hz), 4.60,4.98(2H,ABq,J=13.0 Hz), 4.77–4.80(1H,m), 4.97–5.00(1H,m)

EXAMPLE 40

1-(Isopropoxycarbonyloxy)ethyl 7β-[2-(2-aminothiazol-4-yl)-2-(Z)-acetoxyiminoacetamido]-3-N,N-dimethylcarbamoyloxymethyl-3-cephem-carboxylate hydrochloride

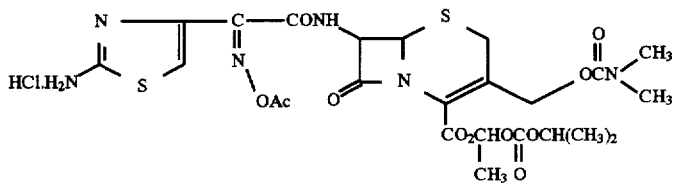

In tetrahydrofuran (440 ml), 1-(isopropoxycarbonyloxy) ethyl 7-amino-3-N,N-dimethylcarbamoyloxymethyl-3-cephem-carboxylate hydrochloride (22 g; 47 mmol) was dissolved, to which N,O-bistrimethylsilylacetamide (35 ml) was added.

To the resulting solution, 2-(2-aminothiazol-4-yl)-2-(Z)-acetoxyiminoacetic chloride hydrochloride (15.8 g) was gradually added under ice cooling.

The reaction mixture was heated tack to room temperature, at which it was stirred for 30 minutes. The reaction mixture was added with ethyl acetate (600 ml), water (40 ml) and saturated aqueous sodium chloride solution (25 ml) and the organic layer was collected. The organic layer was then washed with saturated aqueous sodium chloride solution-and dried over anhydrous magnesium sulfate. The solvent was distilled off under reduced pressure, whereby the title compound was obtained (yield: 31.5 g; 99%).

NMR (CD$_3$OD, δ): 1.27–1.29(6H,m), 1.54(3H,d,J=5.5 Hz), 2.23(3H,s), 2.92(6H,d,J=8.4 Hz), 3.60(1H,d,J=18 Hz), 3.74(1H, dd,J=9 Hz,18 Hz), 4.81–5.16(3H,m), 5.22(1H,dd, J=5 Hz,12 Hz), 5.97(1H,dd,5 Hz,15 Hz), 6.85(0.5H,dd, J=5 Hz,10 Hz), 6.94(0.5 Hz,dd,J=5 Hz,10 Hz), 7.19(1H,s)

EXAMPLE 41

1-(Isopropoxycarbonyloxy)ethyl 7β-[2-(2-aminothiazol-4-yl)-2-(Z)-hydroxyiminoacetamido]-3-N,N-dimethylcarbamoyloxymethyl-3-cephem-carboxylate hydrochloride

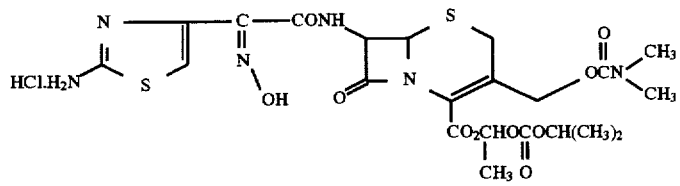

In methanol (108 l), 1-(isopropoxycarbonyloxy)-ethyl 7β-[2-(2-aminothiazol-4-yl)-2-(Z)-acetoxyiminoacetamido]-3-N,N-dimethylcarbamoyloxymethyl-3-cephem-carboxylate (10.8 g; 15.9 mmol), which had been obtained in Example 40, was dissolved, to which concentrated hydrochloric acid (8.6 ml) was added dropwise under ice cooling. After the dropwise addition was completed, the resulting solution was stirred at room temperature for 3 hours. The reaction mixture was added with ethyl acetate (540 ml). The organic layer was washed with water, dried over magnesium sulfate, and then concentrated under reduced pressure. The residue was added with isopropyl ether and the resulting solid was collected by filtration, whereby the title compound was obtained (yield: 8 g; 80%).

The compound obtained in this Example conformed in HPLC. and TLC. data with the compound obtained in Example 20.

NMR (CD$_3$OD, δ): 1.27 1.29(6H,m), 1.54(3H,d,J=5.5 Hz), 2.91(3H,s), 2.93(3H,s), 3.57.3.67(1H,ABq,J=14.7 Hz), 3.57,3.69 (1H,ABq,J=14.7 Hz), 4.78 4.9(2H,m), 5.06(0.5H, d, J=13.6 Hz), 5.17(0.5 Hz,d,J=13.4 Hz), 5.19(0.5H,d, J=5 Hz), 5.22(0.5H,d,J=5 Hz), 5.91(0.5H,d,J=5 Hz), 5.95(0.5H, d,J=5 Hz), 6.85(0.5H,q,J=5.5 Hz), 6.94(0.5H,q,J=5.5 Hz), 6.97(1H,s)

EXAMPLE 42

7β-[2-(2-Aminothiazol-4-yl)-2-(Z)-acetoxyimino-acetamido ]-3-N,N-dimethylcarbamoyloxymethyl-3-cephem-carboxylic acid

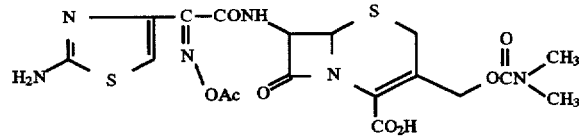

In ethyl acetate (4 ml), 7-amino-3-N,N-dimethylcarbamoyloxymethyl-3-cephem-4-carboxylic acid (0.2 g; 0.66 mmol) was suspended. To the suspension, N,O-bistrimethylsilylacetamide (0.49 ml) was added and dissolved.

To the resulting solution, 2-(2-aminothiazol-4-yl)-2-(Z)-acetoxyiminoacetic acid chloride hydrochloride (0.189 g; 0.664 mmol) was added gradually under ice cooling.

The reaction mixture was heated back to room temperature, at which it was stirred for 30 minutes. Methanol (0.2 ml) was added to the resulting solution, followed by concentration under reduced pressure. The residue thus obtained was purified by reversed phase column chromatography, whereby the title compound was obtained (yield: 138 mg; 41%).

EXAMPLE 43

1-(Isopropoxycarbonyloxy)ethyl 7β-[2-(2-aminothiazol-4-yl)-2-(Z)-acetoxyiminoacetamido]-3-N,N-dimethylcarbamoyloxymethyl-3-cephem-carboxylate

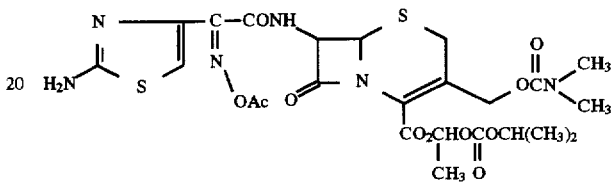

In ethyl acetate (30 ml), 7β-[2-(2-aminothiazol-4-yl)-2-(Z)-acetoxyiminoacetamido]-3-N,N-dimethylcarbamoyloxymethyl-3-cephem-carboxylic acid (2.17 g; 4.24 mmol), which had been obtained above, was dissolved. To the resulting solution, dicyclohexylamine (1.35 ml) was added and the resulting precipitate was collected by filtration. Dicyclohexylamine salt thus obtained (1.7 g; 2.45 mmol) was dissolved in N,N-dimethylacetamide (10 ml). To the resulting solution, 1-iodoethylisopropyl carbonate (758 mg; 2.94 mmol) was added under ice cooling, followed by stirring for one hour. The reaction mixture was added with ethyl acetate, washed with water and then dried over magnesium sulfate. After concentration under reduced pressure, the concentrate was added with isopropyl ether and the resulting solid was collected by filtration, whereby the title compound was obtained. The compound obtained in this Example conformed in HPLC. and TLC. data with the compound obtained in Example 40.

EXAMPLE 44

Sodium 7β-[2-(2-aminothiazol-4-yl)-2-(Z)-hydroxyiminoacetamido]-3-N,N-dimethylcarbamoyloxymethyl-3-cephem-carboxylate

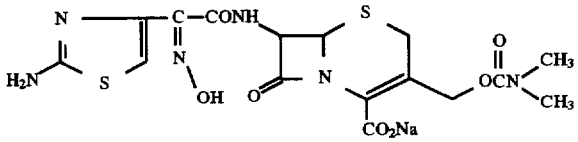

In ethyl acetate (10 ml), 7-amino-3-N,N-dimethylcarbamoyloxymethyl-3-cephem-4-carboxylic acid (0.5 g; 1.66 mmol) was suspended. To the suspension, N,O-bistrimethylsilylacetamide (1.23 ml) was added and dissolved.

To the resulting solution, 2-(2-aminothiazol-4-yl)-2-(Z)-acetoxyiminoacetic acid chloride hydrochloride (0.52 g; 1.83 mmol) was gradually added under ice cooling.

The reaction mixture was heated back to room temperature, at which it was stirred for 30 minutes. Then, methanol (0.5 ml) and ethyl acetate (10 ml) were added to the reaction mixture and the precipitate thus obtained was collected by filtration. The resulting precipitate was dissolved in methanol (5 ml), followed by the addition of concentrated hydrochloric acid (0.5 ml) and then by stirring for 30 minutes. After concentration, the reaction mixture was controlled to pH 7 with an aqueous sodium hydrogencarbonate solution and then purified by reversed phase column chromatography, whereby the title compound was obtained (yield: 349 mg; 50%).

The compound in this example conformed with the compound obtained in Example 1 in physicochemical properties such as N.M.R. spectrum, HPLC and TLC.

PREPARATION EXAMPLE 45

Benzhydryl 7-[(Z)-2-(2-tritylaminothiazol-4-yl)-2-trityloxyiminoacetamido]-3-N-methylcarbamoyloxymethyl-3-cephem-4-carboxylate

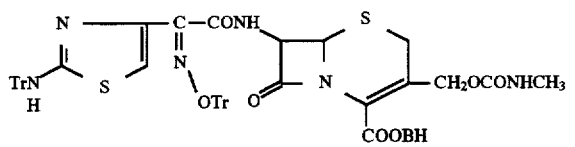

Added to benzhydryl were 7-formamido-3-monomethylcarbamoyloxymethyl-3-cephem-4-carboxylate (3.54 g), tetrahydrofuran (40 ml) and methanol (40 ml). Then, the resulting solution was added with concentrated hydrochloric acid (3.6 ml) at room temperature, followed by stirring at the same temperature for 3 hours. The reaction mixture was concentrated under reduced pressure. The residue obtained was diluted with ethyl acetate, followed by washing with a saturated aqueous solution of sodium bicarbonate and a saturated aqueous sodium chloride solution and then by drying over anhydrous magnesium sulfate. The solvent was then distilled off.

At room temperature, the residue thus obtained was added with a solution which had separately been obtained by adding 2-trityloxyimino-2-(2-tritylaminothiazol-4-yl)acetic acid (4.9 g), dicyclohexylcarbodiimide (1.52 g) and 1-hydroxy-1H-benztriazole (1.0 g) to tetrahydrofuran (30 ml) and stirring them for 30 minutes. After the resulting solution was stirred overnight at room temperature, the reaction mixture was filtered. The filtrate was diluted with an aqueous solution of ethyl acetate. The diluted filtrate was washed further with 1N hydrochloric acid, saturated aqueous sodium bicarbonate solution and saturated aqueous sodium chloride solution, followed by drying over anhydrous magnesium sulfate. The solvent was then distilled off. The residue thus obtained was purified by column chromatography (SiO$_2$; benzene:ethyl acetate=6:1), whereby the title compound was obtained (yield: 5.39 g; 66%).

NMR (CDCl$_3$, δ): 2.75(3H,d,J=5 Hz), 3.25,3.52(2H,ABq, J=18 Hz), 4.40(1H,d,J=5 Hz), 4.77,5.07(2H,ABq,J=14 Hz), 5.05(1H,d,J=5 Hz), 6.10 (1H,dd,J=5 Hz,9 Hz), 6.43(1H,s), 6.97(1H,s), 7.21–7.39(40H,m)

PREPARATION EXAMPLE 46

Benzhydryl 7-[(Z)-2-(2-tritylaminothiazol-4-yl)-2-trityloxyiminoacetamido]-3-N-(2-methoxyethyl)-carbamoyloxymethyl-3-cephem-4-carboxylate

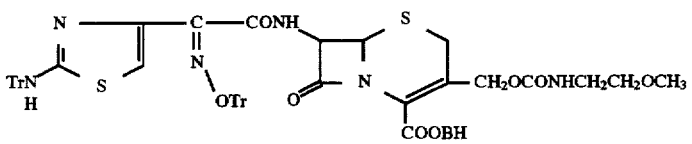

In a similar manner to Preparation Example 45, the title compound was obtained (yield: 53%).

NMR (CDCl$_3$, δ): 3.32–3.38(5H,m), 3.42(2H,t,J=5 Hz), 3.25,3.49 (2H,ABq,J=18 Hz), 4.78,5.05(2H,ABq,J=12 Hz), 5.08(1H,d,J=5 Hz), 6.1(1H,dd,J=5 Hz,9 Hz), 6.42(1H,s), 6.94(1H,s), 7.3–7.4(40H,m)

PREPARATION EXAMPLE 47

Benzhydryl 7-[(Z)-2-(2-tritylaminothiazol-4-yl)-2-trityloxyacetamido]-3-N-(2-monofluoroethyl)-carbamoyloxymethyl-3-cephem-4-carboxylate

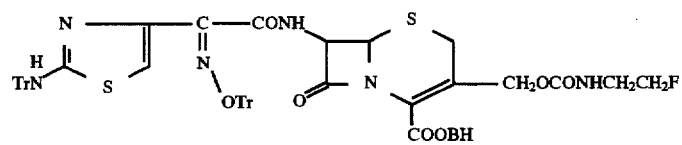

In a similar manner to Preparation Example 45, the title compound was obtained.

NMR (CDCl₃, δ): 3.1–3.4(4H,m), 4.2–4.4(2H,m), 4.85 (2H,ABq,J=14 Hz), 4.92(1H,d,J=4.9 Hz), 6.04(1H,dd,J=4.9 Hz,8.9 Hz), 6.44(1H,s), 6.95(1H,s), 7.1–7.5(40H,m)

PREPARATION EXAMPLE 48

Benzhydryl 7-[(Z)-2-(2-tritylaminothiazol-4-yl)-2-trityloxyacetamido]-3-N-(2,2,2-trifluoroethyl)-carbamoyloxymethyl-3-cephem-4-carboxylate

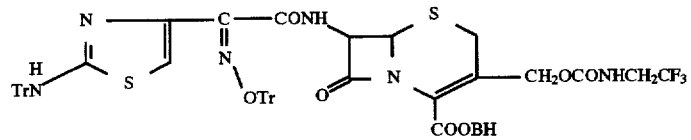

In a similar manner to Preparation Example 45, the title compound was obtained.

NMR (CDCl₃): 3.21(2H,ABq,J=19 Hz), 3.52–3.58(2H, m), 4.88(2H,ABq, J=14 Hz), 4.91(1H,d,J=4.9 Hz), 6.03(1H, dd,J=4.9 Hz, 8.8 Hz), 6.45(1H,s), 6.95(1H,s), 7.13–7.47 (40H,m)

EXAMPLE 45

Sodium 7-[(Z)-2-(2-aminothiazol-4-yl)-2-hydroxyiminoacetamido]-3-N-methylcarbamoyl-oxymethyl-3-cephem-carboxylate

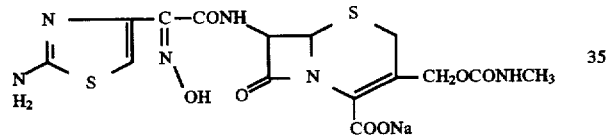

To a solution of the compound (5.35 g), which had been obtained in Preparation Example 45, in anisole (25 ml), trifluoroacetic acid (20 ml) was added under ice cooling, followed by stirring at the same temperature for one hour. The reaction mixture was added with isopropyl ether and the precipitate was collected by filtration. The powdery solid thus obtained was added with formic acid (35 ml), followed by stirring at room temperature for one hour. The solvent was distilled off under reduced pressure and the residue was diluted with methanol. The resulting solution was added with sodium acetate (1.0 g), and methanol was distilled off. The residue thus obtained was diluted with ethyl acetate and then, formed into powder in isopropyl ether. The powder thus obtained was purified by liquid chromatography, whereby the title compound was obtained (yield: 326 mg; 14%).

NMR (D₂O, δ): 2.54(3H,s), 3.21,3.51(2H,ABq,J=18 Hz), 4.60,4.70 (2H,ABq,J=18 Hz), 5.06(1H,d,J=4.8 Hz), 5.69 (1H,d, J=4.8 Hz), 6.83(1H,s)

EXAMPLE 46

Sodium 7-[(Z)-2-(2-aminothiazol-4-yl)-2-hydroxyiminoacetamido]-3-N-(2-methoxyethyl)-carbamoyloxymethyl-3-cephem-4-carboxylate

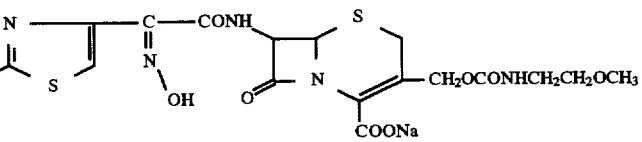

The compound, which had been obtained in Preparation Example 46, was treated in a similar manner to Example 45, whereby the title compound was obtained (yield: 46%).

NMR (D₂O,δ): 3.17(2H,t,J=5 Hz), 3.20(3H,s), 3.26,3.53 (2H, ABq,J=18 Hz), 3.40(2H,t,J=5 Hz), 4.55,4.76(2H, ABq, J=12 Hz), 5.09(1H,d,J=5 Hz), 5.71(1H,d,J=5 Hz),

EXAMPLE 47

Sodium 7-[(Z)-2-(2-aminothiazol-4-yl)-2-hydroxyiminoacetamido]-3-N-(2-monofluoroethyl)-carbamoyloxymethyl-3-cephem-4-carboxylate

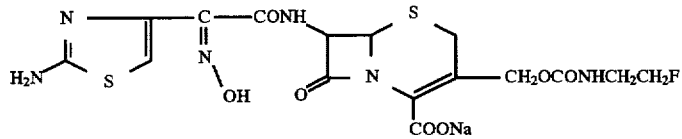

The compound, which had been obtained in Preparation Example 47, was treated in a similar manner to Example 45, whereby the title compound was obtained.

NMR (D$_2$O,δ): 3.2–3.5(4H,m), 4.2–4.4(2H,m), 4.65(2H, ABq,J=12 Hz), 5.05(1H,d,J=4.8 Hz), 5.68(1H,d,J=4.8 Hz), 6.80(1H,s)

EXAMPLE 48

Sodium 7-[(Z)-2-(2-aminothiazol-4-yl)-2-hydroxyiminoacetamido]- 3-N-(2,2,2-trifluoroethyl) carbamoyloxymethyl-3-cephem-4-carboxylate

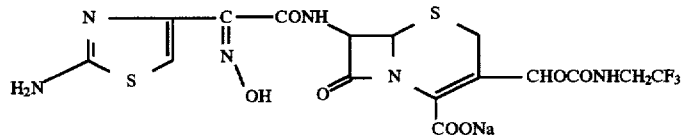

The compound which had been obtained in Preparation Example 48, was treated in a similar manner to Example 45, whereby the title compound was obtained.

NMR (D$_2$O,δ): 3.39(2H,ABq,J=18 Hz), 3.66–3.73(2H, m), 4.71(2H, ABq,J=13 Hz), 5.08(1H,d,J=4.8 Hz), 5.70(1H, d, J=4.8 Hz), 6.81(1H,s)

EXAMPLE 49

Pivaloyloxymethyl 7-[(Z)-2-(2-aminothiazol-4-yl)-2-hydroxyiminoacetamido]-3-N-methylcarbamoyl-oxymethyl-3-cephem-4-carboxylate

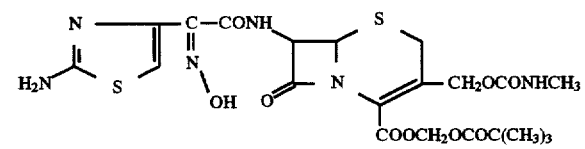

To a solution of the compound (106 mg), which had been obtained in Example 45, in N,N-dimethylacetamide (2 ml), iodomethyl pivalate (51 mg) was added, followed by stirring at the same temperature for one hour. The reaction mixture was added with ethyl acetate and water. Then, the ethyl acetate layer was collected and washed with saturated aqueous sodium chloride solution, followed by drying over anhydrous magnesium sulfate. The solvent was distilled off under reduced pressure. The residue thus obtained was dissolved in ethyl acetate and the resulting solution was added with isopropyl ether. A precipitate so formed was collected by filtration and washed with isopropyl ether, whereby the title compound was obtained (yield: 44 mg; 35%).

NMR (CDCl$_3$,δ): 1.13–1.15(9H,m), 2.70(3H,s), 3.42–3.59(2H,m), 4.72–4.76(1H,m), 4.95–5.05(2H,m), 5.78–5.81(1H,m), 5.81–5.89(2H,m), 6.93(1H,s)

EXAMPLE 50

1-(Isopropoxycarbonyloxy)ethyl 7-[(Z)-2-(2-aminothiazol-4-yl)-2-hydroxyiminoacetamido]-3-N-methylcarbamoyloxymethyl-3-cephem-4-carboxylate

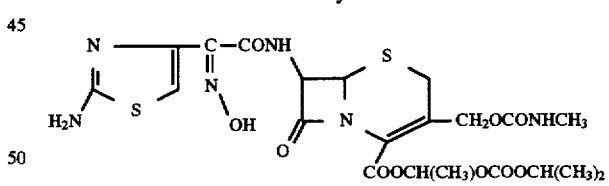

In a similar manner to Example 49, the title compound was obtained (yield: 55%).

NMR (CD$_3$OD,δ): 1.25–1.35(9H,m), 1.51–1.57(3H,m), 2.70(3H,s), 3.48–3.70(2H,m), 4.75–4.90(1H,m), 5.02–5.09 (1H,ABq, J=14 Hz), 5.16–5.21(1H,m), 5.90–5.95(1H,m), 6.75(1H,s), 6.84–6.95(1H,m)

EXAMPLE 51

Pivaloyloxymethyl 7-[(Z)-2-(2-aminothiazol-4-yl)-2-hydroxyiminoacetamido]-3-N-(2-methoxyethyl)-carbamoyloxymethyl-3-cephem-4-carboxylate

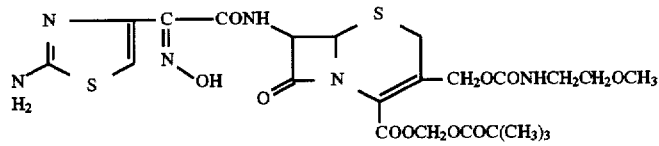

The compound, which had been obtained in Preparation Example 46, was treated in a similar manner to Example 49, whereby the title compound was obtained.

NMR (CDCl$_3$,δ): 1.26–1.28(9H,m), 3.36–3.40(5H,m), 3.47–3.50(3H,m), 3.62(1H,d,J=18 Hz), 4.84,5.10(2H,ABq, J=13 Hz), 5.04(1H,d,J=3.5 Hz), 5.86,5.96(2H,ABq,J=5 Hz), 5.91–5.94(1H,m), 7.05(1H,s)

EXAMPLE 52

Pivaloyloxymethyl 7-[(Z)-2-(2-aminothiazol-4-yl)-2-hydroxyiminoacetamido]-3-N-(2-monofluoroethyl)-carbamoyloxymethyl-3-cephem-4-carboxylate

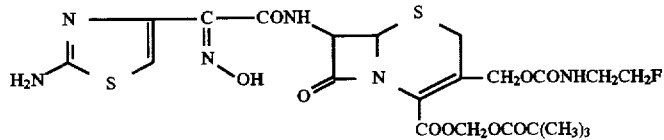

The compound, which had been obtained in Preparation Example 47, was treated in a similar manner to Example 49, whereby the title compound was obtained.

NMR (CD$_3$OD,δ): 1.22(9H,s), 3.3–3.4(2H,m), 3.63(2H, ABq,J=18 Hz), 4.35–4.50(2H,m), 4.96(2H,ABq,J=13 Hz), 5.20(1H,d,J=4.8 Hz), 5.83–5.94(3H,m), 6.76(1H,s)

EXAMPLE 53

Pivaloyloxymethyl 7-[(Z)-2-(2-aminothiazol-4-yl)-2-hydroxyiminoacetamido]-3-N-(2,2,2-trifluoroethyl)carbamoyloxymethyl-3-cephem-4-carboxylate

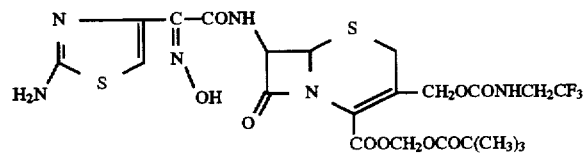

The compound, which had been obtained in Preparation Example 48, was treated in a similar manner to Example 49, whereby the title compound was obtained.

NMR (CD$_3$OD,δ): 1.21(9H,s), 3.61(2H,ABq,J=18 Hz), 3.74–3.81(2H,m), 5.00(2H,ABq,J=14 Hz), 5.19(1H,d,J=4.9 Hz), 5.83–5.94 (3H,m), 6.76(1H,s).

EXAMPLE 54

Sodium 7-formamido-3-N,N-dimethylcarbamoyloxymethyl-3-cephem-4-carboxylate

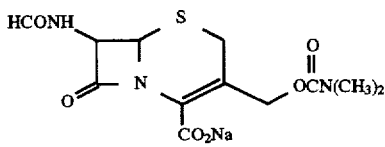

Benzhydryl 7-formamido-3-N,N-dimethylcarbamoyl-oxymethyl-3-cephem-4-carboxylate (139 g) was dissolved in methylene chloride (1.4 l). The resulting solution was added with anisole (69.5 ml) and trifluoroacetic acid (348 m l), followed by stirring for 30 minutes. After the reaction, the solvent was distilled off under reduced pressure. After the residue thus obtained was dissolved in a small amount of ethyl acetate, trituration was applied in a mixed solvent of diisopropyl ether and diethyl ether. Crystals precipitated were collected by filtration. Then, the crystals were dissolved in methanol (500 ml), followed by the addition of sodium acetate (34.5 g) and isopropyl alcohol (500 ml). The resulting crystals were collected by filtration. After the crystals were washed with diisopropyl ether, they were air-dried, whereby the title compound was obtained (yield: 80.2 g; 82%).

NMR (D$_2$O, δ): 2.75(6H,s), 3.30,3.53(2H,ABq,J=18.1 Hz), 4.53,4.81(2H,ABq,J=12.8 Hz), 5.00(1H,d,J=4.8 Hz), 5.61 (1H,d,J=4.8 Hz), 8.08(1H,s)

EXAMPLE 55

1-(Isopropoxycarbonyloxy)ethyl 7-formamido-3-N,N-dimethylcarbamoyloxymethyl-3-cephem-4-carboxylate

After the compound (84 g), which had been obtained in Example 54, Was dissolved in dimethyl formamide (420 ml), the resulting solution was added with iodo-1- isopropoxycarbonyloxyethane (61.7 g) under ice cooling, followed by stirring for 2 hours. After the reaction, the reaction mixture was poured into a mixed solvent of water and ethyl acetate. The resulting mixture was allowed to stand and the organic layer was collected. The resulting organic layer was washed with water, a 10% aqueous solution of sodium thiosulfate and saturated aqueous sodium chloride solution, followed by drying over magnesium sulfate. The solvent was distilled off under reduced pressure. Then, the residue was subjected to column chromatography, whereby the title compound was obtained (yield: 44.7 g; 40%).

NMR (CDCl$_3$, δ): 1.29–1.34(6H,m), 1.57–1.59(3H,m), 2.91(6H,s), 3.46–3.62(2H,m), 4.86–5.22(4H,m), 5.88–5.95 (1H,m), 6.39(0.5H,d,J=9.3 Hz), 6.47(0.5H,d,J=9.2 Hz), 6.88–6.92(0.5H,m), 6.98–7.02(0.5H,m), 8.27(0.5H,s), 8.28 (0.5H,s)

EXAMPLE 56

1-(Isopropoxycarbonyloxy)ethyl 7-amino-3-N,N-dimethylcarbamoyloxymethyl-3-cephem-4-carboxylate hydrochloride

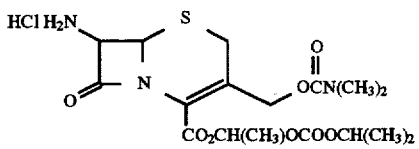

After the compound (44.2 g), which had been obtained in Example 55, was dissolved in a mixed solvent of methanol (440 ml) and tetrahydrofuran (220 ml), the resulting solution was added with concentrated hydrochloric acid (45 ml), followed by stirring at room temperature for 5 hours. After the reaction, the solvent was distilled off under reduced pressure. The residue was poured into a mixed solvent of water and ethyl acetate and the resulting solution was adjusted to pH 6.5 with aqueous sodium bicarbonate solution. The organic layer was collected and then washed with saturated sodium chloride solution. After the organic layer was dried over sodium sulfate, a solution of hydrochloric acid in ethyl acetate was added. The solvent was distilled off under reduced pressure, whereby the title compound was obtained (yield: 47 g; 100%)

NMR (CDCl$_3$, δ): 1.23–1.30(6H,m), 1.54–1.57(3H,m), 2.90(6H,s), 3.49,3.81(1H,ABq,J=17.0 Hz), 3.50,3.80(1H, ABq, J=17.2 Hz), 4.86–5.29(5H,m), 6.83–6.86(1H,m)

EXAMPLE 57

1-(Isopropoxycarbonyloxy)ethyl 7-(4-bromo-3-oxobutyrylamino)-3-N,N-dimethylcarbamoyloxymethyl-3-cephem-4-carboxylate

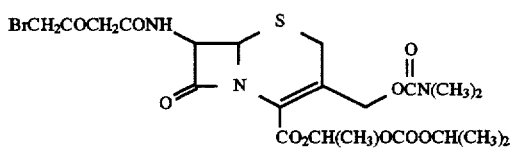

After diketene (0.92 ml) was dissolved in methylene chloride (10 ml), the resulting solution was cooled to –30° C. and stirred. The reaction mixture was added dropwise with a methylene chloride solution (3 ml) containing bromine (0.66 ml) to prepare 4-bromo-3-oxobutyric acid bromide.

On the other hand, 1-(isopropyloxycarbonyloxy)-ethyl 7-amino-3-N,N-dimethylcarbamoyloxymethyl-3-cephem-4-carboxylate (5.05 g) was dissolved in methylene chloride (60 ml) together with bistrimethylsilylacetamide (5.8 ml). The resulting solution was added dropwise with the 4-bromo-3-oxobutyric acid bromide solution, which had been obtained above, at –30° C., followed by stirring for one hour under ice cooling. The reaction mixture was washed successively with water and saturated sodium chloride solution, followed by drying over anhydrous magnesium sulfate and then by concentration under reduced pressure. The concentrate was subjected to chromatography on a column packed with 150 g of silica gel, whereby the title compound was obtained (yield: 4.8 g; 68.9%).

NMR (CDCl$_3$, δ): 1.28–1.34(6H,m), 1.59(3H,d,J=5 Hz), 2.92(6H,s), 3.49,3.88(2H,ABq,J=19 Hz), 3.51–3.75(2H,m), 4.03–4.07(2H,m), 4.85–5.27(4H,m), 5.80–5.90(1H,m), 6.91 (0.5Hq,J=5 Hz), 7.00(0.5H,q,J=5 Hz)

EXAMPLE 58

1-(Isopropoxycarbonyloxy)ethyl 7-(4-bromo-3-oxo-2-hydroxyiminobutyrylamino)-3-N,N-dimethylcarbamoyloxymethyl-3-cephem-4-carboxylate

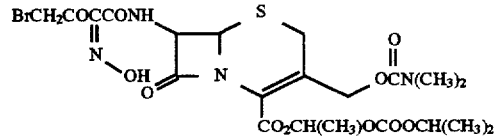

The compound (4.5 g), which had been obtained in Example 57, was dissolved in acetic acid (45 ml) and the resulting solution was added with sodium nitrite (0.58 g) under ice cooling, followed by stirring at room temperature for one hour. The reaction mixture was added with ethyl acetate. The resulting mixture was washed with water and a saturated sodium chloride solution, followed by drying over anhydrous magnesium sulfate and then by concentration under reduced pressure. The concentrate was subjected to chromatography on a column packed with 100 g of silica gel, whereby the title compound was obtained (yield: 3.76 g; 79.6%).

NMR (CDCl$_3$, δ): 1.30–1.34(6H,m), 1.56–1.61(3H,m), 2.93(6H,s), 3.50–3.68(3H,m), 4.54(2H,s), 4.87–5.30(4H,m), 5.84– 5.90(1H,m), 6.92(0.5H,q,J=5.5 Hz), 7.01(0.5H,q, J=5.5 Hz), 9.40–9.45(1H,m)

EXAMPLE 59

1-(Isopropyloxycarbonyloxy)ethyl 7-[(Z)-2-(2-aminothiazol-4-yl)-2-hydroxyiminoacetamide]-3-N,N-dimethylcarbamoyloxymethyl-3-cephem-4-carboxylate

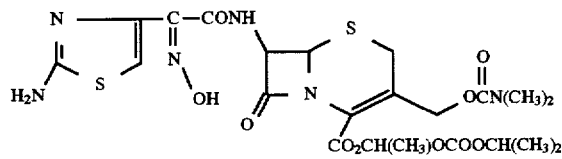

The compound (1.0 g), which had been obtained in Example 58, was dissolved in dimethylacetamide (15 ml) and the resulting solution was added with thiourea (0.244 g), followed by stirring at 5° C. for 12 hours. The reaction mixture was added with ethyl acetate (200 ml). The resulting mixture was washed with water and saturated sodium chloride solution, followed by drying over anhydrous magnesium sulfate and then by concentration under reduced pressure. The concentrate was dissolved in ethyl acetate (10 ml). The resulting solution was added dropwise to isopropyl ether (150 ml) under stirring. The resulting precipitate was collected by filtration and then dried, whereby the title compound was obtained (yield: 0.6 g; 62.3%).

NMR (CDCl$_3$, δ): 1.26–1.37(6H,m), 1.58–1.62(3H,m), 2.93(6H,s), 3.50(1H,d,J=19 Hz), 3.60,3.61(together, 1H,d, J=19 Hz), 4.9–5.24(3H,m), 5.04,5.07(together, 1H,d,J=5 Hz), 5.93(1H,dd,J=5 Hz,8 Hz), 6.92,7.02(together, 1H,q,J= 5.5 Hz), 7.08(1H,s)

EXAMPLE 60

1-(Isopropoxycarbonyloxy)ethyl 7-[4-chloro-3-oxobutyrylamino)-3-N,N-dimethylcarbamoyloxymethyl-3-cephem-4-carboxylate

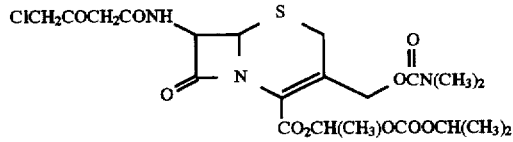

Diketene (21 ml) was dissolved in methylene chloride (60 ml), followed by cooling to −30° C. Chlorine gas was spurged through the resulting solution until the latter turned to a pale yellow color. Excess chlorine was purged out with nitrogen gas, and in addition, methylene chloride was distilled off under reduced pressure. The residue was distilled, whereby 4-chloro-3-oxobutyric acid chloride having a boiling point of 75°–85° C. (8 mm/Hg) was obtained (7.1 g).

On the other hand, 1-(isopropyloxycarbonyloxy)-ethyl 7-amino-3-N,N-dimethylcarbamoyloxymethyl-3-cephem-4-carboxylate ester (3 g) was dissolved in methylene chloride (45 ml). The resulting solution was added with N,N-dimethylaniline (0.98 ml) under ice cooling, followed by stirring. The reaction mixture was added dropwise with a solution of 4-chloro-3-oxybutyric acid chloride (1.2 g), which had been obtained above, in methylene chloride (15 ml) at −30° C. After the resulting solution was stirred for one hour under ice cooling, the reaction mixture was washed successively with water and saturated sodium chloride solution, followed by drying over anhydrous magnesium sulfate and then by concentration under reduced pressure. The concentrate was subjected to chromatography on a column packed with 70 g of silica gel, whereby the title compound was obtained (yield: 0.59 g; 25.1%).

NMR (CDCl$_3$, δ): 1.29–1.33(6H,m), 1.58(3H,d,J=5 Hz), 1.58(1.5H,s), 1.59(1.5H,s), 2.92(6H,s), 3.46–4.26(6H,m), 4.85–5.35(4H,m), 5.80–5.87(1H,m), 6.90(0.5H,q,J=5 Hz), 6.99(0.5H,q,J=5 Hz), 7.53(0.5H,q,J=9 Hz), 7.61(0.5H,q,J:9 Hz)

EXAMPLE 61

1-(Isopropoxycarbonyloxy)ethyl 7-(4-chloro-3-oxo-2-hydroxyiminobutyrylamino)-3-N,N-dimethylcarbamoyloxymethyl-3-cephem-4-carboxylate

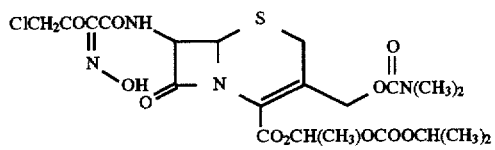

The compound (0.5 g), which had been obtained in Example 60, was dissolved in methylene chloride (5 ml) and then, acetyl chloride (0.092 ml) and isoamyl nitrite (0.167 ml) were added to the resulting solution at room temperature. At the same temperature, the resulting solution was stirred for 5.5 hours. The reaction mixture was washed with water and saturated sodium chloride solution, followed by drying over anhydrous magnesium sulfate and then by concentration under reduced pressure. The concentrate thus obtained was subjected to chromatography on a silica gel column, whereby the title compound was obtained (yield: 0.48 g; 77.3%)

NMR (CDCl$_3$, δ): 1.29–1.34(6H,m), 1.59(3H,d,J=5.5 Hz), 2.93(3H,s), 3.51–3.66(2H,m), 4.78(2H,s), 4.82–4.98 (1.5H,m), 5.14–5.31(1.5H,m), 5.05–5.08(1H,m), 5.84–5.90 (1H,m), 6.91(0.5H,q,J=5.5 Hz), 7.00(0.5H,q,J=5.5 Hz), 9.35–9.40(1H,m)

EXAMPLE 62

1-(Isopropoxycarbonyloxy)ethyl 7-[(Z)-2-(2-aminothiazol-4-yl)-2-hydroxyiminoacetamido)-3-N,N-dimethylcarbamoyloxymethyl-3-cephem-4-carboxylate

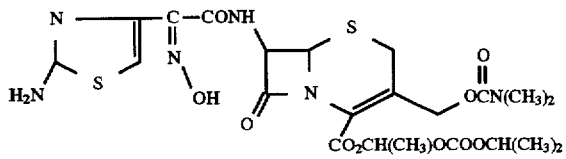

The compound (0.48 g), which had been obtained in Example 61, was dissolved in dimethylacetamide (7 ml). The resulting solution was added with thiourea (0.126 g), followed by stirring at 5° C. for 16 hours. The reaction mixture was added with ethyl acetate (80 ml). The resulting mixture was washed with water and an aqueous sodium chloride solution, followed by drying over anhydrous magnesium sulfate and then by concentration under reduced pressure. The precipitate was dissolved in ethyl acetate (5 ml) and the resulting solution was added dropwise to isopropyl ether (70 ml) under stirring. The precipitate was collected by filtration and dried, whereby the title compound was obtained (yield: 0.252 g; 50.6%). NMR and HPLC data of the compound obtained in this example were consistent with those of the compound obtained in Example 59.

EXAMPLE 63

Benzhydryl 7-formamido-3-p-nitrophenoxycarbonyloxymethyl-3-cephem-4-carboxylate ester

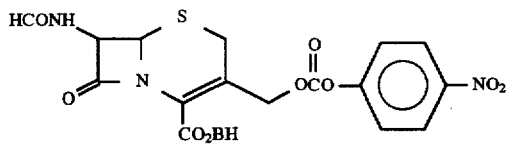

Benzhydryl 7-formamido-3-hydroxymethyl-3-cephem-4-carboxylate ester (106 g) and p-nitrophenyl chloroformate (50.4 g) were stirred in tetrahydrofuran (700 ml) under ice cooling. To the resulting suspension, pyridine (19.8 g) was added dropwise over 5 minutes. After 35 minutes, the mixture was poured into a mixed solvent of ethyl acetate (1 l) and water (1 l). The organic layer was washed twice with water (0.5 ml) and once with saturated sodium chloride solution, followed by drying over magnesium sulfate. The solvent was distilled off under reduced pressure until its volume was decreased to about 400 ml. The residue was gradually poured into isopropyl ether (2 l) and the resulting crystals were collected by filtration, whereby the title compound was obtained (yield: 133 g; 90%).

NMR (DMSO-d₆, δ): 3.67,3.77(2H,ABq,J=18 Hz), 4.91, 5.11(2H,ABq,J=12 Hz), 5.21(1H,J=4.8 Hz), 5.91(1H,dd,J= 4.8 Hz,8.5 Hz), 6.91(1H,s), 7.2–7.5(12H,m), 8.14(2H,d,J=9 Hz), 8.31(2H,d,J=9 Hz), 9.11(1H,d,J=8.5 Hz)

EXAMPLE 64

7-Formamido-3-p-nitrophenoxycarbonyloxymethyl-3-cephem-4-carboxylic acid

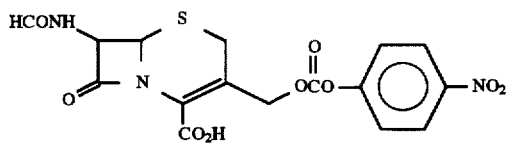

The compound (133 g), which had been obtained in Example 63, was suspended in dichloromethane (265 ml) under stirring. To the suspension, trifluoroacetic acid (200 ml) was added dropwise over 25 minutes under ice cooling. Ten 10 minutes later, the resulting suspension was poured into isopropyl ether (2.5 l). The resulting crystals were collected by filtration and then washed with isopropyl ether, whereby the title compound was obtained (yield 103 g; 97.4%.

NMR (DMSO-d₆, δ): 3.62,3.72(2H,ABq,J=18 Hz), 4.94, 5.23(2H,ABq, J=12.6 Hz), 5.15(1H,J=4.9 Hz), 5.81(1H,dd, J=4.9 Hz,8.8 Hz), 7.56(2H,d,J=9 Hz), 8.13(1H,s), 8.30(2H, d,J=9 Hz), 9.07(1H,d,J=8.8 Hz)

EXAMPLE 65

Benzhydryl 7-thienylacetamido-3-p-nitrophenoxycarbonyloxymethyl-3-cephem-4-carboxylate ester

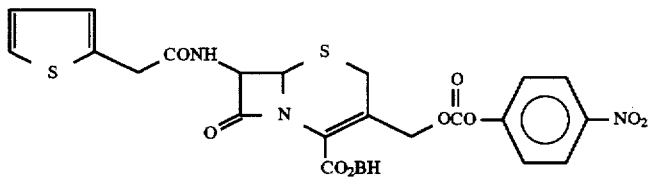

Benzhydryl 7-thienylacetamido-3-hydroxymethyl-3-cephem-4-carboxylate (1.6 g) and p-nitrophenylchloroformate (0.6 g) were treated in a similar manner to Example 63, whereby the title compound was obtained [yield: 2.3 g (stoichiometric)].

NMR (CDCl₃, δ): 3.43,3.62(2H,ABq,J=19 Hz), 4.85(2H, s), 4.97,5.24 (2H,ABq,J=13 Hz), 5.01(1H,d,J=4.5 Hz), 5.91 (1H, dd, J=4.5 Hz,9 Hz), 6.93(1H,s), 6.97–7.02(2H,m), 7.24–7.38(11H,m), 7.42(2H,d,J=8 Hz), 8.26(2H,d,J=8 Hz)

EXAMPLE 66

7-Thienylacetamido-3-p-nitrophenoxycarbonyloxymethyl-3-cephem-4-carboxylic acid

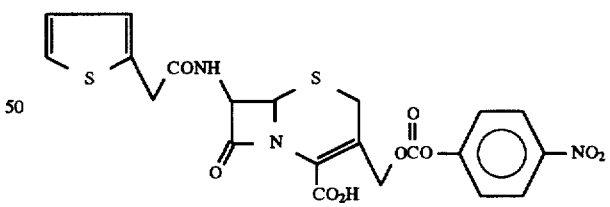

The compound (1.4 g), which had been obtained Example 65, trifluoroacetic acid (1 ml) and anisole ml) were stirred for 30 minutes under ice cooling. The reaction mixture was added with isopropyl ether (50 ml) and the resulting precipitate was collected by filtration, whereby the title compound was obtained (yield: 900 mg; 85%)

NMR (CD₃OD, δ): 3.57,3.73(2H,ABq,J=19 Hz), 3.80 (2H,s), 5.06,5.33 (2H,ABq,J=12 Hz), 5.09(1H,d,J=4.5 Hz), 5.77(1H,d, J=4.5 Hz), 6.9–7.0(2H,m), 7.23–7.28(1H,m), 7.46(2H,d,J=8 Hz), 8.29(2H,d,J=8 Hz)

EXAMPLE 67

Benzhydryl 7-formamido-3-phenoxycarbonyloxymethyl-3-cephem-4-carboxylate

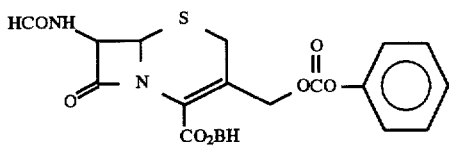

In a similar manner to Example 63 except that p-nitrophenyl chloroformate was replaced by phenyl chloroformate, the title compound was obtained (yield 90%).

NMR (DMSO-d$_6$, δ): 3.66,3.75(2H,ABq,J=19 Hz), 4.85, 5.05(2H,ABq,J=14 Hz), 5.21(1H,d,J=4.5 Hz), 5.91(1H,dd, J=4.8 Hz,8 Hz), 6.90 (1H,s), 7.17–7.50(15H,m), 8.14(1H,s), 9.11(1H,d,J=8 Hz)

EXAMPLE 68

7-Formamido-3-phenoxycarbonyloxymethyl-3-cephem-4-carboxylic acid

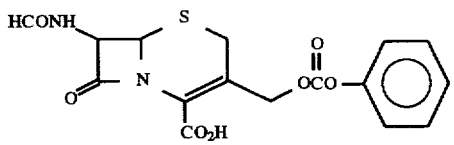

The compound, which had been obtained in Example 67, was treated in a similar manner to Example 64, whereby the title compound was obtained (yield 90%).

NMR (DMSO-d$_6$, δ): 3.61,3.72(2H,ABq,J=18 Hz), 4.89, 5.19(2H,ABq,J=12 Hz), 5.14 (1H,d,J=4.5 Hz,8 Hz), 7.20–7.45(5H,m), 8.12(1H,s), 9.06(1H,d,J=8 Hz)

EXAMPLE 69

Sodium 7-formamido-3-N,N-dimethylcarbamoyloxymethyl-3-cephem-4-carboxylate

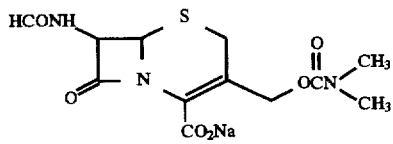

The compound (103 g), which had been obtained in Example 64, was dissolved in methanol (600 ml). Tetrahydrofuran (44 ml) containing 22 g of dimethylamine was added dropwise to the resulting solution over minutes under ice cooling. One hour later, the resulting solution was added with sodium acetate (24 g), followed by concentration under reduced pressure. To the residue, isopropyl alcohol (0.8 l) and then isopropyl ether (1.5 l) were added, respectively. The resulting precipitate was collected by filtration. The solid thus obtained was dissolved in methanol (0.5 l). After the crystals were formed, isopropyl ether (1.5 l) was added and then, the resulting solution was filtered, whereby the title compound was obtained (yield: 72 g; 84%).

NMR (DMSO-d$_6$, δ): 2.79(6H,s), 3.22,3.46(2H,ABq,J= 17.2 Hz), 4.68,4.94 (2H,ABq, J=12.0 Hz), 4.96(1H,d,J=4.8 Hz), 5.55(1H,dd, J=4.8 Hz,9 Hz), 8.10(1H,s), 8.93(1H,d,J=9 Hz)

EXAMPLE 70

7-Thienylacetamido-3-N,N-dimethylcarbamoyloxymethyl-3-cephem-4-carboxylic acid

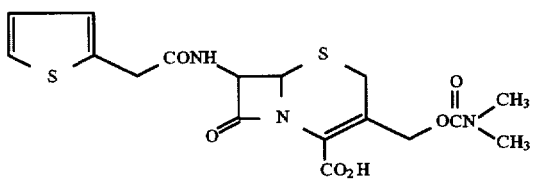

The compound (100 mg), which had been obtained in Example 66, was dissolved in N,N-dimethylformamide (1 ml). The resulting solution was added with a 50% aqueous solution of dimethylamine (50 mg) under ice cooling, followed by reaction for 15 minutes. To the reaction mixture, ethyl acetate (50 ml) and water (30 ml) were added. Then, the organic layer was collected, washed with water and saturated aqueous sodium chloride solution, dried over magnesium sulfate and concentrated under reduced pressure. The residue was added with isopropyl ether. The resulting solid was collected by filtration, whereby the title compound was obtained (yield: 60 mg; 75%).

NMR (DMSO-d$_6$, δ): 2.82(3H,s), 2.84(3H,s), 3.48,3.60 (2H,ABq,J=19 Hz), 3.78(2H,s), 4.48,4.99(2H,ABq,J=11 Hz), 5.09(1H, d,J=4.5 Hz), 5.64(1H,dd,J=4.5 Hz,8 Hz), 6.92–7.00(2H,m), 7.38(1H,d,J=3 Hz), 9.12(1H,d,J=8 Hz)

EXAMPLE 71

Sodium 7-formamido-3-N,N-dimethylcarbamoyloxymethyl-3-cephem-4-carboxylate

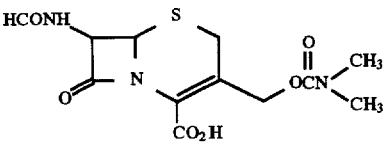

The compound, which had been obtained in Example 68, was treated in a similar manner to Example 69, whereby the title compound was obtained (yield: 35%).

The compound obtained in this example conformed with the compound obtained in Example 69 in all physicochemical properties such as HPLC. (high performance liquid chromatography), TLC. (thin-layer chromatography) and NMR spectrum.

PREPARATION EXAMPLE 49

Tert-butyl 7-phenylacetamido-3-hydroxymethyl-3-cephem-4-carboxylate-1-oxide

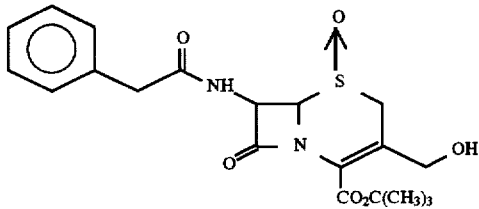

To a solution of tert-butyl 7-phenylacetamido-3-bromomethyl-3-cephem-4-carboxylate-1-oxide (76.1 g; 0.158 mol) in N,N-dimethylformamide (350 ml), ammonium trifluoroacetate (41.3 g; 0.316 mol) and sodium iodide (23.6 g; 0.158 mol) were added, followed by stirring at room temperature. The reaction mixture was added with ammonium trifluoroacetate (10.3 g; 0.079 mol) upon an elapsed time of 4 hours and 35 minutes from the initiation of the stirring and-then with sodium iodide (11.8 g, 0.079 mol) upon an elapsed time of 8 hours and 5 minutes after the initiation of the stirring. Stirring was continued at room temperature for 24 hours and 25 minutes in total. The reaction mixture was poured into a mixture of ethyl acetate, and water and the ethyl acetate layer was collected. The water layer was extracted twice with ethyl acetate. Ethyl acetate layers were combined together, successively washed with water and saturated aqueous sodium chloride solution, and then dried over magnesium sulfate. The solvent was then distilled off under reduced pressure, whereby tert-butyl 7-phenylacetamido-3-hydroxymethyl-3-cephem-4-carboxylate-1-oxide was obtained (yield: 63.5 g; 96.1%).

NMR (CDCl$_3$, δ): 1.58(9H,s), 3.00(1H,br.s), 3.17,3.94 (2H,ABq, J=18.7 Hz), 3.62(2H,s), 4.13,4.47 (2H,ABq,J= 13.2 Hz), 4.42(1H,d,J=4.8 Hz), 6.02(1H,dd,J=4.8 Hz,9.7 Hz), 6.90(1H,d,J=9.7 Hz), 7.24–7.30(5H,m)

PREPARATION EXAMPLE 50

Tert-butyl 7-phenylacetamido-3-N,N-dimethylcarbamoyloxymethyl-3-cephem-4-carboxylate-1-oxide

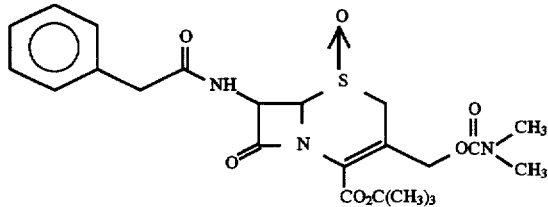

To a solution of tert-butyl 7-phenylacetamido-3-hydroxymethyl-3-cephem-4-carboxylate-1-oxide (63.5 g; 0.151 mol) in tetrahydrofuran (500 ml), N,N'-carbonyldiimidazole (24.5 g; 0.151 mol) was added under ice cooling, followed by stirring at the same temperature for 50 minutes. The reaction mixture was poured into a mixture of ethyl acetate and water and the ethyl acetate layer was collected. The ethyl acetate layer was washed successively with water and a saturated aqueous sodium chloride solution and then dried over magnesium sulfate. The drying agent was filtered off and the filtrate was added with a 50% aqueous solution of dimethylamine (13.6 g; 0.151 mol) under ice cooling. Without changing the temperature, the stirring was continued for 3 hours and 45 minutes. The reaction mixture was poured into a mixture of ethyl acetate and 1N hydrochloric acid, followed by the collection of the ethyl acetate layer. The water layer was extracted further with ethyl acetate. Both ethyl acetate layers were combined together and washed successively with water and saturated aqueous sodium chloride solution, followed by drying over magnesium sulfate. Then, the solvent was distilled off under reduced pressure. The residue was purified by chromatography on a silica gel column, whereby tert-butyl 7-phenylacetamido-3-N,N-dimethylcarbamoyloxymethyl-3-cephem-4-carboxylate-1-oxide was obtained (yield: 15.8 g; 21.2%).

NMR (δ, CDCl$_3$): 1.13(9H,s), 2.88(3H,s), 2.89(3H,s), 3.17,3.80 (2H,ABq,J=19.0 Hz), 3.62(2H,s), 4.42(1H,d,J=4.8 Hz), 4.70,5.31 (2H,ABq,J=14.1 Hz), 6.03(1H, dd,J=4.8 Hz, 9.9 Hz), 6.77(1H,d,J=9.9 Hz), 7.25–7.36(5H,m)

PREPARATION EXAMPLE 51

Tert-butyl 7-Phenylacetamido-3-N,N-dimethylcarbamoyloxymethyl-3-cephem-4-carboxylate

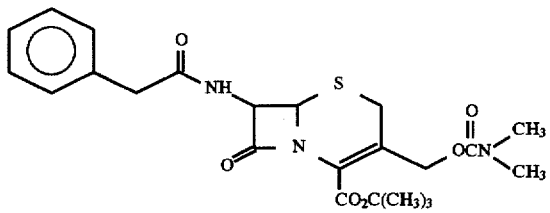

To a solution of tert-butyl 7-phenylacetamido-3-N,N-dimethylcarbamoyloxymethyl-3-cephem-4-carboxylate-1-oxide (15.8 g; 0.0322 mol) in N,N-dimethylformamide (120 ml), phosphorus trichloride (8.4 ml; 0.0963 mol) was added dropwise over 5 minutes under dry ice-methanol cooling so that the solution temperature did not rise beyond −15° C. Then, stirring was continued for 20 minutes under dry ice-methanol cooling. After the reaction mixture was diluted with ethyl acetate, water was added gradually to the mixture under dry ice-methanol cooling so that the liquid temperature did not rise beyond −10° C. The ethyl acetate layer was collected and the water layer was extracted further with ethyl acetate. Both ethyl acetate layers were combined together and washed successively with water and saturated aqueous sodium chloride solution, followed by drying over magnesium sulfate. Then, the solvent was distilled off under reduced pressure. The residue was purified by chromatography on a silica gel column, whereby tert-butyl 7-phenylacetamido-3-N,N-dimethylcarbamoyloxymethyl-3-cephem-4-carboxylate was obtained (9.3 g; 60.8%).

NMR (δ, CDCl$_3$): 1.48(9H,s), 2.88(3H,s), 2.89(3H,s), 3.34,3.50 (2H,ABq,J=18.5 Hz), 3.63(2H,ABq,J=13.6 Hz), 4.92(1H,d,J=4.9 Hz), 4.77,5.09(2H,ABq,J=13.6 Hz), 5.81 (1H,dd,J=4.9 Hz,9.2 Hz), 6.19(1H,d,J=9.2 Hz), 7.24–7.36 (5H,m)

PREPARATION EXAMPLE 52

Sodium 7-phenylacetamido-3-N,N-dimethylcarbamoyloxymethyl-3-cephem-4-carboxylate

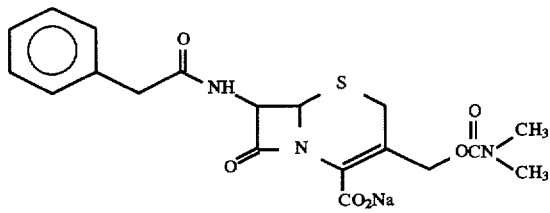

To a solution of tert-butyl 7-phenylacetamido- 3-N,N-dimethylcarbamoyloxymethyl-3-cephem-4-carboxylate (9.2 g) in anisole (4.5 ml) and dichloromethane (50 ml), trifluoroacetic acid (9 ml) was added dropwise under ice cooling. Four and a half hours later, trifluoroacetic acid (18 ml) was added further dropwise at the same temperature. Without changing the temperature, stirring was continued for 6 hours and 20 minutes in total from the beginning of the first dropwise addition. The reaction mixture was concentrated under reduced pressure, followed by the addition of diisopropyl ether. The supernatant was removed by decantation. The residue was dissolved in methanol. To the resulting solution, sodium acetate (1.05 g) was added, followed by stirring until the resulting solution became a homogeneous system. The reaction mixture was added with diisopropyl ether. The precipitate was collected by filtration and, after washing with diisopropyl ether, was dried under reduced pressure. The precipitate was purified by ODS, whereby sodium 7-phenylacetamido-3-N,N-dimethylcarbamoyloxymethyl-3-cephem-4-carboxylate was obtained (yield: 2.2 g; 25.8%).

NMR (δ, D$_2$O): 2.74 (6H,br.s), 3.21,3.47(2H,ABq,J=17.9 Hz), 3.51,3.57 (2H,ABq,J=14.8 Hz), 4.51,4.74 (2H,ABq, J=12.6 Hz), 4.92(1H,d,J=4.6 Hz), 5.48(1H,d,J=4.6 Hz), 7.18–7.28 (5H,m)

PREPARATION EXAMPLE 53

1-(Isopropoxycarbonyloxy)ethyl 7-phenylacetamido-3-(1-dimethylamino)carbonyloxymethyl-3-cephem-4-carboxylate

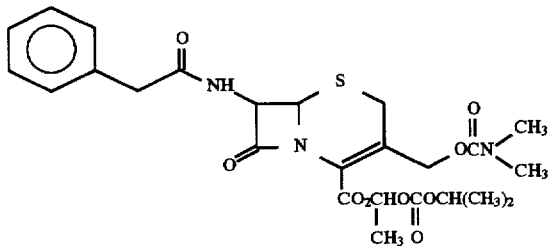

To a solution of sodium 7-phenylacetamido-3-N,N-dimethylcarbamoyloxymethyl-3-cephem-4-carboxylate (2.2 g; 0.005 mol) in N,N-dimethylformamide (20 ml), isopropyl-1-iodoethyl carbonate (1.29 g; 0.005 mol) was added all at once under ice cooling, followed by stirring at the same temperature for 30 minutes. The reaction mixture was poured into a mixture of ethyl acetate and water, and the ethyl acetate layer was collected. The ethyl acetate layer was washed successively with water and saturated aqueous sodium chloride solution, followed by drying over magnesium sulfate. Then, the solvent was distilled off under reduced pressure. The residue was purified by chromatography on a silica gel column, whereby 1-(isopropoxycarbonyloxy)ethyl 7-phenylacetamido-3-N,N-dimethylcarbamoyloxymethyl-3-cephem-4-carboxylate was obtained (yield: 1.43 g; 52.1%).

NMR (δ, CDCl$_3$): 1.22–1.29(6H,m), 1.26(3H,d,J=4.9 Hz), 2.85(6H.br.s), 3.35,3.48(1H,ABq,J=18.4 Hz), 3.36,3.49 (1H,ABq, J=18.4 Hz), 3.55(2H,s), 4.75–4.88(3H,m), 5.04, 5.10(1H,ABq,J=13.9 Hz), 5.71–5.76(1H,m), 6.77–6.82(1H, m), 6.91(0.5Hq,J=5.5 Hz), 6.94(0.5H,d,J=8.9 Hz), 7.19–7.29(5H,m)

EXAMPLE 72

(Isopropoxycarbonyloxy)methyl 7-β-[2-(2-aminothiazol-4-yl)-2-(Z)-hydroxyiminoacetamido]-3-N,N-dimethylcarbamoyloxymethyl-3-cephem-carboxylate hydrochloride

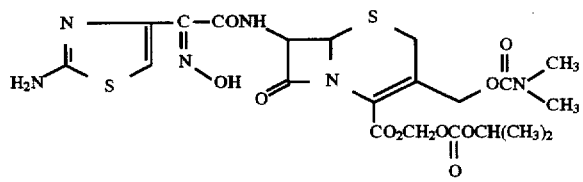

The compound, which had been obtained in Example 63, was reacted with iodomethylisopropyl carbonate, whereby the above compound was obtained (yield: 51%).

NMR (CD$_3$OD,δ): 1.29(6H,m), 2.90(3H,s), 2.92(3H,s), 3.55,3.71 (2H,ABq,J=18 Hz), 4.78,5.13(2H,ABq,J=14 Hz), 5.20(1H,d,J=5 Hz), 5.80(1H,d,J=5 Hz), 5.90–5.97(1H,m), 6.84(1H,s)

EXAMPLE 73

(5-Methyl-2-oxo-1,3-dioxolen-4-yl)methyl 7β-[2-(2-aminothiazol-4-yl)-2-(Z)-hydroxyiminoacetamido]-3-N,N-dimethylcarbamoyloxymethyl-3-cephem-carboxylate hydrochloride

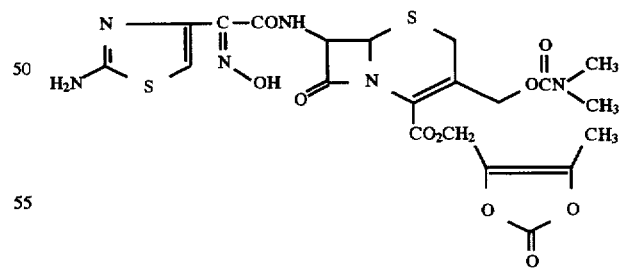

The compound, which had been obtained in Example 63, was reacted with (5-methyl-2-oxo-1,3-dioxolen-4-yl)methyl iodide, whereby the title compound was obtained (yield: 49%).

NMR (CD$_3$OD,δ): 2.2(3H,s), 2.87(3H,s), 2.92(3H,s), 3.52,3.69 (2H,ABq,J=18 Hz), 4.8–5.18(4H,m), 5.20(1H,d, J=5 Hz)

EXAMPLE 74

1-(Isopropoxycarbonyloxy)ethyl 7-amino-3-N,N-dimethylcarbamoyloxymethyl-3-cephem-4-carboxylate (hydrochloride)

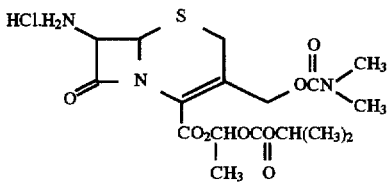

To a solution of phosphorus pentachloride (625 mg; 3 mmol) in dichloromethane (10 ml), pyridine (237 mg; 3 mmol) was added at room temperature, followed by stirring for 20 minutes at the same temperature. The reaction mixture was subjected to ice cooling, to which a solution of 1-(isopropoxycarbonyloxy)-ethyl 7-phenylacetamido-3-N,N-dimethylcarbamoyloxymethyl-3-cephem-4-carboxylate (549 mg, 1 mmol) in dichloromethane (10 ml) was added without changing the temperature. Stirring was continued for one hour and 10 minutes. The reaction mixture was cooled in a dry ice-methanol bath and added with 1,4-butanediol (1 ml) and methanol (1 ml), followed by stirring for 30 minutes. Further, water was added to the reaction mixture at the same temperature. The reaction mixture was then diluted with water and extracted with ethyl acetate. The water layer was controlled to pH 6.5 with a saturated aqueous solution of sodium hydrogen-carbonate and extracted with ethyl acetate. The latter ethyl acetate layer was washed with a saturated aqueous sodium chloride solution, followed by drying over magnesium sulfate. The drying agent was filtered off and the filtrate thus obtained was added with HCl-saturated ethyl acetate. The solvent was distilled off under reduced pressure, whereby 1-(isopropoxycarbonyloxy)-ethyl 7-amino-3-N,N-dimethylcarbamoyloxymethyl-3-cephem-4-carboxylate hydrochloride was obtained (yield: 90 mg; 19.3%).

NMR (δ, CD$_3$OD): 1.21–1.30(6H,m), 1.52–1.55(3H,m), 2.86–3.02(6H,m), 3.70,3.78(1H,ABq,J=18.1 Hz), 3.77,3.82 (1H,ABq, J=13.7 Hz), 4.81–4.92(1H,m), 4.90,5.10(2H, ABq, J=12.8 Hz), 5.11–5.23(0.5,m), 5.28–5.33(0.5,m), 6.82–6.88(0.5,m), 6.91–6.97(0.5,m)

We claim:

1. A compound of the formula

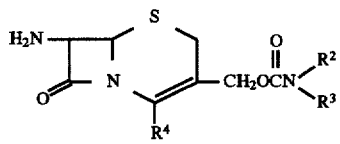

wherein $R^2$ and $R^3$ are the same or different and individually represent a lower alkyl group, a hydroxyl-substituted lower alkyl group, a carbamoyl-substituted lower alkyl group, a cyanosubstituted lower alkyl group, or alternatively $R^2$ and $R^3$ together with nitrogen form a ring selected from the group consisting of azetidinyl, pyrrolidinyl, piperidinyl and morpholinyl groups optionally substituted by one or more lower alkyl, hydroxy and/or hydroxyl-substituted lower alkyl groups; $R^4$ is a carboxyl group or a carboxyl group protected by one or more member selected from the group consisting of 1-(isopropyloxycarbonyloxy)ethyl group, 1-(ethoxycarbonyloxy)ethyl group, 1-(cyclohexyloxycarbonyloxy)ethyl group, pivaloyloxymethyl group and isopropyloxycarbonyloxymethyl group; or a salt thereof.

2. The compound of claim 1, wherein $R^2$ and $R^3$ are both methyl groups and $R^4$ is a carboxyl group or a carboxyl group protected by one or more member selected from the group consisting of 1-(isopropyloxycarbonyloxy)ethyl group, 1-(ethoxycarbonyloxy)ethyl group, 1-(cyclohexyloxycarbonyloxy)ethyl group, pivaloyloxymethyl group and isopropyloxycarbonyloxymethyl group; or a salt thereof.

3. A compound of the formula

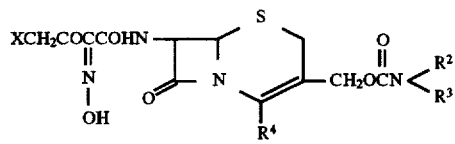

wherein (A) X represents a halogen atom.

(B) $R^2$ and $R^3$ are the same or different and individually represent a lower alkyl group, a hydroxyl-substituted lower alkyl group, a carbamoyl-substituted lower alkyl group, a cyano-substituted lower alkyl group, or alternatively $R^2$ and $R^3$ together with nitrogen form a ring selected from the group consisting of azetidinyl, pyrrolidinyl, piperidinyl and morpholinyl groups optionally substituted by one or more lower alkyl, hydroxy and/or hydroxyl-substituted lower alkyl groups, (C) $R^4$ is a carboxyl group or a carboxyl group protected by one or more member selected from the group consisting of 1-(isopropyloxycarbonyloxy) ethyl group, 1-(ethoxycarbonyloxy)ethyl group, 1-(cyclohexyloxycarbonyloxy) ethyl group, pivaloyloxymethyl group and isopropyloxycarbonyloxymethyl group; or a salt thereof.

4. The compound of claim 3, wherein $R^2$ and $R^3$ are both methyl groups and $R^4$ is a carboxyl group or a carboxyl group protected by one or more member selected from the group consisting of 1-(isopropyloxycarbonyloxy)ethyl group, 1-(ethoxycarbonyloxy)ethyl group, 1-(cyclohexyloxycarbonyloxy)ethyl group, pivaloyloxymethyl group and isopropyloxycarbonyloxymethyl group; or a salt thereof.

* * * * *